United States Patent
Jefson et al.

(10) Patent No.: US 9,981,920 B2
(45) Date of Patent: May 29, 2018

(54) INHIBITORS OF HISTONE DEACETYLASE

(71) Applicant: Rodin Therapeutics, Inc., Cambridge, MA (US)

(72) Inventors: Martin R. Jefson, Stonington, CT (US); Fabian Dey, Basel (CH); Konstanze Konig von Paumbshausen, München (DE); Adrian Schomburg, Gräfelfing (DE); Andreas Schoop, Grafrath (DE); Russell John Thomas, Siena (IT)

(73) Assignee: Rodin Therapeutics, Inc., Cambridge, MA (US)

( * ) Notice: Subject to any disclaimer, the term of this patent is extended or adjusted under 35 U.S.C. 154(b) by 0 days. days.

(21) Appl. No.: 15/321,410

(22) PCT Filed: Jun. 25, 2015

(86) PCT No.: PCT/US2015/037667
§ 371 (c)(1),
(2) Date: Dec. 22, 2016

(87) PCT Pub. No.: WO2015/200619
PCT Pub. Date: Dec. 30, 2015

(65) Prior Publication Data
US 2017/0204070 A1    Jul. 20, 2017

Related U.S. Application Data

(60) Provisional application No. 62/017,688, filed on Jun. 26, 2014.

(51) Int. Cl.
  *C07D 239/60*  (2006.01)
  *C07D 403/12*  (2006.01)
  *C07D 239/95*  (2006.01)
  *C07D 239/52*  (2006.01)

(52) U.S. Cl.
  CPC ......... *C07D 239/60* (2013.01); *C07D 239/52* (2013.01); *C07D 239/95* (2013.01); *C07D 403/12* (2013.01)

(58) Field of Classification Search
  CPC .. C07D 239/60; C07D 239/52; C07D 239/95; C07D 403/12
  See application file for complete search history.

(56) References Cited

U.S. PATENT DOCUMENTS

| | | |
|---|---|---|
| 2004/0242608 A1 | 12/2004 | Durley |
| 2012/0094997 A1 | 4/2012 | England et al. |
| 2014/0018979 A1 | 1/2014 | Goossen et al. |
| 2014/0080802 A1 | 3/2014 | Holson et al. |

FOREIGN PATENT DOCUMENTS

| | | |
|---|---|---|
| WO | 2004/110418 A2 | 12/2004 |
| WO | 2014/018979 A1 | 1/2014 |

OTHER PUBLICATIONS

CAS Registry No. 415714-33-9 (May 14, 2002).*

* cited by examiner

*Primary Examiner* — Alexander R Pagano
(74) *Attorney, Agent, or Firm* — McCarter & English, LLP; Steven G. Davis; Michael J. DeGrazia

(57) ABSTRACT

This invention provides compounds that are inhibitors of HDAC2. The compounds (e.g., compounds according to Formula (I), (II), (IIa), (III), (IV), (V), or (VI)) accordingly are useful for treating, alleviating, or preventing a condition in a subject such as a neurological disorder, memory or cognitive function disorder or impairment, extinction learning disorder, fungal disease or infection, inflammatory disease, hematological disease, or neoplastic disease, or for improving memory or treating, alleviating, or preventing memory loss or impairment.

11 Claims, No Drawings

INHIBITORS OF HISTONE DEACETYLASE

CROSS-REFERENCE TO RELATED APPLICATIONS

This application is a 35 U.S.C. §371 national stage filing of International Application No. PCT/US2015/037667, filed Jun. 25, 2015, which claims the benefit of U.S. Provisional Application No. 62/017,688, filed Jun. 26, 2014. Each of the aforementioned applications are incorporated herein by reference in their entirety.

BACKGROUND OF THE INVENTION

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. Nat Rev Cancer, 1, 194-202, (2001); and Marks, P. A., Richon, V. M., Miller, T., Kelly, W. K. Histone deacetylase inhibitors. Adv Cancer Res, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. Curr Drug Targets CNS Neurol Disord, 4, 41-50, (2005). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. Nat Neurosci, 9, 519-525, (2006).

There are 18 known human histone deacetylases, grouped into four classes based on the structure of their accessory domains. Class I includes HDAC1, HDAC2, HDAC3, and HDAC8 and has homology to yeast RPD3. HDAC4, HDAC5, HDAC7, and HDAC9 belong to class IIa and have homology to yeast. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

In contrast, HDACs have been shown to be powerful negative regulators of long-term memory processes. Nonspecific HDAC inhibitors enhance synaptic plasticity as well as long-term memory (Levenson et al., 2004, J. Biol. Chem. 279:40545-40559; Lattal et al., 2007, Behav Neurosci 121: 1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

Currently, the role of individual HDACs in long-term memory has been explored in two recent studies. Kilgore et al. 2010, Neuropsychopharmacology 35:870-880 revealed that nonspecific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. Indeed, forebrain and neuron specific over expression of HDAC2, but not HDAC1, decreased dendritic spine density, synaptic density, synaptic plasticity and memory formation. (Guan et al., 2009, Nature, 459:55-60). In contrast, HDAC2 knockout mice exhibited increased synaptic density, increased synaptic plasticity and increased dendritic density in neurons. These HDAC2 deficient mice also exhibited enhanced learning and memory in a battery of learning behavioral paradigms. This work demonstrates that HDAC2 is a key regulator of synaptogenesis and synaptic plasticity. Additionally, Guan et al. showed that chronic treatment of mice with SAHA (an HDAC 1, 2, 3, 6, 8 inhibitor) reproduced the effects seen in the HDAC2 deficient mice and recused the cognitive impairment in the HDAC2 overexpression mice.

Accordingly, the inhibition of the HDAC2 (selectively or in combination with inhibition of other class I HDACs) is an attractive therapeutic target. Such inhibition has the potential for enhancing cognition and facilitating the learning process through increasing synaptic and dendritic density in neuronal cell populations. In addition, inhibition of HDAC2 may also be therapeutically useful in treating a wide variety of other diseases and disorders.

DETAILED DESCRIPTION OF THE INVENTION

1. General Description of Certain Embodiments of the Invention

This invention provides compounds that are inhibitors of HDAC2. The compounds accordingly are useful for treating, alleviating, or preventing a condition in a subject such as a neurological disorder, memory or cognitive function disorder or impairment, extinction learning disorder, fungal disease or infection, inflammatory disease, hematological disease, or neoplastic disease, or for improving memory or treating, alleviating, or preventing memory loss or impairment.

In some embodiments the present invention provides a compound of formula I:

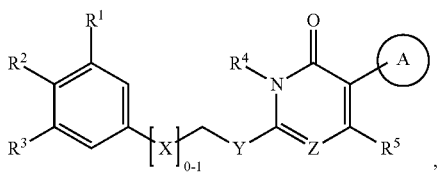

(I)

or a pharmaceutically acceptable salt thereof, wherein:
ring A is an optionally substituted carbocyclyl or optionally substituted aryl;
X, if present, is selected from oxazol-diyl, —C(=O)—, —CH(OH)—, and C(=NOH);
Y is selected from —O— and —S—;
Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;
each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—NH$_2$, —S(O)$_2$—($C_1$-$C_4$ alkyl), —$C_1$-$C_4$ alkyl, $C_1$-$C_4$ haloalkyl, —O—$C_1$-$C_4$ alkyl, and —O—$C_1$-$C_4$ haloalkyl, wherein:
each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or
two $R^6$ bound are taken together with the nitrogen atom to which they are bound to form an optionally substituted heterocyclyl or an optionally substituted heteroaryl; and
any alkyl portion of $R^1$, $R^2$, $R^3$ or $R^6$ is optionally substituted, or
any two of $R^1$, $R^2$ and $R^3$ are taken together to form an optionally substituted heterocyclyl, heteroaryl, carbocyclyl or aryl ring;
$R^4$ is selected from hydrogen, —CH(R')(R"), optionally substituted heterocyclyl, optionally substituted heteroaryl, optionally substituted aryl, and optionally substituted carbocyclyl, wherein:
each of R' and R" is independently selected from hydrogen, $C_1$-$C_6$ alkyl, $C_2$-$C_6$ alkenyl or alkynyl, —($C_0$-$C_6$ alkylene)-(optionally substituted carbocyclyl), —($C_0$-$C_6$ alkylene)-(optionally substituted aryl), —($C_0$-$C_6$ alkylene)-(optionally substituted heterocyclyl), and —($C_0$-$C_6$ alkylene)-(optionally substituted heteroaryl), —($C_2$-$C_6$ alkenylene or alkynylene)-(optionally substituted carbocyclyl), —($C_2$-$C_6$ alkenylene or alkynylene)-(optionally substituted aryl), —($C_2$-$C_6$ alkenylene or alkynylene)-(optionally substituted heterocyclyl), and —($C_2$-$C_6$ alkenylene or alkynylene)-(optionally substituted heteroaryl);
each alkyl, alkenyl, alkynyl, alkylene, alkenylene and alkynylene portion of R' and R" is optionally substituted; and
one or more methylene units of each alkyl, alkenyl, alkynyl, alkylene, alkenylene and alkynylene portion of R' and R" are optionally and independently replaced with —O—, —S—, —S(O)—, —S(O)$_2$, or —N($R^6$)—;
$R^5$ is selected from —OH, optionally substituted $C_1$-$C_4$ alkyl, optionally substituted $C_2$-$C_4$ alkenyl, and —O—C(O)-(optionally substituted $C_1$-$C_4$ alkyl).
In other embodiments, the invention features a compound having structural formula II:

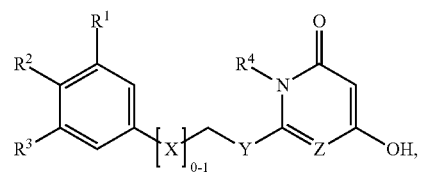

(II)

or a pharmaceutically acceptable salt thereof, wherein:
X, if present, is selected from oxazol-diyl, —C(=O)—, —CH(OH)—, and C(=NOH);
Y is selected from —O— and —S—;
Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;
each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:
each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or
two $R^6$ bound are taken together with the nitrogen atom to which they are bound to form an optionally substituted heterocyclyl or an optionally substituted heteroaryl; and,
any alkyl portion of $R^1$, $R^2$, $R^3$ or $R^6$ is optionally substituted;
any two of $R^1$, $R^2$ and $R^3$ are taken together to form an optionally substituted heterocyclyl, heteroaryl, carbocyclyl or aryl ring; and
$R^4$ is selected from methyl, ethyl, isopropyl and $C_2$-$C_3$ alkenyl.
In other embodiments, the invention features a compound having structural formula IIa:

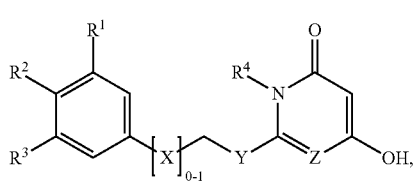

(IIa)

or a pharmaceutically acceptable salt thereof, wherein:
X, if present, is selected from oxazol-diyl, —C(=O)—, —CH(OH)—, and C(=NOH);

Y is selected from —O— and —S—;
Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;
each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:
each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or
two $R^6$ bound are taken together with the nitrogen atom to which they are bound to form an optionally substituted heterocyclyl or an optionally substituted heteroaryl; and
any alkyl portion of $R^1$, $R^2$, $R^3$ or $R^6$ is optionally substituted, or
any two of $R^1$, $R^2$ and $R^3$ are taken together to form an optionally substituted heterocyclyl, heteroaryl, carbocyclyl or aryl ring; and
$R^4$ is selected from methyl, ethyl, isopropyl and $C_2$-$C_3$ alkenyl.

In other embodiments, the invention features a compound having structural formula III:

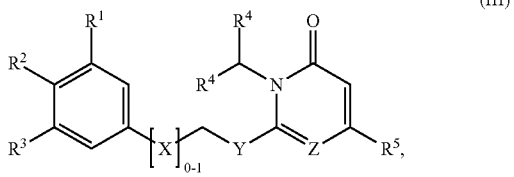

(III)

or a pharmaceutically acceptable salt thereof, wherein:
X, if present, is selected from oxazol-diyl, —C(=O)—, —CH(OH)—, and C(=NOH);
Y is selected from —O— and —S—;
Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;
each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:
each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or two $R^6$ bound are taken together with the nitrogen atom to which they are bound to form an optionally substituted heterocyclyl or an optionally substituted heteroaryl; and
any alkyl portion of $R^1$, $R^2$, $R^3$ or $R^6$ is optionally substituted, or
any two of $R^1$, $R^2$ and $R^3$ are taken together to form an optionally substituted heterocyclyl, heteroaryl, carbocyclyl or aryl ring;
$R^4$ is selected from hydrogen, —CH(R')(R"), optionally substituted heterocyclyl, optionally substituted heteroaryl, optionally substituted aryl, and optionally substituted carbocyclyl, wherein:
each of R' and R" is independently selected from hydrogen, $C_1$-$C_6$ alkyl, $C_2$-$C_6$ alkenyl or alkynyl, —($C_0$-$C_6$ alkylene)-(optionally substituted carbocyclyl), —($C_0$-$C_6$ alkylene)-(optionally substituted aryl), —($C_0$-$C_6$ alkylene)-(optionally substituted heterocyclyl), and —($C_0$-$C_6$ alkylene)-(optionally substituted heteroaryl), —($C_2$-$C_6$ alkenylene or alkynylene)-(optionally substituted carbocyclyl), —($C_2$-$C_6$ alkenylene or alkynylene)-(optionally substituted aryl), —($C_2$-$C_6$ alkenylene or alkynylene)-(optionally substituted heterocyclyl), and —($C_2$-$C_6$ alkenylene or alkynylene)-(optionally substituted heteroaryl);
each alkyl, alkenyl, alkynyl, alkylene, alkenylene and alkynylene portion of R' and R" is optionally substituted and;
one or more methylene units of each alkyl, alkenyl, alkynyl, alkylene, alkenylene and alkynylene portion of R' and R" are optionally and independently replaced with —O—, —S—, —S(O)—, —S(O)$_2$, or —N($R^6$)—, or
two $R^4$ are taken together to form an optionally substituted carbocyclyl, an optionally substituted aryl, an optionally substituted heterocyclyl, or an optionally substituted heteroaryl; and
$R^5$ is selected from optionally substituted $C_1$-$C_4$ alkyl, optionally substituted $C_2$-$C_4$ alkenyl, and —O—C(O)-(optionally substituted $C_1$-$C_4$ alkyl), and
(b) a pharmaceutically acceptable carrier.

In other embodiments, the invention features a compound having structural formula IV:

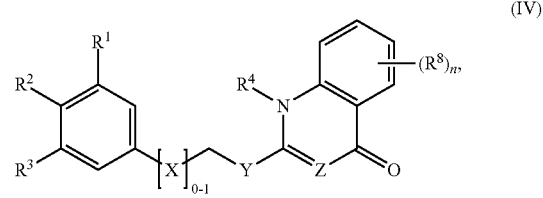

(IV)

or a pharmaceutically acceptable salt thereof, wherein:
X, if present, is selected from oxazol-diyl, —C(=O)—, —CH(OH)—, and C(=NOH);
Y is selected from —O— and —S—;
Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;
each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—

—(C$_1$-C$_4$ alkyl)$_2$, —S(O)$_2$—NH—(C$_1$-C$_4$ alkyl), —S(O)$_2$—(C$_1$-C$_4$ alkyl), —S(O)$_2$—NH$_2$, —C$_1$-C$_4$ alkyl, C$_1$-C$_4$ haloalkyl, —O—C$_1$-C$_4$ alkyl, and —O—C$_1$-C$_4$ haloalkyl, wherein:

each R$^6$ is independently selected from hydrogen, —C$_1$-C$_4$ alkyl, —C(O)—C$_1$-C$_4$ alkyl, —C(O)-carbocyclyl, —C(O)-heterocyclyl, —C(O)-aryl, —C(O)-heteroaryl, —C(O)—O—C$_1$-C$_4$ alkyl, —C(O)—N—(C$_1$-C$_4$ alkyl)$_2$, —C(O)—NH—(C$_1$-C$_4$ alkyl), —C(O)—NH$_2$, and —S(O)$_2$—C$_1$-C$_4$ alkyl, or two R$^6$ bound are taken together with the nitrogen atom to which they are bound to form an optionally substituted heterocyclyl or an optionally substituted heteroaryl; and any alkyl portion of R$^1$, R$^2$, R$^3$ or R$^6$ is optionally substituted, or any two of R$^1$, R$^2$ and R$^3$ are taken together to form an optionally substituted heterocyclyl, heteroaryl, carbocyclyl or aryl ring;

R$^4$ is selected from —C$_1$-C$_4$ alkyl and —C$_2$-C$_4$ alkenyl;

R$^8$, if present, is selected from halogen, optionally substituted —C1-C4-alkyl, optionally substituted —O—C$_1$-C$_4$ alkyl, or any two R$^8$ are taken together with the atoms to which they are bound to form an optionally substituted heterocyclyl or optionally substituted heteroaryl; and n is 0, 1, 2, 3, 4, or 5.

In other embodiments, the invention features a compound having structural formula V:

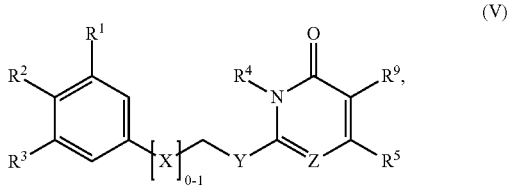

(V)

or a pharmaceutically acceptable salt thereof, wherein:

X, if present, is selected from oxazol-diyl, —C(=O)—, —CH(OH)—, and C(=NOH);

Y is selected from —O— and —S—;

Z is selected from N and C(R$^7$), wherein R$^7$ is selected from hydrogen, halogen, C$_1$-C$_4$ alkyl and —O—C$_1$-C$_4$ alkyl, wherein the alkyl portion of R$^7$ is optionally substituted;

each of R$^1$, R$^2$ and R$^3$ is independently selected from hydrogen, halo, optionally substituted heterocyclyl, —N(R$^6$)$_2$, —C(O)—N—(C$_1$-C$_4$ alkyl)$_2$, —C(O)—NH—(C$_1$-C$_4$ alkyl), —C(O)—NH$_2$, —S(O)$_2$—N—(C$_1$-C$_4$ alkyl)$_2$, —S(O)$_2$—NH—(C$_1$-C$_4$ alkyl), —S(O)$_2$—(C$_1$-C$_4$ alkyl), —S(O)$_2$—NH$_2$, —C$_1$-C$_4$ alkyl, C$_1$-C$_4$ haloalkyl, —O—C$_1$-C$_4$ alkyl, and —O—C$_1$-C$_4$ haloalkyl, wherein:

each R$^6$ is independently selected from hydrogen, —C$_1$-C$_4$ alkyl, —C(O)—C$_1$-C$_4$alkyl, —C(O)-carbocyclyl, —C(O)-heterocyclyl, —C(O)-aryl, —C(O)-heteroaryl, —C(O)—O—C$_1$-C$_4$ alkyl, —C(O)—N—(C$_1$-C$_4$ alkyl)$_2$, —C(O)—NH—(C$_1$-C$_4$ alkyl), —C(O)—NH$_2$, and —S(O)$_2$—C$_1$-C$_4$ alkyl, or two R$^6$ bound are taken together with the nitrogen atom to which they are bound to form an optionally substituted heterocyclyl or an optionally substituted heteroaryl; and any alkyl portion of R$^1$, R$^2$, R$^3$ or R$^6$ is optionally substituted, or any two of R$^1$, R$^2$ and R$^3$ are taken together to form an optionally substituted heterocyclyl, heteroaryl, carbocyclyl or aryl ring;

R$^4$ is selected from hydrogen, —CH(R')(R"), optionally substituted heterocyclyl, optionally substituted heteroaryl, optionally substituted aryl, and optionally substituted carbocyclyl, wherein:

each of R' and R" is independently selected from hydrogen, C$_1$-C$_6$ alkyl, C$_2$-C$_6$ alkenyl or alkynyl, —(C$_0$-C$_6$ alkylene)-(optionally substituted carbocyclyl), —(C$_0$-C$_6$ alkylene)-(optionally substituted aryl), —(C$_0$-C$_6$ alkylene)-(optionally substituted heterocyclyl), and —(C$_0$-C$_6$ alkylene)-(optionally substituted heteroaryl), —(C$_2$-C$_6$ alkenylene or alkynylene)-(optionally substituted carbocyclyl), —(C$_2$-C$_6$ alkenylene or alkynylene)-(optionally substituted aryl), —(C$_2$-C$_6$ alkenylene or alkynylene)-(optionally substituted heterocyclyl), and —(C$_2$-C$_6$ alkenylene or alkynylene)-(optionally substituted heteroaryl);

each alkyl, alkenyl, alkynyl, alkylene, alkenylene and alkynylene portion of R' and R" is optionally substituted and;

one or more methylene units of each alkyl, alkenyl, alkynyl, alkylene, alkenylene and alkynylene portion of R' and R" are optionally and independently replaced with —O—, —S—, —S(O)—, —S(O)$_2$, or —N(R$^6$)—;

R$^5$ is selected from —OH, optionally substituted C$_1$-C$_4$ alkyl and optionally substituted C$_2$-C$_4$ alkenyl; and R$^9$ is selected from hydrogen, optionally substituted C$_1$-C$_4$ alkyl, optionally substituted carbocyclyl or optionally substituted aryl; or R$^5$ and R$^9$ are optionally taken together with the atoms to which they are bound to form an optionally substituted heterocyclyl or an optionally substituted heteroaryl.

In other embodiments, the invention features a compound having structural formula VI:

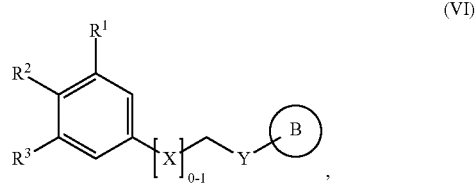

(VI)

or a pharmaceutically acceptable salt thereof, wherein:

Ring B is selected from:

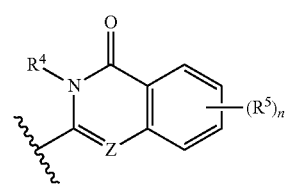

and

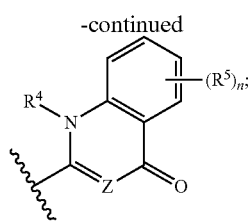

X, if present, is selected from oxazol-diyl, —C(═O)—, —CH(OH)—, and C(═NOH);

Y is selected from —O— and —S—;

Z is selected from N and C(R$^7$), wherein R$^7$ is selected from hydrogen, halogen, C$_1$-C$_4$ alkyl and —O—C$_1$-C$_4$ alkyl, wherein the alkyl portion of R$^7$ is optionally substituted;

each of R$^1$, R$^2$ and R$^3$ is independently selected from hydrogen, halo, optionally substituted heterocyclyl, —N(R$^6$)$_2$, —C(O)—N—(C$_1$-C$_4$ alkyl)$_2$, —C(O)—NH—(C$_1$-C$_4$ alkyl), —C(O)—NH$_2$, —S(O)$_2$—N—(C$_1$-C$_4$ alkyl)$_2$, —S(O)$_2$—NH—(C$_1$-C$_4$ alkyl), —S(O)$_2$—(C$_1$-C$_4$ alkyl), —S(O)$_2$—NH$_2$, —C$_1$-C$_4$ alkyl, C$_1$-C$_4$ haloalkyl, —O—C$_1$-C$_4$ alkyl, and —O—C$_1$-C$_4$ haloalkyl, wherein:

each R$^6$ is independently selected from hydrogen, —C$_1$-C$_4$ alkyl, —C(O)—C$_1$-C$_4$ alkyl, —C(O)-carbocyclyl, —C(O)-heterocyclyl, —C(O)-aryl, —C(O)-heteroaryl, —C(O)—O—C$_1$-C$_4$ alkyl, —C(O)—N—(C$_1$-C$_4$ alkyl)$_2$, —C(O)—NH—(C$_1$-C$_4$ alkyl), —C(O)—NH$_2$, and —S(O)$_2$—C$_1$-C$_4$ alkyl, or two R$^6$ bound are taken together with the nitrogen atom to which they are bound to form an optionally substituted heterocyclyl or an optionally substituted heteroaryl; and any alkyl portion of R$^1$, R$^2$, R$^3$ or R$^6$ is optionally substituted, or any two of R$^1$, R$^2$ and R$^3$ are taken together to form an optionally substituted heterocyclyl, heteroaryl, carbocyclyl or aryl ring;

R$^4$ is selected from hydrogen, —CH(R')(R"), optionally substituted heterocyclyl, optionally substituted heteroaryl, optionally substituted aryl, and optionally substituted carbocyclyl, wherein:

each of R' and R" is independently selected from hydrogen, C$_1$-C$_6$ alkyl, C$_2$-C$_6$ alkenyl or alkynyl, —(C$_0$-C$_6$ alkylene)-(optionally substituted carbocyclyl), —(C$_0$-C$_6$ alkylene)-(optionally substituted aryl), —(C$_0$-C$_6$ alkylene)-(optionally substituted heterocyclyl), and —(C$_0$-C$_6$ alkylene)-(optionally substituted heteroaryl), —(C$_2$-C$_6$ alkenylene or alkynylene)-(optionally substituted carbocyclyl), —(C$_2$-C$_6$ alkenylene or alkynylene)-(optionally substituted aryl), —(C$_2$-C$_6$ alkenylene or alkynylene)-(optionally substituted heterocyclyl), and —(C$_2$-C$_6$ alkenylene or alkynylene)-(optionally substituted heteroaryl);

each alkyl, alkenyl, alkynyl, alkylene, alkenylene and alkynylene portion of R' and R" is optionally substituted and;

one or more methylene units of each alkyl, alkenyl, alkynyl, alkylene, alkenylene and alkynylene portion of R' and R" are optionally and independently replaced with —O—, —S—, —S(O)—, —S(O)$_2$, or —N(R$^6$)—;

R$^5$ is selected from halogen, C$_1$-C$_4$ alkyl and —O—C$_1$-C$_4$ alkyl, wherein the alkyl portion of R$^5$ is optionally substituted, or two R$^5$ are taken together with the atoms to which they are bound to form an optionally substituted heterocyclyl; and n is 0, 1, 2, 3, or 4.

2. Compounds and Definitions

Compounds of this invention include those described generally for formula I, above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched C$_{1-12}$ hydrocarbon which is completely saturated or which contains one or more units of unsaturation. For example, suitable aliphatic groups include optionally substituted linear or branched alkyl, alkenyl, alkynyl, alkylene, alkenylene, and alkynylene groups. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms, and which is not aromatic. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I.

The term "heteroatom" refers to one or more of oxygen, sulfur, nitrogen, phosphorus, and silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. Preferably, the aryl group is a $C_{6-10}$aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, and/or heterocyclic rings. Non-limiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl and/or carbocyclic rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkenyl group. A substituted alkynylene chain is a polymethylene group containing at least one triple bond in which one or more hydrogen atoms are replaced with a substituent. Suitable substituents include those described below for a substituted aliphatic group.

An alkylene, alkenyl, or alkynyl chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, and unless otherwise stated, all bivalent groups described herein, including, e.g., the alkylene, alkenyl, and alkynyl chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$), —C(R$^o$)=N—OR$^+$, —P(O)(R$^+$)$_2$, —P(O)(OR)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$=N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

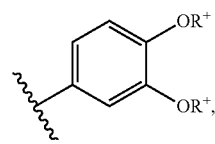

these two occurrences of R+ are taken together with the oxygen atoms to which they are bound to form a fused 6-membered oxygen containing ring:

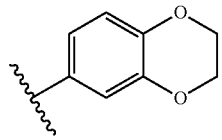

It will be appreciated that a variety of other rings (e.g., spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays. Additionally, in the case of deuterium substitution, the resulting compounds are useful as therapeutic compounds that may display altered metabolism and/or altered rates of racemization (for isomeric compounds) as compared to their protio counterparts.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

As described generally above, in some embodiments the present invention provides a compound of formula I:

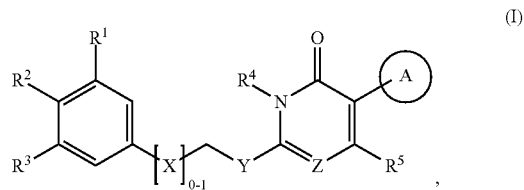

or a pharmaceutically acceptable salt thereof, wherein:
ring A is an optionally substituted carbocyclyl or optionally substituted aryl;
X, if present, is selected from oxazol-diyl, —C(=O)—, —CH(OH)—, and C(=NOH);
Y is selected from —O— and —S—;
Z is selected from N and C(R$^7$), wherein R$^7$ is selected from hydrogen, halogen, C$_1$-C$_4$ alkyl and —O—C$_1$-C$_4$ alkyl, wherein the alkyl portion of R$^7$ is optionally substituted;
each of R$^1$, R$^2$ and R$^3$ is independently selected from hydrogen, halo, optionally substituted heterocyclyl, —N(R$^6$)$_2$, —C(O)—N—(C$_1$-C$_4$ alkyl)$_2$, —C(O)—NH—(C$_1$-C$_4$ alkyl), —C(O)—NH$_2$, —S(O)$_2$—N—(C$_1$-C$_4$ alkyl)$_2$, —S(O)$_2$—NH—(C$_1$-C$_4$ alkyl), —S(O)$_2$—NH$_2$, —S(O)$_2$—(C$_1$-C$_4$ alkyl), —C$_1$-C$_4$ alkyl, C$_1$-C$_4$ haloalkyl, —O—C$_1$-C$_4$ alkyl, and —O—C$_1$-C$_4$ haloalkyl, wherein:
each R$^6$ is independently selected from hydrogen, —C$_1$-C$_4$ alkyl, —C(O)—C$_1$-C$_4$ alkyl, —C(O)-carbocyclyl, —C(O)-heterocyclyl, —C(O)-aryl, —C(O)-heteroaryl, —C(O)—O—C$_1$-C$_4$ alkyl, —C(O)—N—(C$_1$-C$_4$ alkyl)$_2$, —C(O)—NH—(C$_1$-C$_4$ alkyl), —C(O)—NH$_2$, and —S(O)$_2$—C$_1$-C$_4$ alkyl, or two R$^6$ bound are taken together with the nitrogen atom to which they are bound to form an optionally substituted heterocyclyl or an optionally substituted heteroaryl; and any alkyl portion of R$^1$, R$^2$, R$^3$ or R$^6$ is optionally substituted, or any two of R$^1$, R$^2$ and R$^3$ are taken together to form an optionally substituted heterocyclyl, heteroaryl, carbocyclyl or aryl ring;

R$^4$ is selected from hydrogen, —CH(R')(R"), optionally substituted heterocyclyl, optionally substituted heteroaryl, optionally substituted aryl, and optionally substituted carbocyclyl, wherein:

each of R' and R" is independently selected from hydrogen, C$_1$-C$_6$ alkyl, C$_2$-C$_6$ alkenyl or alkynyl, —(C$_0$-C$_6$ alkylene)-(optionally substituted carbocyclyl), —(C$_0$-C$_6$ alkylene)-(optionally substituted aryl), —(C$_0$-C$_6$ alkylene)-(optionally substituted heterocyclyl), and —(C$_0$-C$_6$ alkylene)-(optionally substituted heteroaryl), —(C$_2$-C$_6$ alkenylene or alkynylene)-(optionally substituted carbocyclyl), —(C$_2$-C$_6$ alkenylene or alkynylene)-(optionally substituted aryl), —(C$_2$-C$_6$ alkenylene or alkynylene)-(optionally substituted heterocyclyl), and —(C$_2$-C$_6$ alkenylene or alkynylene)-(optionally substituted heteroaryl);

each alkyl, alkenyl, alkynyl, alkylene, alkenylene and alkynylene portion of R' and R" is optionally substituted; and one or more methylene units of each alkyl, alkenyl, alkynyl, alkylene, alkenylene and alkynylene portion of R' and R" are optionally and independently replaced with —O—, —S—, —S(O)—, —S(O)$_2$, or —N(R$^6$)—;

R$^5$ is selected from —OH, optionally substituted C$_1$-C$_4$ alkyl, optionally substituted C$_2$-C$_4$ alkenyl, and —O—C(O)-(optionally substituted C$_1$-C$_4$ alkyl).

In some embodiments, when X is absent, Y is S; Z is N and R2 is halo or hydrogen, ring A is other than unsubstituted phenyl unsubstituted cyclohexyl, or unsubstituted cyclopentyl.

In some embodiments, when X is —C(O)—, Y is S; Z is N and R2 is halo, methoxy, methyl or hydrogen, ring A is other than unsubstituted phenyl.

In some embodiments, the compound of formula (I) is other than

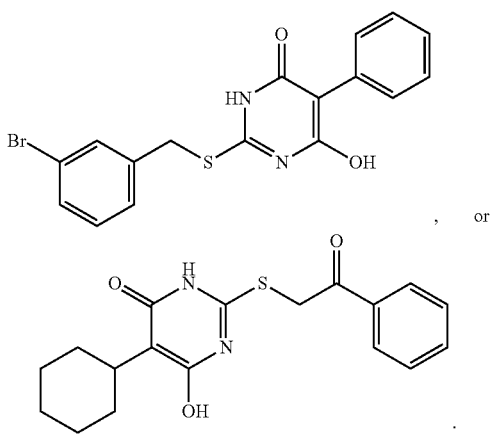

In some embodiments, R$^1$ is hydrogen.

In some embodiments, R$^2$ is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, R$^3$ is selected from hydrogen, fluoro, chloro and methyl.

In other embodiments, R$^2$ and R$^3$ are taken together to form 1H-benzo[d]imidazol-5-yl In some embodiments, X is C(O).

In some embodiments, Y is S.

In some embodiments, R$^4$ is selected from hydrogen, C$_1$-C$_4$ alkyl, C$_2$-C$_4$ alkenyl, C$_3$-C$_6$ cycloalkyl, and phenyl.

In some embodiments, R$^4$ is selected from hydrogen, methyl, ethyl, isopropyl, 1-propenyl, cyclopropyl, cyclopentyl and phenyl.

In some embodiments, R$^5$ is selected from hydrogen, hydroxy, methyl and ethyl.

In some embodiments, Z is N.

In some embodiments, ring A is phenyl or cyclopentyl.

In other embodiments, the invention features a compound having structural formula II:

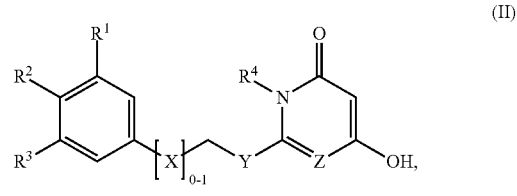

(II)

or a pharmaceutically acceptable salt thereof, wherein:

X, if present, is selected from oxazol-diyl, —C(=O)—, —CH(OH)—, and C(=NOH);

Y is selected from —O— and —S—;

Z is selected from N and C(R$^7$), wherein R$^7$ is selected from hydrogen, halogen, C$_1$-C$_4$ alkyl and —O—C$_1$-C$_4$ alkyl, wherein the alkyl portion of R$^7$ is optionally substituted;

each of R$^1$, R$^2$ and R$^3$ is independently selected from hydrogen, halo, optionally substituted heterocyclyl, —N(R$^6$)$_2$, —C(O)—N—(C$_1$-C$_4$ alkyl)$_2$, —C(O)—NH—(C$_1$-C$_4$ alkyl), —C(O)—NH$_2$, —S(O)$_2$—N—(C$_1$-C$_4$ alkyl)$_2$, —S(O)$_2$—NH—(C$_1$-C$_4$ alkyl), —S(O)$_2$—(C$_1$-C$_4$ alkyl), —S(O)$_2$—NH$_2$, —C$_1$-C$_4$ alkyl, C$_1$-C$_4$ haloalkyl, —O—C$_1$-C$_4$ alkyl, and —O—C$_1$-C$_4$ haloalkyl, wherein:

each R$^6$ is independently selected from hydrogen, —C$_1$-C$_4$ alkyl, —C(O)—C$_1$-C$_4$ alkyl, —C(O)-carbocyclyl, —C(O)-heterocyclyl, —C(O)-aryl, —C(O)-heteroaryl, —C(O)—O—C$_1$-C$_4$ alkyl, —C(O)—N—(C$_1$-C$_4$ alkyl)$_2$, —C(O)—NH—(C$_1$-C$_4$ alkyl), —C(O)—NH$_2$, and —S(O)$_2$—C$_1$-C$_4$ alkyl, or two R$^6$ bound are taken together with the nitrogen atom to which they are bound to form an optionally substituted heterocyclyl or an optionally substituted heteroaryl; and, any alkyl portion of R$^1$, R$^2$, R$^3$ or R$^6$ is optionally substituted;

any two of R$^1$, R$^2$ and R$^3$ are taken together to form an optionally substituted heterocyclyl, heteroaryl, carbocyclyl or aryl ring; and R[4] is selected from methyl, ethyl, isopropyl and $C_2$-$C_3$ alkenyl.

In some embodiments, at least one of R[1], R[2] or R[3] is other than hydrogen.

In some embodiments, the compound is other than:

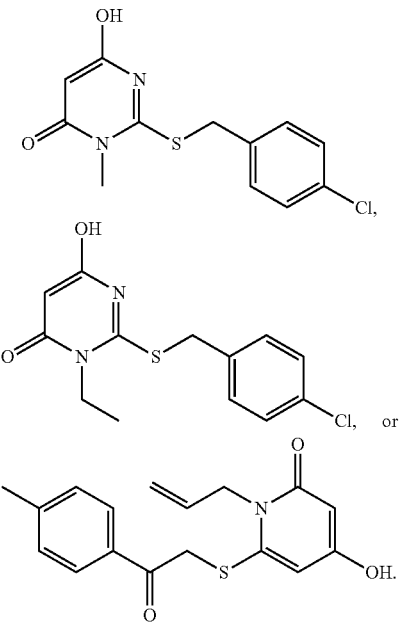

In some embodiments, R[1] is hydrogen.

In some embodiments, R[2] is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, R[3] is selected from hydrogen, fluoro, chloro and methyl.

In other embodiments, R[2] and R[3] are taken together to form 1H-benzo[d]imidazol-5-yl.

In some embodiments, X is C(O).

In some embodiments, Y is S.

In some embodiments, Z is N.

In other embodiments, the invention features a compound having structural formula IIa:

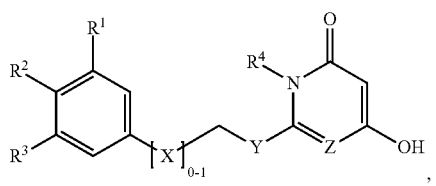
(IIa)

or a pharmaceutically acceptable salt thereof; wherein:

X, if present, is selected from oxazol-diyl, —C(=O)—, —CH(OH)—, and C(=NOH);

Y is selected from —O— and —S—;

Z is selected from N and C(R[7]), wherein R[7] is selected from hydrogen, halogen, $C_1$-$C_4$ alkyl and —O—$C_1$-$C_4$ alkyl, wherein the alkyl portion of R[7] is optionally substituted;

each of R[1], R[2] and R[3] is independently selected from hydrogen, halo, optionally substituted heterocyclyl, —N(R[6])$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$, —($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:

each R[6] is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or two R[6] bound are taken together with the nitrogen atom to which they are bound to form an optionally substituted heterocyclyl or an optionally substituted heteroaryl; and any alkyl portion of R[1], R[2], R[3] or R[6] is optionally substituted, or any two of R[1], R[2] and R[3] are taken together to form an optionally substituted heterocyclyl, heteroaryl, carbocyclyl or aryl ring; and R[4] is selected from methyl, ethyl, isopropyl and $C_2$-$C_3$ alkenyl.

In some embodiments, R[1] is hydrogen.

In some embodiments, R[2] is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, R[3] is selected from hydrogen, fluoro, chloro and methyl.

In some embodiments, R[2] and R[3] are taken together to form 1H-benzo[d]imidazol-5-yl.

In some embodiments, X is C(O).

In some embodiments, Y is S.

In some embodiments, Z is N.

In other embodiments, the invention features a compound having structural formula III:

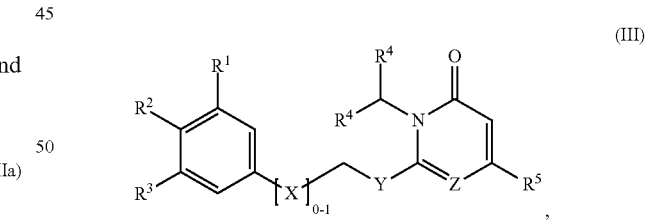
(III)

or a pharmaceutically acceptable salt thereof, wherein:

X, if present, is selected from oxazol-diyl, —C(=O)—, —CH(OH)—, and C(=NOH);

Y is selected from —O— and —S—;

Z is selected from N and C(R[7]), wherein R[7] is selected from hydrogen, halogen, $C_1$-$C_4$ alkyl and —O—$C_1$-$C_4$ alkyl, wherein the alkyl portion of R[7] is optionally substituted;

each of R[1], R[2] and R[3] is independently selected from hydrogen, halo, optionally substituted heterocyclyl, —N(R[6])$_2$, —C(O)—N—($C_1$-$C_4$ alkyl)$_2$, —C(O)—NH—($C_1$-$C_4$ alkyl), —C(O)—NH$_2$, —S(O)$_2$—N—

($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:

each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or two $R^6$ bound are taken together with the nitrogen atom to which they are bound to form an optionally substituted heterocyclyl or an optionally substituted heteroaryl; and any alkyl portion of $R^1$, $R^2$, $R^3$ or $R^6$ is optionally substituted, or any two of $R^1$, $R^2$ and $R^3$ are taken together to form an optionally substituted heterocyclyl, heteroaryl, carbocyclyl or aryl ring;

$R^4$ is selected from hydrogen, —CH(R')(R"), optionally substituted heterocyclyl, optionally substituted heteroaryl, optionally substituted aryl, and optionally substituted carbocyclyl, wherein:

each of R' and R" is independently selected from hydrogen, $C_1$-$C_6$ alkyl, $C_2$-$C_6$ alkenyl or alkynyl, —($C_0$-$C_6$ alkylene)-(optionally substituted carbocyclyl), —($C_0$-$C_6$ alkylene)-(optionally substituted aryl), —($C_0$-$C_6$ alkylene)-(optionally substituted heterocyclyl), and —($C_0$-$C_6$ alkylene)-(optionally substituted heteroaryl), —($C_2$-$C_6$ alkenylene or alkynylene)-(optionally substituted carbocyclyl), —($C_2$-$C_6$ alkenylene or alkynylene)-(optionally substituted aryl), —($C_2$-$C_6$ alkenylene or alkynylene)-(optionally substituted heterocyclyl), and —($C_2$-$C_6$ alkenylene or alkynylene)-(optionally substituted heteroaryl);

each alkyl, alkenyl, alkynyl, alkylene, alkenylene and alkynylene portion of R' and R" is optionally substituted and;

one or more methylene units of each alkyl, alkenyl, alkynyl, alkylene, alkenylene and alkynylene portion of R' and R" are optionally and independently replaced with —O—, —S—, —S(O)—, —S(O)$_2$, or —N($R^6$)—, or two $R^4$ are taken together to form an optionally substituted carbocyclyl, an optionally substituted aryl, an optionally substituted heterocyclyl, or an optionally substituted heteroaryl; and $R^5$ is selected from optionally substituted $C_1$-$C_4$ alkyl, optionally substituted $C_2$-$C_4$ alkenyl, and —O—C(O)-(optionally substituted $C_1$-$C_4$ alkyl), and (b) a pharmaceutically acceptable carrier.

In some embodiments, $R^1$ is hydrogen.

In some embodiments, $R^2$ is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, $R^3$ is selected from hydrogen, fluoro, chloro and methyl.

In some embodiments, $R^2$ and $R^3$ are taken together to form 1H-benzo[d]imidazol-5-yl In some embodiments, X is C(O).

In some embodiments, Y is S.

In some embodiments, $R^4$ is selected from hydrogen, $C_1$-$C_4$ alkyl, —CH$_2$—($C_2$-$C_3$ alkenyl), $C_3$-$C_6$ cycloalkyl, and phenyl.

In some embodiments, $R^4$ is selected from hydrogen, methyl, ethyl, isopropyl, 1-propenyl, cyclopropyl, cyclopentyl and phenyl.

In some embodiments, $R^5$ is selected from hydrogen, methyl and ethyl.

In some embodiments, Z is N.

In other embodiments, the invention features a compound having structural formula IV:

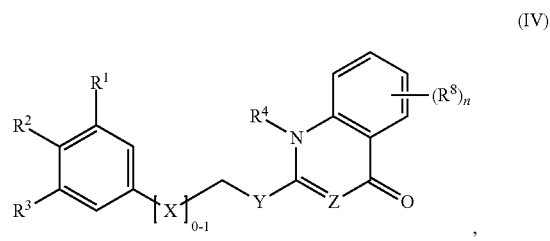

(IV)

or a pharmaceutically acceptable salt thereof, wherein:

X, if present, is selected from oxazol-diyl, —C(=O)—, —CH(OH)—, and C(=NOH);

Y is selected from —O— and —S—;

Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;

each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:

each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or two $R^6$ bound are taken together with the nitrogen atom to which they are bound to form an optionally substituted heterocyclyl or an optionally substituted heteroaryl; and any alkyl portion of $R^1$, $R^2$, $R^3$ or $R^6$ is optionally substituted, or any two of $R^2$ and $R^3$ are taken together to form an optionally substituted heterocyclyl, heteroaryl, carbocyclyl or aryl ring;

$R^4$ is selected from —$C_1$-$C_4$ alkyl and —$C_2$-$C_4$ alkenyl;

$R^8$, if present, is selected from halogen, optionally substituted —C1-C4-alkyl, optionally substituted —O—$C_1$-$C_4$ alkyl, or any two $R^8$ are taken together with the atoms to which they are bound to form an optionally substituted heterocyclyl or optionally substituted heteroaryl; and n is 0, 1, 2, 3, 4, or 5.

In some embodiments, the compound is other than:

[Chemical structures shown]

, or

.

In some embodiments, $R^1$ is hydrogen.

In some embodiments, $R^2$ is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, $R^3$ is selected from hydrogen, fluoro, chloro and methyl.

In some embodiments, $R^2$ and $R^3$ are taken together to form 1H-benzo[d]imidazol-5-yl.

In some embodiments, X is C(O).

In some embodiments, Y is S.

In some embodiments, $R^4$ is selected from methyl, ethyl, isopropyl, and 1-propenyl.

In some embodiments, Z is N.

In some embodiments, n is 0.

In other embodiments, the invention features a compound having structural formula V:

[Chemical structure V shown]

(V)

or a pharmaceutically acceptable salt thereof, wherein:
 X, if present, is selected from oxazol-diyl, —C(=O)—, —CH(OH)—, and C(=NOH);
 Y is selected from —O— and —S—;
 Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;

each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:
 each $R^6$ is independently selected from hydrogen, —$C_1$-$C_4$ alkyl, —C(O)—$C_1$-$C_4$alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or
 two $R^6$ bound are taken together with the nitrogen atom to which they are bound to form an optionally substituted heterocyclyl or an optionally substituted heteroaryl; and
 any alkyl portion of $R^1$, $R^2$, $R^3$ or $R^6$ is optionally substituted, or
 any two of $R^1$, $R^2$ and $R^3$ are taken together to form an optionally substituted heterocyclyl, heteroaryl, carbocyclyl or aryl ring;
$R^4$ is selected from hydrogen, —CH(R')(R''), optionally substituted heterocyclyl, optionally substituted heteroaryl, optionally substituted aryl, and optionally substituted carbocyclyl, wherein:
 each of R' and R'' is independently selected from hydrogen, $C_1$-$C_6$ alkyl, $C_2$-$C_6$ alkenyl or alkynyl, —($C_0$-$C_6$ alkylene)-(optionally substituted carbocyclyl), —($C_0$-$C_6$ alkylene)-(optionally substituted aryl), —($C_0$-$C_6$ alkylene)-(optionally substituted heterocyclyl), and —($C_0$-$C_6$ alkylene)-(optionally substituted heteroaryl), —($C_2$-$C_6$ alkenylene or alkynylene)-(optionally substituted carbocyclyl), —($C_2$-$C_6$ alkenylene or alkynylene)-(optionally substituted aryl), —($C_2$-$C_6$ alkenylene or alkynylene)-(optionally substituted heterocyclyl), and —($C_2$-$C_6$ alkenylene or alkynylene)-(optionally substituted heteroaryl);
 each alkyl, alkenyl, alkynyl, alkylene, alkenylene and alkynylene portion of R' and R'' is optionally substituted and;
 one or more methylene units of each alkyl, alkenyl, alkynyl, alkylene, alkenylene and alkynylene portion of R' and R'' are optionally and independently replaced with —O—, —S—, —S(O)—, —S(O)$_2$, or —N($R^6$)—;
$R^5$ is selected from —OH, optionally substituted $C_1$-$C_4$ alkyl and optionally substituted $C_2$-$C_4$ alkenyl; and
$R^9$ is selected from hydrogen, optionally substituted $C_1$-$C_4$ alkyl, optionally substituted carbocyclyl or optionally substituted aryl; or
$R^5$ and $R^9$ are optionally taken together with the atoms to which they are bound to form an optionally substituted heterocyclyl or an optionally substituted heteroaryl.

In some embodiments, when $R^1$, $R^3$, $R^4$ and $R^6$ are simultaneously hydrogen, X is —C(O)—, Y is S, Z is N, and $R^5$ is methyl, then $R^2$ is other than chloro, hydrogen, hydroxy, methoxy, acetamido, N-methylacetamido, t-butyl, phenylamido.

In some embodiments, when $R^1$, $R^3$, $R^4$ and $R^6$ are simultaneously hydrogen, X is —C(O)—, Y is O, and $R^5$ is methyl, then $R^2$ is other than acetamido.

In some embodiments, when $R^1$, $R^3$, $R^4$ and $R^6$ are simultaneously hydrogen, X is —C(O)—, Y is S, and $R^5$ is hydroxy, then $R^2$ is other than hydrogen or methoxy.

In some embodiments, the compound is other than:

[Structure: N-(4-((6-methyl-4-oxo-1,4-dihydropyrimidin-2-ylthio)methyl)phenyl)acetamide]

[Structure: 2-((3,4-dihydroxyphenyl)carbonylmethylthio)-6-methyl-pyrimidin-4(3H)-one related compound]

[Structure: 6-methyl-2-((2-oxoindolin-6-yl)carbonylmethylthio)pyrimidin-4(3H)-one related compound]

, or

[Structure: 2-((2,3-dihydrobenzo[b][1,4]dioxin-6-yl)carbonylmethylthio)-6-methylpyrimidin-4(3H)-one]

.

In some embodiments, $R^1$ is hydrogen.

In some embodiments, $R^2$ is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, $R^3$ is selected from hydrogen, fluoro, chloro and methyl.

In some embodiments, $R^2$ and $R^3$ are taken together to form 1H-benzo[d]imidazol-5-yl In some embodiments, X is C(O).

In some embodiments, Y is S.

In some embodiments, $R^4$ is selected from hydrogen, $C_1$-$C_4$ alkyl, $C_2$-$C_4$ alkenyl, $C_3$-$C_6$ cycloalkyl, and phenyl.

In some embodiments, R4 is selected from hydrogen, methyl, ethyl, isopropyl, 1-propenyl, cyclopropyl, cyclopentyl and phenyl.

In some embodiments, $R^5$ is selected from hydrogen, hydroxy, methyl and ethyl.

In some embodiments, Z is N.

In some embodiments, $R^9$ is selected from hydrogen, phenyl, benzyl and cyclopentyl.

In other embodiments, the invention features a compound having structural formula VI:

[Structure VI]

(VI)

or a pharmaceutically acceptable salt thereof, wherein:
Ring B is selected from:

[Structure with $R^4$, N, Z, $(R^5)_n$]

and

[Structure with $R^4$, N, Z, $(R^5)_n$]

;

X, if present, is selected from oxazol-diyl, —C(=O)—, —CH(OH)—, and C(=NOH);

Y is selected from —O— and —S—;

Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;

each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—($C_1$-$C_4$ alkyl), —S(O)$_2$—NH$_2$, —$C_1$-$C_4$ alkyl, $C_1$-$C_4$ haloalkyl, —O—$C_1$-$C_4$ alkyl, and —O—$C_1$-$C_4$ haloalkyl, wherein:

each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or two $R^6$ bound are taken together with the nitrogen atom to which they are bound to form an optionally substituted heterocyclyl or an optionally substituted heteroaryl; and any alkyl portion of $R^1$, $R^2$, $R^3$ or $R^6$ is optionally substituted, or any two of $R^1$, $R^2$ and $R^3$ are taken together to form an optionally substituted heterocyclyl, heteroaryl, carbocyclyl or aryl ring;

$R^4$ is selected from hydrogen, —CH(R')(R"), optionally substituted heterocyclyl, optionally substituted heteroaryl, optionally substituted aryl, and optionally substituted carbocyclyl, wherein:

each of R' and R" is independently selected from hydrogen, $C_1$-$C_6$ alkyl, $C_2$-$C_6$ alkenyl or alkynyl, —($C_0$-$C_6$ alkylene)-(optionally substituted carbocyclyl), —($C_0$-

$C_6$ alkylene)-(optionally substituted aryl), —($C_0$-$C_6$ alkylene)-(optionally substituted heterocyclyl), and —($C_0$-$C_6$ alkylene)-(optionally substituted heteroaryl), —($C_2$-$C_6$ alkenylene or alkynylene)-(optionally substituted carbocyclyl), —($C_2$-$C_6$ alkenylene or alkynylene)-(optionally substituted aryl), —($C_2$-$C_6$ alkenylene or alkynylene)-(optionally substituted heterocyclyl), and —($C_2$-$C_6$ alkenylene or alkynylene)-(optionally substituted heteroaryl);

each alkyl, alkenyl, alkynyl, alkylene, alkenylene and alkynylene portion of R' and R" is optionally substituted and;

one or more methylene units of each alkyl, alkenyl, alkynyl, alkylene, alkenylene and alkynylene portion of R' and R" are optionally and independently replaced with —O—, —S—, —S(O)—, —S(O)$_2$, or —N($R^6$)—;

$R^5$ is selected from halogen, $C_1$-$C_4$ alkyl and —O—$C_1$-$C_4$ alkyl, wherein the alkyl portion of $R^5$ is optionally substituted, or two $R^5$ are taken together with the atoms to which they are bound to form an optionally substituted heterocyclyl; and n is 0, 1, 2, 3, or 4.

In some embodiments, the compound is other than

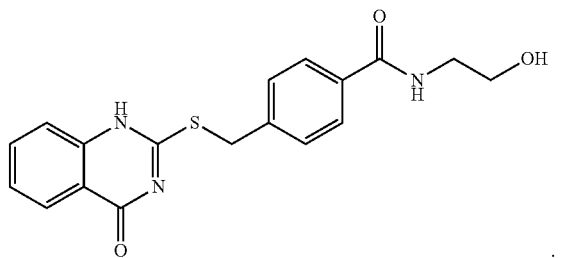 [SMILES: O=C(NCCO)c1ccc(CSc2nc(=O)c3ccccc3[nH]2)cc1]

In some embodiments, $R^1$ is hydrogen.

In some embodiments, $R^2$ is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino.

In some embodiments, $R^3$ is selected from hydrogen, fluoro, chloro and methyl.

In some embodiments, $R^2$ and $R^3$ are taken together to form 1H-benzo[d]imidazol-5-yl In some embodiments, X is C(O).

In some embodiments, Y is S.

In some embodiments, $R^4$ is selected from hydrogen, $C_1$-$C_4$ alkyl, $C_2$-$C_4$ alkenyl, $C_3$-$C_6$ cycloalkyl, and phenyl.

In some embodiments, $R^4$ is selected from hydrogen, methyl, ethyl, isopropyl, 1-propenyl, cyclopropyl, cyclopentyl and phenyl.

In some embodiments, n is 0.

In some embodiments, Z is N.

Although, as indicated above, various embodiments and aspects thereof for a variable in any of the formulas described herein (e.g., any of Formulas (I)-(VI)) may be selected from a group of chemical moieties, the invention also encompasses as further embodiments and aspects thereof situations where such variable is: a) selected from any subset of chemical moieties in such a group; and b) any single member of such a group. Further, where various embodiments and aspects thereof are set forth individually for each variable in any of the formulas described herein (e.g., any of Formulas (I)-(VI)), the invention encompasses all possible combinations of the different embodiments and aspects for each of the variables in the Formula.

Exemplary compounds of and useful in the present invention are set forth in Table 1 below, along with mass spectrometry and nuclear magnetic resonance data for certain compounds. In certain embodiments, the present invention provides a compound depicted in Table 1, or a pharmaceutically acceptable salt thereof.

TABLE 1

Exemplary Compounds and Spectrometric Data

| No. | Structure | MS Calc. | MS found | $^1$H NMR Data (400 MHz, DMSO-$d_6$) |
|---|---|---|---|---|
| 100 | 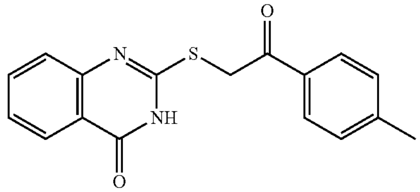 [SMILES: Cc1ccc(C(=O)CSc2nc3ccccc3c(=O)[nH]2)cc1] | — | — | — |
| 101 | 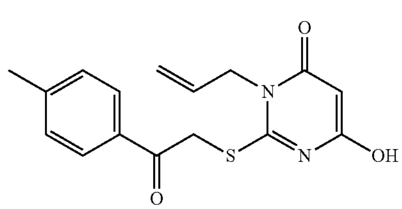 [SMILES: C=CCn1c(SCC(=O)c2ccc(C)cc2)nc(O)cc1=O] | — | — | — |

TABLE 1-continued

Exemplary Compounds and Spectrometric Data

| No. | Structure | MS Calc. | MS found | $^1$H NMR Data (400 MHz, DMSO-$d_6$) |
|---|---|---|---|---|
| 102 | 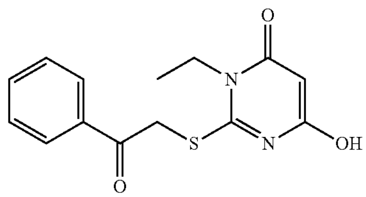 [SMILES: CCn1c(SCC(=O)c2ccccc2)nc(O)cc1=O] | — | — | — |
| 103 | 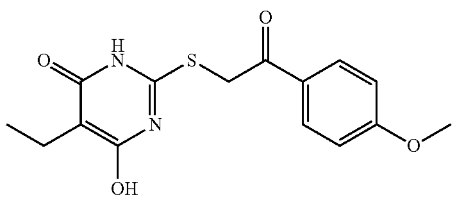 [SMILES: CCc1c(O)nc(SCC(=O)c2ccc(OC)cc2)[nH]c1=O] | — | — | — |
| 104 | 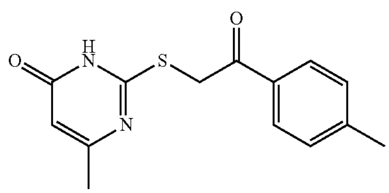 | — | — | — |
| 105 | 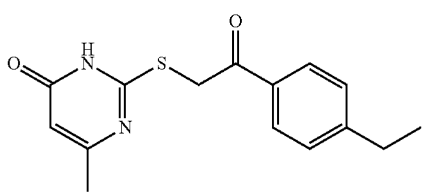 [SMILES: CCc1ccc(C(=O)CSc2nc(C)cc(=O)[nH]2)cc1] | — | — | — |
| 106 | 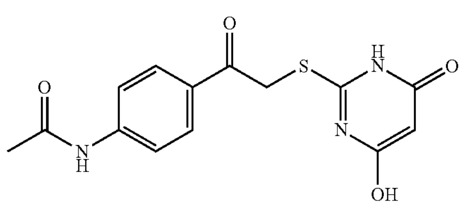 [SMILES: CC(=O)Nc1ccc(C(=O)CSc2nc(O)cc(=O)[nH]2)cc1] | — | — | — |
| 107 | 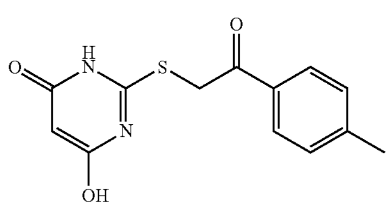 [SMILES: Cc1ccc(C(=O)CSc2nc(O)cc(=O)[nH]2)cc1] | — | — | — |
| 108 | 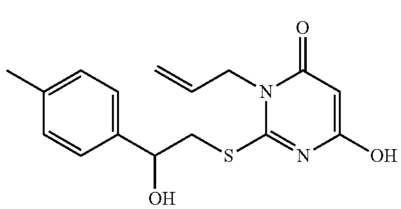 [SMILES: C=CCn1c(SCC(O)c2ccc(C)cc2)nc(O)cc1=O] | 318 | 319 | δ 11.30 (s, 1H), 7.30 (d, J = 8.0 Hz, 2H), 7.14 (d, J = 8.0 Hz, 2H), 5.84-5.77 (m, 1H), 5.71 (d, J = 4.8 Hz, 1H), 5.20-5.15 (m, 2H), 5.03 (d, J = 17.2 Hz, 1H), 4.79-4.76 (m, 1H), 4.54 (d, J = 2.8 Hz, 2H), 3.55-3.51 (m, 1H), 3.30-3.25 (m, 1H), 2.29 (s, 3H). |

TABLE 1-continued

Exemplary Compounds and Spectrometric Data

| No. | Structure | MS Calc. | MS found | $^1$H NMR Data (400 MHz, DMSO-d$_6$) |
|---|---|---|---|---|
| 109 | 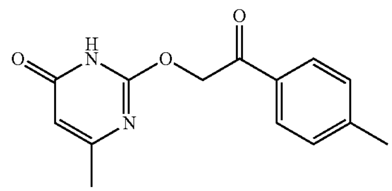 [SMILES: Cc1ccc(C(=O)COc2nc(C)cc(=O)[nH]2)cc1] | 258 | 259 | δ 11.30 (br, 1H), 7.95 (d, J = 8.0 Hz, 2H), 7.39 (t, J = 8.4 Hz, 2H), 5.55 (d, J = 11.6 Hz, 1H), 5.38 (s, 1H), 5.26 (s, 1H), 2.41 (s, 3H), 2.08 (d, J = 8.0 Hz, 3H). |
| 110 | 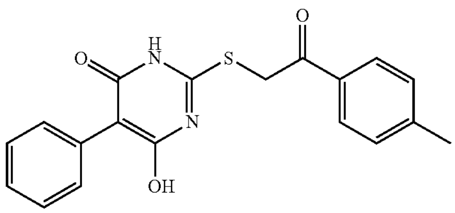 [SMILES: Cc1ccc(C(=O)CSc2nc(O)c(-c3ccccc3)c(=O)[nH]2)cc1] | — | — | — |
| 111 | 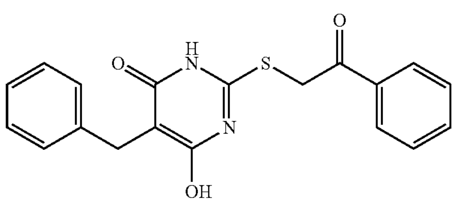 [SMILES: O=C(CSc1nc(O)c(Cc2ccccc2)c(=O)[nH]1)c1ccccc1] | — | — | — |
| 112 | 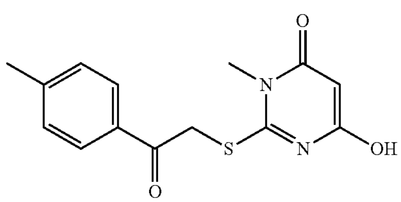 [SMILES: Cc1ccc(C(=O)CSc2nc(O)cc(=O)n2C)cc1] | 290 | 291 | δ 11.21 (br, 1H), 7.95 (d, J = 8.4 Hz, 2H), 7.39 (d, J = 8.4 Hz, 2H), 5.19 (s, 1H), 4.90 (s, 2H), 3.41 (s, 3H), 2.41 (s, 3H). |
| 113 | 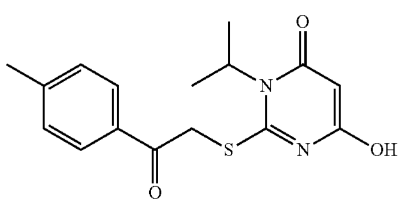 [SMILES: Cc1ccc(C(=O)CSc2nc(O)cc(=O)n2C(C)C)cc1] | 318 | 319 | δ 11.12 (s, 1H), 7.94 (d, J = 8.0 Hz, 2H), 7.37 (d, J = 8.0 Hz, 2H), 5.07 (s, 1H), 4.86 (s, 2H), 4.70-4.52 (m, 1H), 2.40 (s, 3H), 1.52 (d, J = 6.8 Hz, 6H). |
| 114 | 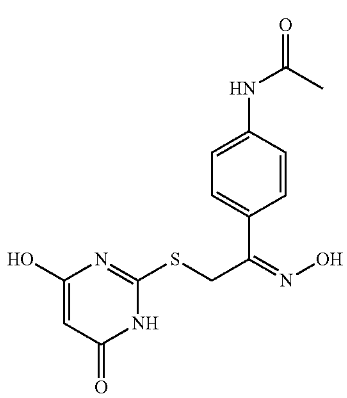 [SMILES: CC(=O)Nc1ccc(/C(CSc2nc(O)cc(=O)[nH]2)=N\O)cc1] | 334 | 335 | δ 12.40 (br, 1H), 11.74 (br, 1H), 11.50 (br, 1H), 10.07 (s, 1H), 7.70 (d, J = 8.8 Hz, 2H), 7.60 (d, J = 8.8 Hz, 2H), 5.14 (br, 1H), 4.43 (s, 2H), 2.05 (s, 3H). |

TABLE 1-continued

Exemplary Compounds and Spectrometric Data

| No. | Structure | MS Calc. | MS found | ¹H NMR Data (400 MHz, DMSO-d₆) |
|---|---|---|---|---|
| 115 | 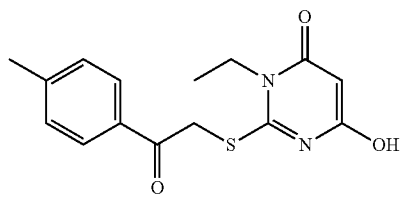 [SMILES: CCn1c(SCC(=O)c2ccc(C)cc2)nc(O)cc1=O] | 304 | 305 | δ 11.21 (br, 1H), 7.94 (d, J = 8.4 Hz, 2H), 7.39 (d, J = 8.4 Hz, 2H), 5.17 (s, 1H), 4.90 (s, 2H), 4.00 (q, J = 7.2 Hz, 2H), 2.41 (s, 3H), 1.23 (t, J = 7.2 Hz, 3H). |
| 116 | 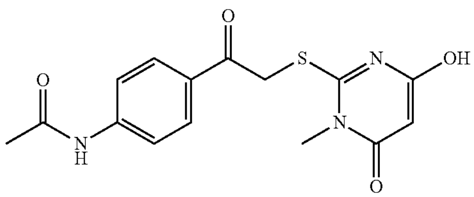 [SMILES: CC(=O)Nc1ccc(C(=O)CSc2nc(O)cc(=O)n2C)cc1] | 333 | 334 | δ 10.35 (br, 1H), 7.98 (d, J = 7.6 Hz, 2H), 7.72 (d, J = 8.8 Hz, 2H), 4.79 (s, 2H), 4.77 (br, 1H), 3.31 (s, 3H), 2.09 (s, 3H). |
| 117 | 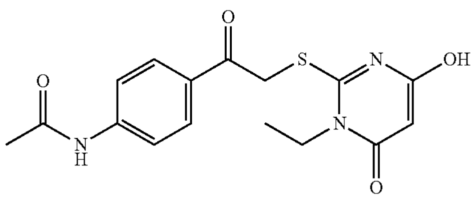 [SMILES: CCn1c(SCC(=O)c2ccc(NC(C)=O)cc2)nc(O)cc1=O] | 347 | 348 | δ 11.21 (br, 1H), 10.34 (s, 1H), 8.00 (d, J = 8.8 Hz, 2H), 7.74 (d, J = 8.8 Hz, 2H), 5.17 (s, 1H), 4.87 (s, 2H), 4.00 (q, J = 7.2 Hz, 2H), 2.10 (s, 3H), 1.23 (t, J = 7.2 Hz, 3H). |
| 118 | 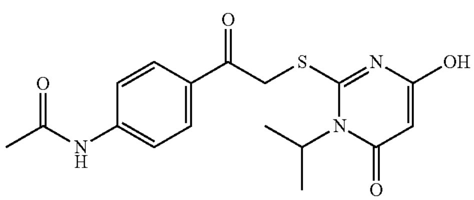 [SMILES: CC(=O)Nc1ccc(C(=O)CSc2nc(O)cc(=O)n2C(C)C)cc1] | 361 | 362 | δ 11.11 (s, 1H), 10.34 (s, 1H), 8.00 (d, J = 8.8 Hz, 2H), 7.74 (d, J = 8.4 Hz, 2H), 5.09 (s, 1H), 4.84 (s, 2H), 4.70-4.52 (m, 1H), 2.10 (s, 3H), 1.52 (d, J = 6.8 Hz, 6H). |
| 119 | 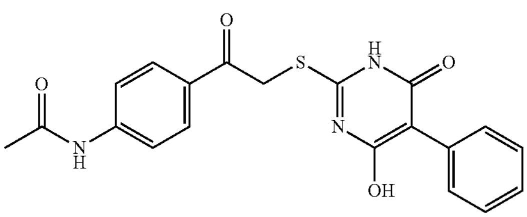 [SMILES: CC(=O)Nc1ccc(C(=O)CSc2nc(O)c(-c3ccccc3)c(=O)[nH]2)cc1] | 395 | 396 | δ 12.60 (br, 1H), 11.32 (br, 1H), 10.35 (s, 1H), 8.01 (d, J = 8.4 Hz, 2H), 7.45 (d, J = 8.4 Hz, 2H), 7.40 (d, J = 7.2 Hz, 2H), 7.32-7.28 (m, 2H), 7.21-7.19 (m, 1H), 4.88 (s, 2H), 2.10 (s, 3H). |
| 120 | 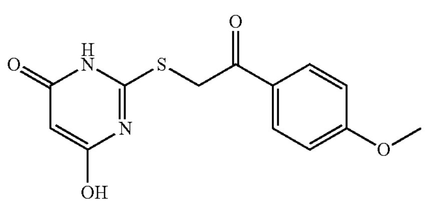 [SMILES: COc1ccc(C(=O)CSc2nc(O)cc(=O)[nH]2)cc1] | 292 | 293 | δ 11.52 (br, 2H), 8.00 (d, J = 8.8 Hz, 2H), 7.08 (d, J = 8.8 Hz, 2H), 5.16 (br, 1H), 4.79 (s, 2H), 3.86 (s, 3H). |
| 121 | 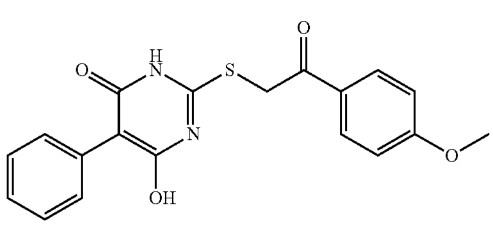 [SMILES: COc1ccc(C(=O)CSc2nc(O)c(-c3ccccc3)c(=O)[nH]2)cc1] | 368 | 369 | δ 12.51 (br, 1H), 11.48 (br, 1H), 8.03 (d, J = 8.8 Hz, 2H), 7.40 (d, J = 7.6 Hz, 2H), 7.32-7.28 (m, 2H), 7.19-7.11 (m, 1H), 7.09 (d, J = 8.8 Hz, 2H), 4.90 (s, 2H), 3.87 (s, 3H). |

TABLE 1-continued

Exemplary Compounds and Spectrometric Data

| No. | Structure | MS Calc. | MS found | $^1$H NMR Data (400 MHz, DMSO-$d_6$) |
|---|---|---|---|---|
| 122 | 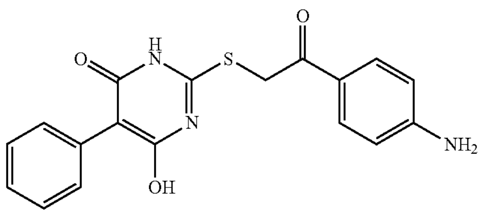 [SMILES: Nc1ccc(C(=O)CSc2nc(O)c(-c3ccccc3)c(=O)[nH]2)cc1] | 353 | 354 | δ 12.59 (br, 1H), 11.34 (br, 1H), 7.75 (d, J = 8.8 Hz, 2H), 7.41 (d, J = 7.6 Hz, 2H), 7.32-7.28 (m, 2H), 7.21-7.18 (m, 1H), 6.59 (d, J = 8.4 Hz, 2H), 6.23 (s, 2H), 4.77 (s, 2H). |
| 123 | 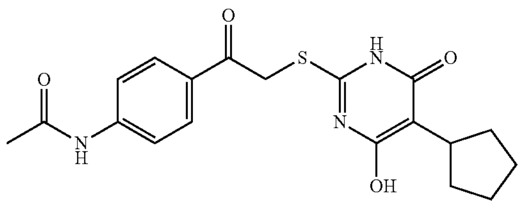 [SMILES: CC(=O)Nc1ccc(C(=O)CSc2nc(O)c(C3CCCC3)c(=O)[nH]2)cc1] | 387 | 388 | δ 12.31 (br, 1H), 10.99 (br, 1H), 10.34 (s, 1H), 7.99 (d, J = 8.8 Hz, 2H), 7.73 (d, J = 7.6 Hz, 2H), 4.80 (s, 2H), 3.20-3.05 (m, 1H), 2.10 (s, 3H), 1.78-1.48 (m, 8H). |
| 124 | 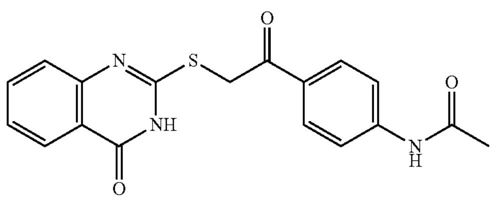 [SMILES: CC(=O)Nc1ccc(C(=O)CSc2nc3ccccc3c(=O)[nH]2)cc1] | 353 | 354 | δ 12.71 (br, 1H), 10.36 (br, 1H), 8.06 (d, J = 8.4 Hz, 2H), 8.00 (d, J = 7.6 Hz, 1H), 7.76 (d, J = 8.4 Hz, 2H), 7.68 (t, J = 7.6 Hz, 1H), 7.38 (t, J = 7.6 Hz, 1H), 7.17 (d, J = 8.0 Hz, 1H), 4.81 (s, 2H), 2.11 (s, 3H). |
| 125 | 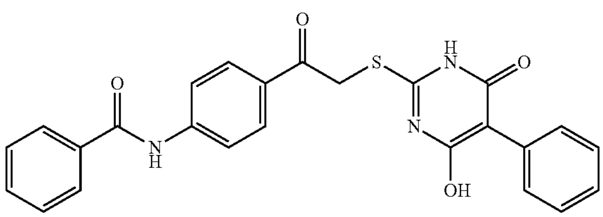 [SMILES: O=C(CSc1nc(O)c(-c2ccccc2)c(=O)[nH]1)c1ccc(NC(=O)c2ccccc2)cc1] | 457 | 458 | δ 12.66 (br, 1H), 11.35 (br, 1H), 10.63 (s, 1H), 8.08 (d, J = 8.4 Hz, 2H), 8.01-7.98 (m, 4H), 7.65-7.55 (m, 3H), 7.41 (d, J = 7.2 Hz, 2H), 7.32-7.88 (m, 3H), 4.93 (s, 2H). |
| 126 | 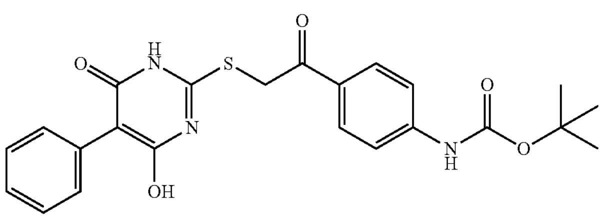 [SMILES: CC(C)(C)OC(=O)Nc1ccc(C(=O)CSc2nc(O)c(-c3ccccc3)c(=O)[nH]2)cc1] | 453 | 454 | δ 12.65 (br, 1H), 11.25 (br, 1H), 9.86 (s, 1H), 7.97 (d, J = 8.8 Hz, 2H), 7.62 (d, J = 8.8 Hz, 2H), 7.40 (d, J = 7.6 Hz, 2H), 7.32-7.28 (m, 2H), 7.21-7.19 (m, 1H), 4.87 (s, 2H), 1.46 (s, 9H). |
| 127 | 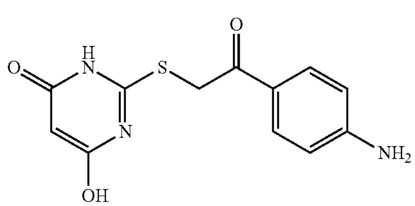 [SMILES: Nc1ccc(C(=O)CSc2nc(O)cc(=O)[nH]2)cc1] | 277 | 278 | δ 11.70 (br, 2H), 7.72 (d, J = 8.8 Hz, 2H), 6.57 (d, J = 8.8 Hz, 2H), 6.20 (s, 2H), 5.08 (br, 1H), 4.63 (s, 2H). |
| 128 | 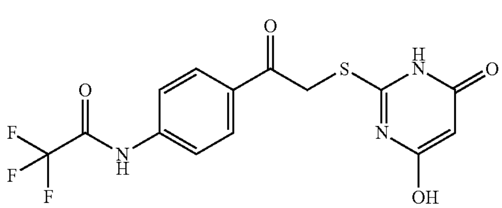 [SMILES: O=C(CSc1nc(O)cc(=O)[nH]1)c1ccc(NC(=O)C(F)(F)F)cc1] | 373 | 374 | δ 11.61 (br, 1H), 11.36 (br, 1H), 8.09 (d, J = 8.8 Hz, 2H), 7.86 (d, J = 8.4 Hz, 2H), 5.15 (br, 1H), 4.81 (s, 2H). |

TABLE 1-continued

Exemplary Compounds and Spectrometric Data

| No. | Structure | MS Calc. | MS found | $^1$H NMR Data (400 MHz, DMSO-$d_6$) |
|---|---|---|---|---|
| 129 | 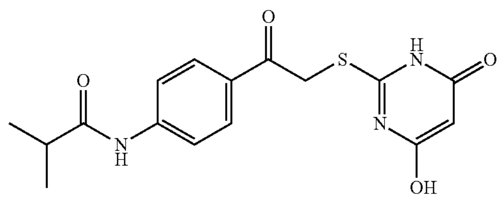 [SMILES: CC(C)C(=O)Nc1ccc(C(=O)CSc2nc(O)cc(=O)[nH]2)cc1] | 347 | 348 | δ 12.31 (br, 1H), 11.44 (br, 1H), 10.24 (s, 1H), 7.99 (d, J = 8.4 Hz, 2H), 7.77 (d, J = 8.8 Hz, 2H), 5.16 (br, 1H), 4.78 (s, 2H), 2.65-2.62 (m, 1H), 1.49 (d, J = 6.8 Hz, 6H). |
| 130 | 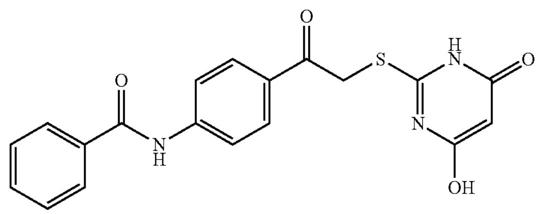 [SMILES: O=C(CSc1nc(O)cc(=O)[nH]1)c1ccc(NC(=O)c2ccccc2)cc1] | 381 | 382 | δ 12.39 (br, 1H), 11.39 (br, 1H), 10.62 (s, 1H), 8.06 (d, J = 8.8 Hz, 2H), 7.99-7.97 (m, 4H), 7.65-7.55 (m, 3 H), 5.17 (br, 1H), 4.82 (s, 2H). |
| 131 | 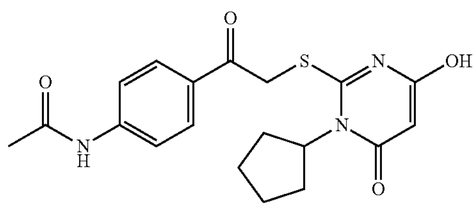 [SMILES: CC(=O)Nc1ccc(C(=O)CSc2nc(O)cc(=O)n2C2CCCC2)cc1] | 387 | 388 | δ 11.15 (s, 1H), 10.34 (s, 1H), 8.02 (d, J = 8.8 Hz, 2H), 7.76 (d, J = 8.8 Hz, 2H), 5.12 (s, 1H), 4.85-4.83 (m, 3H), 2.19-2.15 (m, 2H), 2.09 (s, 3H), 1.90-1.85 (m, 4H), 1.59-1.57 (m, 2H). |
| 132 | 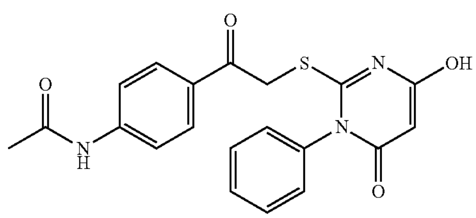 [SMILES: CC(=O)Nc1ccc(C(=O)CSc2nc(O)cc(=O)n2-c2ccccc2)cc1] | 395 | 396 | δ 11.47 (s, 1H), 10.35 (s, 1H), 7.97 (d, J = 8.8 Hz, 2H), 7.74 (d, J = 8.8 Hz, 2H), 7.57-7.55 (m, 3H), 7.36-7.34 (m, 2H), 5.27 (s, 1H), 4.73 (s, 2H), 2.09 (s, 3H). |
| 133 | 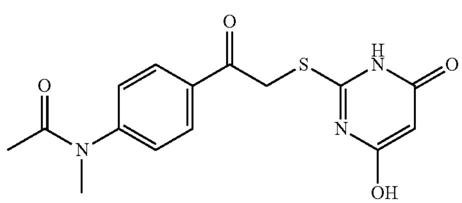 [SMILES: CC(=O)N(C)c1ccc(C(=O)CSc2nc(O)cc(=O)[nH]2)cc1] | 333 | 334 | δ 12.50 (br, 1H), 11.35 (br, 1H), 8.08 (d, J = 8.4 Hz, 2H), 7.54 (d, J = 8.4 Hz, 2H), 5.12 (br, 1H), 4,84 (s, 2H), 3.24 (s, 3H), 1.93 (s, 3H). |
| 134 | 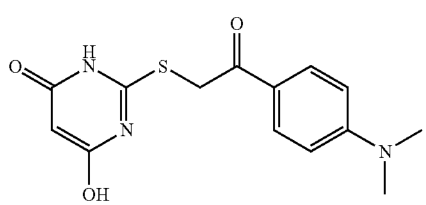 [SMILES: CN(C)c1ccc(C(=O)CSc2nc(O)cc(=O)[nH]2)cc1] | 305 | 306 | δ 12.38 (br, 1H), 11.42 (br, 1H), 7.85 (d, J = 8.8 Hz, 2H), 6.74 (d, J = 8.8 Hz, 2H), 5.14 (br, 1H), 4.72 (s, 2H), 3.04 (s, 6H). |
| 135 | 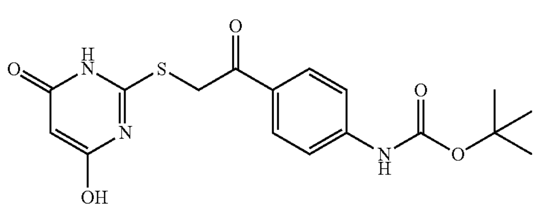 [SMILES: CC(C)(C)OC(=O)Nc1ccc(C(=O)CSc2nc(O)cc(=O)[nH]2)cc1] | 377 | 378 | δ 12.40 (br, 1H), 11.39 (br, 1H), 9.86 (s, 1H), 7.95 (d, J = 8.8 Hz, 2H), 7.60 (d, J = 8.8 Hz, 2H), 5.16 (br, 1H), 4.76 (s, 2H), 1.49 (s, 9H). |

TABLE 1-continued

Exemplary Compounds and Spectrometric Data

| No. | Structure | MS Calc. | MS found | $^1$H NMR Data (400 MHz, DMSO-$d_6$) |
|---|---|---|---|---|
| 136 | 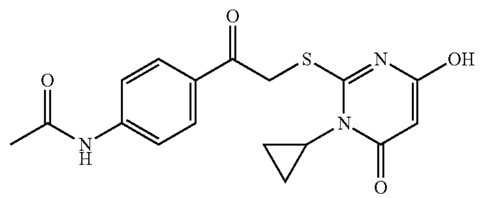 [SMILES: CC(=O)Nc1ccc(C(=O)CSc2nc(O)cc(=O)n2C2CC2)cc1] | 359 | 360 | δ 11.12 (s, 1H), 10.34 (s, 1H), 8.02 (d, J = 8.8 Hz, 2H), 7.76 (d, J = 8.8 Hz, 2H), 5.11 (s, 1H), 4.80 (s, 2H), 2.73-2.71 (m, 1H), 2.09 (s, 3H), 1.19-1.17 (m, 2H), 0.91-0.90 (m, 2H). |
| 137 | 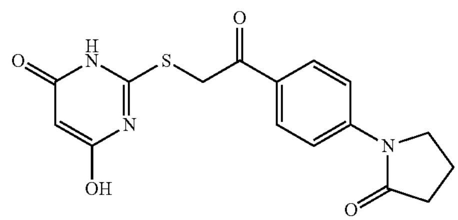 [SMILES: O=C(CSc1nc(O)cc(=O)[nH]1)c1ccc(N2CCCC2=O)cc1] | 345 | 346 | δ 11.66 (br, 2H), 8.06 (d, J = 9.2 Hz, 2H), 7.86 (d, J = 8.8 Hz, 2H), 5.17 (s, 1H), 4.81 (s, 2H), 3.89 (t, J = 7.2 Hz, 2H), 2.57-2.52 (m, 2H), 2.11-2.07 (m, 2H) |
| 138 | 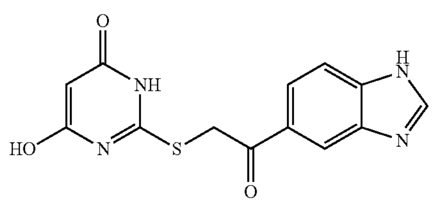 [SMILES: O=C(CSc1nc(O)cc(=O)[nH]1)c1ccc2[nH]cnc2c1] | 302 | 303 | δ 12.66 (br, 1H), 11.43 (br, 1H), 8.45 (s, 1H), 8.37 (s, 1H), 7.91-7.89 (m, 1H), 7.70 (d, J = 8.4 Hz, 1H), 5.16 (br, 1H), 4.94 (s, 2H). |
| 139 | 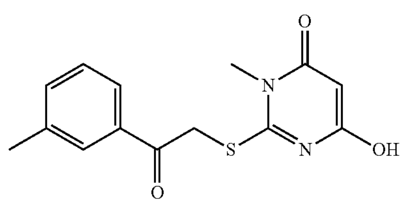 [SMILES: Cc1cccc(C(=O)CSc2nc(O)cc(=O)n2C)c1] | 290 | 291 | δ 11.21 (s, 1H), 7.87-7.85 (m, 2H), 7.53-7.45 (m, 2H), 5.20 (s, 1H), 4.92 (s, 2H), 3.41 (s, 3H), 2.41 (s, 3H). |
| 140 | 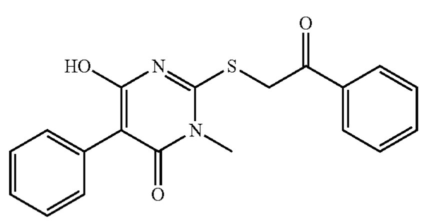 [SMILES: Cn1c(SCC(=O)c2ccccc2)nc(O)c(-c2ccccc2)c1=O] | 352 | 353 | δ 11.16 (s, 1H), 8.07 (d, J = 7.2 Hz, 2H), 7.71 (t, J = 7.6 Hz, 1H), 7.60 (t, J = 7.6 Hz, 2H), 7.41 (d, J = 8.4 Hz, 2H), 7.31 (t, J = 7.6 Hz, 2H), 7.20 (t, J = 7.2 Hz, 1H), 5.06 (s, 2H), 3.49 (s, 3H). |
| 141 | 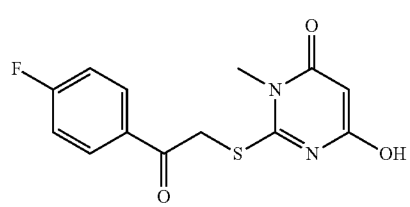 [SMILES: Cn1c(SCC(=O)c2ccc(F)cc2)nc(O)cc1=O] | 294 | 295 | δ 11.18 (s, 1H), 8.16-8.12 (m, 2H), 7.41 (t, J = 8.8 Hz, 2H), 5.19 (s, 1H), 4.91 (s, 2H), 3.41 (s, 3H). |
| 142 | 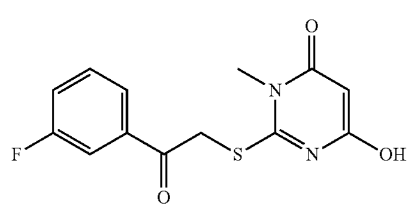 [SMILES: Cn1c(SCC(=O)c2cccc(F)c2)nc(O)cc1=O] | 294 | 295 | δ 11.18 (s, 1H), 7.90 (d, J = 8.0 Hz, 1H), 7.86-7.82 (m, 1H), 7.67-7.62 (m, 1H), 7.59-7.54 (m, 1H), 5.19 (s, 1H), 4.91 (s, 2H), 3.41 (s, 3H). |

TABLE 1-continued

Exemplary Compounds and Spectrometric Data

| No. | Structure | MS Calc. | MS found | $^1$H NMR Data (400 MHz, DMSO-d$_6$) |
|---|---|---|---|---|
| 143 | 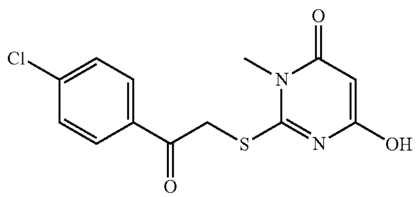 [SMILES: Cn1c(SCC(=O)c2ccc(Cl)cc2)nc(O)cc1=O] | 310 | 311 | δ 11.18 (s, 1H), 8.06 (d, J = 8.4 Hz, 2H), 7.65 (d, J = 8.4 Hz, 2H), 5.19 (s, 1H), 4.90 (s, 2H), 3.41 (s, 3H). |
| 144 | 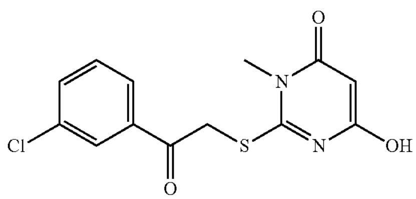 [SMILES: Cn1c(SCC(=O)c2cccc(Cl)c2)nc(O)cc1=O] | 310 | 311 | δ 11.19 (s, 1H), 8.06 (t, J = 1.6 Hz, 1H), 8.00 (d, J = 7.6 Hz, 1H), 7.79-7.76 (m, 1H), 7.62 (t, J = 7.6 Hz, 1H), 5.19 (s, 1H), 4.91 (s, 2H), 3.41 (s, 3H). |
| 145 | 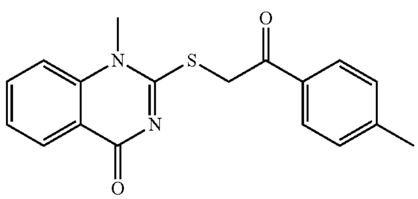 [SMILES: Cc1ccc(C(=O)CSc2nc(=O)c3ccccc3n2C)cc1] | 324 | 325 | δ 8.02-7.98 (m, 3H), 7.83-7.78 (m, 1H), 7.68 (d, J = 8.4 Hz, 1H), 7.46 (t, J = 7.2 Hz, 1H), 7.39 (d, J = 8.0 Hz, 2H), 4.92 (s, 2H), 3.85 (s, 3H), 2.41 (s, 3H). |

General Synthetic Methods and Intermediates:

The compounds of the present invention can be prepared by methods known to one of ordinary skill in the art and/or by reference to the schemes shown below and the synthetic examples that follow. Exemplary synthetic routes are set forth in the Schemes below, and in the Examples.

One of ordinary skill in the art will recognize that numerous variations in reaction conditions including variations in solvent, reagents, catalysts, reaction temperatures and times are possible for each of the reactions described. Variation of order of synthetic steps and alternative synthetic routes are also possible.

The compounds of the present invention can be prepared by methods known to one of ordinary skill in the art and/or by reference to the schemes shown below and the synthetic examples that follow.

4. Uses, Formulation and Administration

Exemplary Uses

Compounds of the invention are inhibitors of class I histone deacetylases (HDAC) and in particular HDAC2, and are useful for promoting cognitive function and enhancing learning and memory formation. As a result, these compounds are useful in treating, alleviating, and/or preventing various conditions, including e.g., neurological disorders, memory and cognitive function disorders/impairments, extinction learning disorders, fungal diseases, inflammatory diseases, hematological diseases, and neoplastic diseases in humans and animals.

HDAC Inhibition

The compounds of the present invention are useful in a variety of applications for human and animal health. The compounds of the invention are histone deacetylase (HDAC) inhibitors. A histone deacetylase inhibitor as used herein is a compound that inhibits, reduces, or otherwise modulates the activity of histone deacetylase. HDACs catalyze the removal of acetyl groups from lysine residues on proteins, including histones. HDAC inhibitors also show diverse biological functions including effecting gene expression, cell differentiation, cell cycle progression, growth arrest, and/or apoptosis. (J. Med. Chem. 2003, 46:5097 and Curr. Med. Chem. 2003, 10:2343). In various embodiments, the compounds of the invention reduce HDAC activity by at least about 50%, at least about 75%, or at least about 90% or more. In further embodiments, HDAC activity is reduced by at least about 95% or at least about 99% or more.

One aspect of the invention provides a method of inhibiting histone deacetylase in a cell, comprising contacting a cell in which inhibition of histone deacetylase is desired with an inhibition effective amount of a compound of the invention or a composition thereof. Because compounds of the invention inhibit histone deacetylase(s), they are useful research tools for in vitro study of the role of histone deacetylase in biological processes. Accordingly, in one aspect of the invention, the step of contacting the cell is performed in vitro.

The term an "inhibiting effective amount" is meant to denote a dosage sufficient to cause inhibition of activity of one or more histone deacetylase in a cell, which cell can be in a multicellular organism. The multicellular organism can be a plant, a fungus, or an animal, preferably a mammal, more preferably a human. The fungus may be infecting a plant or a mammal, preferably a human, and could therefore be located in and/or on the plant or mammal. If the histone deacetylase is in a multicellular organism, the method according to this aspect of the invention comprises administering to the organism a compound or composition of the invention. Measurement of the effect of a compound of the invention on the enzymatic activity of a histone deacetylase is achieved using known methodologies. For example, Bradner, J. et al. Nature Chemical Biology, Vol. 6, March 2010, 238-243.

The potential of HDAC inhibitors is tremendous, but the development of clinical compounds will likely require the design of isoform selective compounds to minimize side effect issues e.g., fatigue, anorexia, hematological and GI-toxicity. Isoform specific HDAC inhibitors provide advantages by reducing toxicities associated with inhibition of other HDACs. Specific HDAC inhibitors provide a higher therapeutic index, resulting in better tolerance by patients during chronic or long term treatment. While several HDAC inhibitors are now in the clinic, most of these do not show significant selectivity for individual HDAC isoforms.

The compounds of the present invention inhibit HDAC2. In some embodiments, the compound reduces the activity of other, but fewer than all histone deacetylases in the cell. In certain embodiments, the compound reduces the activity of HDAC2 to a greater extent than other histone deacetylases.

In certain embodiments, the present invention relates to the aforementioned compound, wherein the compounds of the invention are selective HDAC2 inhibitors.

In one embodiment, a compound of the invention is selective for HDAC2 and will have at least about 2-fold (e.g., at least about 5-fold, 10-fold, 15-fold, or 20-fold) greater activity to inhibit HDAC2 as compared to one or more other HDACs (e.g., one or more HDACs of class I or II). In one embodiment, a compound of the invention will have at least about 2-fold (e.g., at least about 5-fold, 10-fold, 15-fold, or 20-fold) greater activity to inhibit HDAC2 as compared to HDAC3. In one embodiment, a compound of the invention will have at least about 2-fold (e.g., at least about 5-fold, 10-fold, 15-fold, or 20-fold) greater activity to inhibit HDAC2 as compared to HDAC1. In one embodiment, a compound of the invention will have at least about 2-fold (e.g., at least about 5-fold, 10-fold, 15-fold, or 20-fold) greater activity to inhibit HDAC2 as compared to all other HDACs of a particular class of HDACs (e.g., one or more HDACs of class I or II). In one embodiment, a compound of the invention will have at least about 2-fold (e.g., at least about 5-fold, 10-fold, 15-fold, or 20-fold) greater activity to inhibit HDAC2 as compared to all other HDACs.

In another embodiment, a compound selectively inhibits HDAC2 with an $IC_{50}$ value greater than 0.0000001 μM and less than or equal to 0.1 μM, 1 μM, 5 μM, or 30 μM.

Neurological Disorders

In one aspect, the invention provides methods and compositions for treating, alleviating, and/or preventing neurological disorders.

Recent reports have detailed the importance of histone acetylation in central nervous system ("CNS") functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525).

In one aspect, the invention provides methods and compositions for treating, alleviating, and/or preventing neurological disorders. The term "neurological disorder" as used herein includes neurological diseases, neurodegenerative diseases and neuropsychiatric disorders. A neurological disorder is a condition having as a component a central or peripheral nervous system malfunction. Neurological disorders may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems).

As used herein, the term "neurodegenerative disease" implies any disorder that might be reversed, deterred, managed, treated, improved, or eliminated with agents that stimulate the generation of new neurons. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

In some instances the neurological disorder is a neuropsychiatric disorder, which refers to conditions or disorders that relate to the functioning of the brain and the cognitive processes or behavior. Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV).

One group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. A fourth group of neuropsychiatric disorders includes disorders of learning, memory, and intelligence, such as mental retardation and dementia. Accordingly, neuropsychiatric disorders encompass schizophrenia, delirium, attention deficit disorder (ADD), schizoaffective disorder, Alzheimer's disease, Rubinstein-Taybi syndrome, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

In one embodiment, the neurological disorder is Alzheimer's disease, Huntington's disease, seizure-induced memory loss, schizophrenia, Rubinstein Taybi syndrome, Rett Syndrome, Fragile X, Lewy body dementia, vascular dementia, ADHD, ADD, dyslexia, bipolar disorder and social, cognitive and learning disorders associated with autism, traumatic head injury, or attention deficit disorder.

In another embodiment, the neurological disorder is an anxiety disorder, conditioned fear response, panic disorder, obsessive compulsive disorder, post-traumatic stress disorder, phobia, social anxiety disorder, or substance dependence recovery.

In some embodiments neurological disorders are treated or prevented by decreasing the amount of DNA damage within the neuronal cell. In some embodiments neurological disorders are treated or prevented by increasing histone deacetylase activity within the neuronal cell. In some embodiments neurological disorders are treated or prevented by decreasing histone acetyl transferase activity within the neuronal cell. In some embodiments neurological disorders are treated or prevented by increasing the activity of class I histone deacetylases.

Enhancing Cognitive Function

In one aspect, the invention provides methods and compositions for promoting cognitive function and enhancing learning and memory formation in both normal subjects as well as those suffering from memory loss and cognitive function disorders/impairments. A normal subject, as used herein, is a subject that has not been diagnosed with a disorder associated with impaired cognitive function. "Cognitive function" refers to mental processes of a subject relating to information gathering and/or processing; the understanding, reasoning, and/or application of information and/or ideas; the abstraction or specification of ideas and/or information; acts of creativity, problem-solving, and possibly intuition; and mental processes such as learning, perception, and/or awareness of ideas and/or information. The mental processes are distinct from those of beliefs, desires, and the like.

Memory Disorders/Impairment

Transcription is thought to be a key step for long-term memory processes (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705). Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467).

A "memory" as used herein refers to the ability to recover information about past events or knowledge. Memories include short-term memory (also referred to as working or recent memory) and long-term memory. Short-term memories involve recent events, while long-term memories relate to the recall of events of the more distant past. Methods of assessing the ability to recall a memory are known to those of skill in the art and may involve routine cognitive tests. Enhancing or retrieving memories is distinct from learning. However, in some instances in the art learning is referred to as memory. Learning, unlike memory enhancement, refers to the ability to create new memories that had not previously existed. Thus in order to test the ability of a compound to effect the ability of a subject to learn rather than recall old memories, the compound would be administered prior to or at the same time as the memory is created. In order to test the ability of a compound to affect recall of a previously created memory the compound is administered after the memory is created and preferably after the memory is lost.

As used herein "age related memory loss" refers to any of a continuum of conditions characterized by a deterioration of neurological functioning that does not rise to the level of a dementia, as further defined herein and/or as defined by the Diagnostic and Statistical Manual of Mental Disorders: 4th Edition of the American Psychiatric Association (DSM-IV, 1994). Age related memory loss is characterized by objective loss of memory in an older subject compared to his or her younger years, but cognitive test performance that is within normal limits for the subject's age. Age related memory loss subjects score within a normal range on standardized diagnostic tests for dementias, as set forth by the DSM-IV. Moreover, the DSM-IV provides separate diagnostic criteria for a condition termed Age-Related Cognitive Decline. In the context of the present invention, as well as the terms "Age-Associated Memory Impairment" and "Age-Consistent Memory Decline" are understood to be synonymous with the age related memory loss. Age-related memory loss may include decreased brain weight, gyral atrophy, ventricular dilation, and selective loss of neurons within different brain regions. For purposes of some embodiments of the present invention, more progressive forms of memory loss are also included under the definition of age-related memory disorder. Thus persons having greater than age-normal memory loss and cognitive impairment, yet scoring below the diagnostic threshold for frank dementia, may be referred to as having a mild neurocognitive disorder, mild cognitive impairment, late-life forgetfulness, benign senescent forgetfulness, incipient dementia, provisional dementia, and the like. Such subjects may be slightly more susceptible to developing frank dementia in later life (See also US patent application 2006/008517 (Vasogen Ireland limited) which is incorporated by reference). Symptoms associated with age-related memory loss include but are not limited to alterations in biochemical markers associated with the aging brain, such as IL-1 beta, IFN-gamma, p-JNK, p-ERK, reduction in synaptic activity or function, such as synaptic plasticity, evidenced by reduction in long term potentiation, diminution of memory and learning.

As used herein "injury related memory loss" refers to a loss of memory wherein there is damage to the brain, and there may have also been neurological damage. Sources of brain injury include traumatic brain injury such as concussive injuries or penetrating head wounds, brain tumors, alcoholism, Alzheimer's disease, stroke, heart attack and other conditions that deprive the brain of oxygen, meningitis, AIDS, viral encephalitis, and hydrocephalus.

Methods for enhancing memories can include reestablishing access to memories as well as recapturing memories. The term re-establishing access as used herein refers to increasing retrieval of a memory. Although Applicants are not bound by a mechanism of action, it is believed that the compounds of the invention are effective in increasing retrieval of memories by re-establishing a synaptic network. The process of re-establishing a synaptic network may include an increase in the number of active brain synapses and or a reversal of neuronal loss.

Neurogenesis, or the birth of new neuronal cells, was thought to occur only in developing organisms. However, recent research has demonstrated that neurogenesis does indeed continue into and throughout adult life. On going neurogenesis is thought to be an important mechanism underlying neuronal plasticity, enabling organisms to adapt to environmental changes and influencing learning and memory throughout life. In one aspect, the invention includes a method of increasing synaptic density in a subject comprising administering to the subject in need of such increase a compound of the invention or a pharmaceutically acceptable salt, hydrate, solvate, or prodrug thereof. In one aspect, the invention includes a method of increasing synaptic plasticity in a subject comprising administering to the subject in need of such increase a compound of the invention or a pharmaceutically acceptable salt, hydrate, solvate, or prodrug thereof. In one aspect, the invention includes a method of increasing dendritic density in neurons in a subject comprising administering to the subject in need of such increase a compound of the invention or a pharmaceutically acceptable salt, hydrate, solvate, or prodrug thereof.

The invention provides methods for enhancing memory in a subject having a memory disorder. Examples of types of memory disorders include Alzheimer's disease, absent-minded professor, absent-mindedness, amnesia, anterograde amnesia, blackout (alcohol-related amnesia), bromism, childhood amnesia, false memory syndrome, fugue state, hyperthymesia, Korsakoff's syndrome, lacunar amnesia, memory distrust syndrome, memory loss, post-traumatic amnesia, prosopamnesia, psychogenic amnesia, repressed memory, retrograde amnesia, Ribot's Law, selective memory loss, sywald skeid, source amnesia, source-monitoring error, the seven sins of memory, tip of the tongue, transient epileptic amensia, transient global amnesia, and twilight sleep.

In one embodiment, Alzheimer's disease is the memory disorder. Such methods optionally involve administering the inhibitor and monitoring the subject to identify recapture of a memory that was previously lost. Subjects may be monitored by routine tests known in the art.

In other embodiments the alzheimer's subject is one that has late stage Alzheimer's disease. Many of the drugs suggested for treating Alzheimer's disease are designed to treat the early stages of the disease by preventing plaque buildup. The compounds of the invention are useful for treating both early stages and late stages of dementia because they actually improve memory and cognition rather than preventing only plaque accumulation.

Cognitive Function Disorders/Impairment

The invention relates to methods of treating, alleviating, and/or preventing cognitive function disorders/impairments.

Impaired cognitive function refers to cognitive function that is not as robust as that observed in an age-matched normal subject and includes states in which cognitive function is reduced. In some cases, cognitive function is reduced by about 5%, about 10%, about 30%, or more, compared to cognitive function measured in an age-matched normal subject. Cognitive function may be promoted to any detectable degree, but in humans preferably is promoted sufficiently to allow an impaired subject to carry out daily activities of normal life.

In some embodiments, the cognitive function disorders or impairments are associated with, but not limited to, Alzheimer's disease, Huntington's disease, seizure induced memory loss, schizophrenia, Rubinstein Taybi syndrome, Rett Syndrome, Fragile X, Lewey body dementia, Vascular dementia, bipolar disorder and social, cognitive and learning disorders associated with autism, attention deficit hyperactivity disorder (ADHD), dyselexia, learning disorders, traumatic head injury, stroke induced cognitive and motor impairment, traumatic brain injury, neurodegeneration and neuronal loss mediated cognitive impairment, and attention deficit disorder.

In some embodiments, the cognitive function disorders or impairments are associated with, but not limited to, anxiety disorders, conditioned fear response, panic disorders, obsessive compulsive disorders, post-traumatic stress disorder, phobias, social anxiety disorders, substance dependence recovery or Age Associated Memory Impairment (AAMI), and Age Related Cognitive Decline (ARCD), or a memory or memories of an event (e.g., a traumatic event).

In some embodiments, the invention relates to methods of treating, alleviating, and/or preventing vascular dementia. Vascular dementia, also referred to as "multi-infarct dementia", refers to a group of syndromes caused by different mechanisms all resulting in vascular lesions in the brain. The main subtypes of vascular dementia are, for example vascular mild cognitive impairment, multi-infarct dementia, vascular dementia due to a strategic single infarct (affecting the thalamus, the anterior cerebral artery, the parietal lobes or the cingulate gyms), vascular dementia due to hemorrhagic lesions, small vessel disease (including, e.g. vascular dementia due to lacunar lesions and Binswanger disease), and mixed Alzheimer's Disease with vascular dementia.

In some embodiments, the invention relates to treating, alleviating, and/or preventing Huntington's Disease. Huntington's Disease is a neurological disease which results in cognitive decline associated with inexorable progression to death. Cognitive symptoms associated with Huntington's Disease include loss of intellectual speed, attention, and short term memory and/or behavioral symptoms.

Cognitive function may be assessed, and thus optionally defined, via one or more tests or assays for cognitive function. Non-limiting examples of a test or assay for cognitive function include CANTAB (see for example Fray et al. "CANTAB battery: proposed utility in neurotoxicology." Neurotoxicol Teratol 1996; 18(4):499-504), Stroop Test, Trail Making, Wechsler Digit Span, or the CogState computerized cognitive test (see also Dehaene et al. "Reward-dependent learning in neuronal networks for planning and decision making." Brain Res. 2000; 126:21729; Iverson et al. "Interpreting change on the WAIS-III/WMS-Ill in clinical samples." Arch Clin Neuropsychol. 2001; 16(2): 183-91; and Weaver et al. "Mild memory impairment in healthy older adults is distinct from normal aging." Cogn. 2006; 60(2):146-55). The methods of the invention may be used to promote cognitive function in a normal subject or to treat, alleviate and/or prevent a subject from having a cognitive dysfunction. A normal subject, as used herein, is a subject that has not been diagnosed with a disorder associated with impaired cognitive function.

Extinction Learning Disorders

In one aspect, the invention relates to methods of treating, alleviating, and/or preventing extinction learning disorders e.g., a fear extinction deficit.

It has been demonstrated that administration of the HDAC inhibitors sodium butyrate or trichostatin A facilitates fear extinction in mice and this enhancement mirrors that caused by commonly used behavioral manipulation and is consistent with other studies demonstrating a role for the hippocampus in the extinction of contextual fear (Lattal, et al., 2007, Behav. Neurosci. 121, 5, 1125-1131).

Compounds of the invention can be used to facilitate the psychological process of extinction learning and thus are useful for treating, alleviating, and/or preventing neuropsychiatric disorders and other related disorders. Unlike traditional anti-anxiety drugs that are administered on a chronic basis and address physiological symptoms of anxiety, the compounds of the invention can be used on a chronic or acute basis in conjunction with a second therapy e.g., psychotherapy.

In one aspect, the present invention is directed to methods for treating, alleviating, and/or preventing a subject from having a neuropsychiatric disorder. The methods comprise subjecting the subject to one or more sessions of a combination therapy protocol, where the combination therapy protocol comprises an acute administration of a therapeutically effective amount of a compound of the invention that enhances learning or conditioning in combination with a session of psychotherapy. By "acute administration" is intended a single exposure of the subject to the therapeutically effective amount of the compound that enhances learning or conditioning. In one aspect, the exposure to the compound occurs within about 24 hours prior to initiating the session of psychotherapy, preferably within about 12 hours, and more preferably within about 6 hours prior to initiating the session of psychotherapy. A full course of treatment for the neuropsychiatric disorder entails at least one session of this combination therapy protocol.

For purposes of the present invention, a subject may have a single disorder, or may have a constellation of disorders that are to be treated, alleviated, and/or prevented by the methods described herein.

The neuropsychiatric disorders contemplated in the present invention include, but are not limited to, fear and anxiety disorders, addictive disorders including substance-abuse disorders, and mood disorders. Within the fear and anxiety disorder category, the invention encompasses the treatment or prevention of panic disorder, specific phobia, post-traumatic stress disorder (PTSD), obsessive-compulsive disorder, and movement disorders such as Tourette's syndrome. The disorders contemplated herein are defined in, for example, the DSM-IV (Diagnostic and Statistical Manual of Mental Disorders (4th ed., American Psychiatric Association, Washington D.C., 1994)), which is herein incorporated by reference.

Anxiety-related disorders relate to those disorders characterized by fear, anxiety, addiction, and the like. Patients with anxiety-related disorders can have a single such disorder, or can have a constellation of disorders. The anxiety-related disorders contemplated in the present invention include, but are not limited to, anxiety disorders, addictive disorders including substance-abuse disorders, mood disorders (e.g., depression and/or bipolar disorder), movement disorders such as Tourette's syndrome, psychogenic erectile dysfunction (impotence resulting from a man's inability to obtain or maintain an erection of his penis), insomnia (e.g. chronic insomnia), and eating disorders (e.g. anorexia).

Anxiety disorders include, but are not limited to, panic disorder, agoraphobia, social phobia, specific phobia, PTSD, obsessive-compulsive disorder, and generalized anxiety disorder. The disorders contemplated herein are defined in, for example, the DSM-IV (Diagnostic and Statistical Manual of Mental Disorders (4th ed., American Psychiatric Association, Washington D.C., 1994)).

Movement disorders are neurological conditions that affect the speed, fluency, quality, and ease of movement. Representative movement disorders include but are not limited to ataxia, chorea, myoclonus, dystonia, Parkinson's disease, restless leg syndrome, tics, and Tourette's syndrome. Movement disorders typically occur as a result of damage or disease in the basal ganglia region of the brain. Movement disorders can result from age-related changes, medications, genetic disorders, metabolic disorders, disease, stroke, or injury. Recovery of movement after stroke or injury may be facilitated when treated according to the methods of the invention.

Addictive disorders are disorders characterized by addiction to an activity or substance, and include, for example, alcohol addiction, drug addiction, and gambling addiction.

Depression refers to the clinical condition known as major depressive disorder, and is characterized by a state of intense sadness, melancholia, or despair that has advanced to the point of being disruptive to an individual's social functioning and/or activities of daily living. Depression is alleviated if either (or both) the severity or frequency of a symptom of the depression is reduced. However, a subject can be treated for depression in accordance with the methods of the invention irrespective of whether the treatment actually was successful in alleviating the depression.

Insomnia is defined herein as the inability to fall asleep or to stay asleep for a sufficient amount of time during regular sleeping hours. It includes acute insomnia, which occurs in either a transient or short term form, and chronic insomnia. It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As defined by the National Institute of Mental Health, Autism Spectrum Disorders (ASD), also widely known as Pervasive Developmental Disorders (PDDs), cause severe and pervasive impairment in thinking, feeling, language, and the ability to relate to others. These disorders are usually first diagnosed in early childhood and range from a severe form, called autistic disorder, through pervasive development disorder not otherwise specified (PDD-NOS), to a much milder form, Asperger syndrome. They also include two rare disorders, Rett syndrome and childhood disintegrative disorder.

Attention-Deficit Hyperactivity Disorder (ADHD) is one of the most common mental disorders that develop in children. Children with ADHD typically have impaired functioning in multiple settings, including home, school, and in relationships with peers. Symptoms of ADHD include impulsiveness, hyperactivity, and inattention.

Typical treatments encompassed by the present invention include combination therapies. For instance, the combination therapy may be a pharmacotherapy (i.e., a compound of the invention) and a behavioral therapy. Behavioral therapy comprises, but is not limited to, electroconvulsive seizure therapy, exercise, group therapy, talk therapy, or conditioning. In another embodiment, the behavioral therapy is cognitive-behavioral therapy. Examples of behavioral therapy that may be used in the ongoing methods are described, for example, in Cognitive-Behavioral Therapies by K. Dobson, ed., Guilford Publications, Inc., 2002; The new Handbook of Cognitive Therapy: Basics and Beyond by Judith S. S. Beck, Guilford Publications, Inc. 1995 herein incorporated by reference in their entireties. Any pharmaceutical active ingredient that is recognized by the skilled artisan as being a pharmacologic agent that enhances learning or conditioning can be used in the methods of the invention. For example, one such class of pharmaceutical active ingredients contemplated herein comprises compounds that increase the level of norepinephrine in the brain. Such compounds include those acting as norepinephrine reuptake inhibitors, for example tomoxetine, reboxetine, duloxetine, venlafaxine, and milnacipran, and those compounds that cause release of norepinephrine, for example amphetamine, dextroamphetamine, pemoline, and methylphenidate. Another class of such pharmaceutical active ingredients is those compounds that increase the level of acetylcholine in the brain, including, for example, compounds that block its breakdown. Examples of such compounds include, but are not limited to, donepezil HCl or Aricept™ and tacrine, which inhibit cholinesterase activity.

Methods of the invention also encompass the use in combination with a compound of the invention of any type of psychotherapy that is suitable for the particular psychiatric disorder for which the subject is undergoing treatment. Suitable methods of psychotherapy include exposure based psychotherapy, cognitive psychotherapy, and psychodynamically oriented psychotherapy. Methods of the invention also encompass exposing the subject to cognitive behavioral therapy (CBT), behavioral exposure treatments, virtual reality exposure (VRE) or cognitive remediation therapy.

Methods of the invention also encompass extinction training. The goal of extinction training is to pair a stimulus that previously provoked a deleterious, unwanted response with a new learning that will not lead to a negative outcome, thereby generating in a subject a new, more appropriate response to the stimulus to compete with and ideally replace the previous undesirable response. Extinction training frequently exposes a subject to a stimulus or situation in the absence of an aversive consequence, e.g., a subject that has deleterious, high anxiety responses to a given stimulus or situation is exposed to that stimulus or situation in the absence of an aversive consequence. A typical goal of extinction training is to produce new learning in the subject that results from the pairing of the original stimulus or situation with a non-deleterious outcome, thereby generating, in subsequent exposures to the stimulus, a more appropriate response in place of the unwanted response. An extinction learning event refers to a completed stimulus/response extinction training cycle.

One form of extinction training entails psychotherapy. For example, the methods of the invention contemplate treating, alleviating, and/or preventing anxiety disorders by: (i) administering psychotherapy to treat, alleviate, and/or prevent an anxiety-related disorder in a suitable human subject, and (ii) administering a therapeutically effective dose a compound of the invention to said subject on an achronic, post-training, pre-sleep basis. Suitable methods of psychotherapy include but are not limited to exposure-based psychotherapy, cognitive psychotherapy, and psychodynamically oriented psychotherapy.

One method of psychotherapy that is specifically contemplated is the use of virtual reality (VR) exposure therapy to treat, alleviate, and/or prevent an anxiety disorder using the methods of the invention.

Another method of psychotherapy that is particularly beneficial when utilized in combination with a compound or composition of the present invention is cognitive behavioral therapy ("CBT"). CBT is a form of psychotherapy that combines cognitive therapy and behavior therapy, and emphasizes the critical role of thinking in causing people to act and feel as they do. Therefore, if an individual is experiencing unwanted feelings and behaviors, CBT teaches that it is important to identify the thinking that is causing the undesirable feelings and/or behaviors and to learn how to replace this deleterious thinking with thoughts that lead to more desirable reactions. CBT is widely used to help people who are experiencing a range of mental health difficulties, some of which do not conveniently fit definitions of a particular medical affliction. CBT has been used to treat anxiety disorders, mood disorders, addictive disorders, eating disorders, insomnia, chronic pain, schizophrenia, fibromyalgia, ADHD, and autism spectrum disorders, among others. Post-extinction training pre-sleep administration of a compound of the invention, subsequent to CBT treatment, can be used to augment the effectiveness of the CBT treatment for these medical conditions.

In one embodiment, subjects suffering from social anxiety disorder undergo weekly cognitive behavioral therapy sessions to treat the affliction. After each therapy session, subjects are administered a therapeutically effective formulation of compounds of the invention on a post-extinction training pre-sleep basis. Relative to subjects treated only via cognitive behavioral therapy, or to subjects treated via cognitive behavioral therapy and a placebo, anxiety associated with social anxiety disorder is expected to be reduced to a greater extent in subjects treated with a combination of cognitive behavioral therapy and achronic administration of a compound of the invention on a post-extinction training pre-sleep basis.

In another embodiment of the invention, a compound of the invention is administered after extinction training only if the extinction training yields positive results on that day. For example, a subject undergoing cognitive behavioral therapy for PTSD is administered a compound of the invention on a post-extinction training only if the cognitive behavioral therapy was deemed to be successful, as determined by the subject and/or therapist. In one aspect, the compound is administered on a post-extinction, pre-sleep basis. In another aspect, a subject undergoing cognitive behavioral therapy for PTSD is administered a compound of the invention on a pre-extinction training. In one aspect, the compound is administered on a pre-extinction, pre-sleep basis. This method may also be useful when applied to treatment of autism spectrum disorders or attention-deficit hyperactivity disorder.

In some embodiments, the invention relates to treating a conidition where the treating comprises re-writing memories. Memories of an event often have an associated emotional component. For example, memories of a traumatic event can cause feelings of grief, guilt, or loss, as well as negative emotional responses such as anger, rage or aggression. Conversely, memories of a positive events can cause joy and increase feelings of self-confidence and self-worth. During the period of time when a memory is recalled it can modified to alter the associations and reduce or alter the emotional reactions to it. In some embodiments, HDAC inhibitors in combination with cognitive behavioral therapy or virtual reality therapy may allow the emotional associations with a memory to be re-written producing a longer term or greater therapeutic benefit.

In another embodiment of the invention, subjects afflicted with anxiety disorders such as PTSD receive extinction training using Eye Movement Desensitization and Reprocessing (EMDR), and subsequently are administered a therapeutically effective dose of a compound of the invention on a post-extinction training pre-sleep basis.

Another form of extinction training is provided by biofeedback, which is particularly useful in enabling subjects to learn to control physiological processes that normally occur involuntarily, such as blood pressure, heart rate, muscle tension, and skin temperature. As used herein, "biofeedback" refers to a technique in which subjects are trained to improve their health by using signals from their own bodies to control their own physiological responses.

In one embodiment of the invention, a subject suffering from chronic pain undergoes biofeedback sessions to help alleviate the pain. Upon the conclusion of each session wherein the subject has made progress in learning/developing responses that reduce the chronic pain, the subject is administered a compound of the invention on a post-extinction training pre-sleep basis in order to consolidate the desired learning.

In another embodiment, a subject suffering from phantom limb syndrome undergoes thermal biofeedback sessions to reduce and hopefully eliminate the symptoms. After each session, the subject is administered a therapeutically effective formulation of a compound of the invention on a post-extinction training pre-sleep basis.

In another embodiment, extinction training can be provided by physical therapy, or virtual reality physical therapy such as virtual reality gait therapy. For example, a stroke victim re-learning how to walk can undergo virtual reality gait therapy, and then be administered a compound of the invention on an achronic, post-extinction training pre-sleep basis.

Another form of extinction training can be provided by pharmacotherapy. For example, a man afflicted with erectile dysfunction can have an extinction learning event based on a positive sexual outcome, including instances wherein the positive sexual outcome was achieved with the pharmacological assistance of a PDE-5 inhibitor such as sildenafil, tadalafil, vardenafil, and/or udenafil. By administering a compound of the invention on a post-extinction training pre-sleep basis to a subject with erectile dysfunction, following a successful sexual outcome wherein the subject utilized sildenafil, the heightened confidence and reduced sexual performance anxiety resulting from a successful outcome can be consolidated in said subject's psyche, thereby facilitating extinction of any deleterious performance anxiety associated with sexual intercourse.

Extinction training does not always require intervention of a trained specialist. Individuals can carry out extinction training on themselves.

Fungal Diseases or Infections

In some aspects, the invention relates to a method for treating, alleviating, and/or preventing a fungal disease or infection comprising administering to a subject a compound of the invention. The invention provides a method for treating, alleviating, and/or preventing a hospital-acquired fungal infections that attack immunocompromised patients including those with HIV and cancer. In one embodiment, the invention provides a method for treating, alleviating, and/or preventing a fungal disease in a subject not suffering from cancer.

Inflammatory Disease

In some aspects, the invention relates to a method for treating, alleviating, and/or preventing an inflammatory disease, including but not limited to stroke, rheumatoid arthritis, lupus erythematosus, ulcerative colitis and traumatic brain injuries (Leoni et al., PNAS, 99(5); 2995-3000(2002); Suuronen et al. J. Neurochem. 87; 407-416 (2003) and Drug Discovery Today, 10: 197-204 (2005).

Neoplastic Diseases

In some aspects, the invention relates to methods of selectively inducing terminal differentiation, and arresting cell growth and/or apoptosis of neoplastic cells, thereby inhibiting proliferation of such cells. The compounds of the present invention are useful in treating, alleviating, and/or preventing cancer in a subject.

The term "cancer" refers to any cancer caused by the proliferation of neoplastic cells, such as solid tumors, neoplasms, carcinomas, sarcomas, leukemias, lymphomas and the like. In particular, cancers that may be treated, alleviated and/or prevented by the compounds of the invention include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer.

In some embodiments, the compounds of the invention relate to treating, alleviating, or preventing cardiac cancers selected from sarcoma (angiosarcoma, fibrosarcoma, rhabdomyosarcoma, liposarcoma), myxoma, rhabdomyoma, fibroma, lipoma and teratoma.

In some embodiments, the compounds of the invention relate to treating, alleviating, or preventing lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma.

In some embodiments, the compounds of the invention relate to treating, alleviating or preventing gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), and large bowel (adenocarcinoma, tubular adenoma, villous adenoma, hamartoma, leiomyoma).

In some embodiments, the compounds of the invention relate to treating, alleviating, and/or preventing genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

In some embodiments, the compounds of the invention relate to treating, alleviating, and/or preventing liver cancer selected from hepatoma (hepatocellular carcinoma), cholangiocarcinoma, hepatoblastoma, angiosarcoma, hepatocellular adenoma, and hemangioma.

In some embodiments, the compounds of the invention relate to treating, alleviating, and/or preventing bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors.

In some embodiments, the compounds of the invention relate to treating, alleviating, and/or preventing nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In some embodiments, the compounds of the invention relate to treating, alleviating, and/or preventing gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In some embodiments, the compounds of the invention relate to treating, alleviating, and/or preventing skin cancer selected from malignant melanoma, basal cell carcinoma, squamous cell carcinoma, Karposi's sarcoma, moles dysplastic nevi, lipoma, angioma, dermatofibroma, keloids, and psoriasis.

In some embodiments, the compounds of the invention relate to methods of treating, alleviating, and/or preventing adrenal gland cancer selected from neuroblastoma.

In some embodiments, the instant compounds are useful in the treatment, alleviation, and/or preventing of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

Hematologic Diseases

In some aspects, the invention relates to methods of treating, alleviating, or preventing hematolical diseases. Hematologic diseases include abnormal growth of blood cells which can lead to dysplastic changes in blood cells and hematologic malignancies such as various leukemias. Examples of hematologic diseases include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Sickle cell disease is attributable to homozygous inheritance of a single amino acid substitution in the β-globin gene that leads to polymerization of deoxygenated hemoglobin, deformation of red blood cells, microvascular occlusion, hemolysis, and consequent disease manifestations, including pain, strokes, and pulmonary complications (Bunn H F, 1997, J. Med. 337:762-769). Abundant biochemical, epidemiological, and clinical evidence have shown that a high level of γ globin, the fetal form of β globin, inhibits the aberrant polymerization of sickle hemoglobin and ameliorates the disease phenotype. The only Food and Drug Administration (FDA)-approved drug for sickle cell disease, hydroxyurea, causes significant induction of fetal hemoglobin, decreased disease severity, and benefits overall mortality (Letvin et al., 1984, N Engl J Med 310:869-873; Platt O S, et al., 1984, J Clin Invest 74:652-656; Charache S, et al., 1995, N Engl J. Med 332: 317-1322; Steinberg M H, et al., 2003, JAMA 289:1645-1651). Nevertheless, hydroxyurea has bone marrow-suppressive effects and is ineffective in a significant portion of patients (Charache S, et al.; Steinberg M H, et al., 2003; Steinberg M H, 1999, N Engl J. Med 340:1021-1030). A drug that induces fetal hemoglobin more substantially with less myelosuppression would be expected to have greater therapeutic utility in sickle cell disease.

Transcriptional regulation of the human globin gene locus has been investigated intensively. Gamma-globin gene expression is influenced by transcription factors (GATA-1, EKLF, NF-E4p22, Ikaros) and chromatin modifying enzymes [SWI/SNF complex, HATs, and histone deacetylase (HDACs)] as part of multiprotein complexes, and a unique, dynamic chromatin structure termed the β-globin active chromatin hub ((SACH) (8-11). Polymorphisms in BCL11A, a transcriptional repressor, alter baseline fetal hemoglobin levels, and a multiprotein complex containing BCL11a binds to the β-globin locus, resulting in repression of γ-globin expression (Menzel S, et al., 2007, Nat Genet 39:1197-1199; Lettre G, et al., 2008, Proc Natl Acad Sci USA 105:11869-11874;

Sankaran V G, et al., 2008, Science 322:1839-1842; Uda M, et al., 2008, Proc NATL Acad Sci USA 105:1620-1625; Sankaran V G, et al., 2009, Nature 460:1093-1097). Despite this granularity, discrete targets amenable to ligand discovery efforts have not been identified and functionally validated.

The induction of fetal hemoglobin is a validated strategy to improve symptoms and complications of sickle cell disease. The development of targeted therapies has been limited by the absence of discrete druggable targets. Bradner et al., 2010, PNAS, 107:28, 12617-12622 has developed a unique bead-based strategy for the identification of inducers of fetal hemoglobin transcripts in primary human erythroid cells, which includes a small-molecule screen of bioactive compounds that have been identified to have remarkable class-associated activity among histone deacetylase (HDAC) inhibitors. Using a chemical genetic strategy combining focused libraries of biased chemical probes and reverse genetics by RNA interference, Bradner et al. identified HDAC1 and HDAC2 as molecular targets mediating fetal hemoglobin induction. Isoform-selective inhibitors of HDAC1 and HDAC2 are targets for the treatment of sickle cell disease.

Pharmaceutical Compositions

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of HDAC (e.g., HDAC2).

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents. In other embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Those additional agents may be administered separately from a provided combination therapy, as part of a multiple dosage regimen. Alternatively, those agents may be part of a single dosage form, mixed together with a compound of this invention in a single composition. If administered as part of a combination therapy, the two therapeutic agents may be submitted simultaneously, sequentially or within a period of time from one another normally within about one through twelve hours from one another. For example, one therapeutic agent can be administered within about one, two, three, four, five, six, seven, eight, nine, ten, eleven, or twelve hours from the other therapeutic agent or agents used in the combination therapy.

Combination therapy can be used for any of the therapeutic indications described herein. In one aspect, the invention provides a method, wherein the method is a combination therapy further comprising administering to the subject (1) a pharmaceutically active ingredient or exposing the subject to (2) cognitive behavioral therapy (CBT), (3) psychotherapy, (4) behavioral exposure treatments, (5) virtual reality exposure (VRE) or (6) cognitive remediation therapy or (7) any combination thereof. In one aspect, the invention provides a combination therapy for treating, alleviating, and/or preventing post-traumatic stress disorder (PTSD) or Alzheimer's disease in a subject comprising administering to the subject in need thereof an effective amount of (1) a compound of the invention or a pharmaceutically acceptable salt, hydrate, solvate, or prodrug thereof and (2) a pharmaceutically active ingredient administered selected from Aricept®, memantine, and galantamine.

In one aspect, the invention provides a method of treating extinction learning disorders in a subject in need thereof comprising administering to the subject an effective amount of a compound of the invention or a pharmaceutically acceptable salt, hydrate, solvate, or prodrug thereof. In one aspect, the extinction learning disorder is fear extinction deficit. In one aspect, the extinction learning disorder is post-traumatic stress disorder. In one aspect, the method is a combination therapy for treating extinction learning disorders in a subject in need thereof comprising administering to the subject (1) an effective amount of a compound of the invention or a pharmaceutically acceptable salt, hydrate, solvate, or prodrug thereof and (2) exposing the subject to cognitive behavioral therapy (CBT), psychotherapy, behavioral exposure treatments, virtual reality exposure (VRE) or cognitive remediation therapy.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

Another aspect of the invention relates to inhibiting HDAC activity in a biological sample or a patient, which method comprises administering to the patient, or contacting said biological sample with a compound described herein, or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where HDAC plays a role.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Information

Spots were visualized by UV light (254 and 365 nm). Purification by column and flash chromatography was carried out using silica gel (200-300 mesh). Solvent systems are reported as the ratio of solvents.

NMR spectra were recorded on a Bruker 400 (400 MHz) spectrometer. $^1H$ chemical shifts are reported in δ values in ppm with tetramethylsilane (TMS, =0.00 ppm) as the internal standard. See, e.g., the data provided in Table 1.

LCMS spectra were obtained on an Agilent 1200 series 6110 or 6120 mass spectrometer with ESI (+) ionization mode. See, e.g., the data provided in Table 1.

Example 1. Synthesis of Compound 136

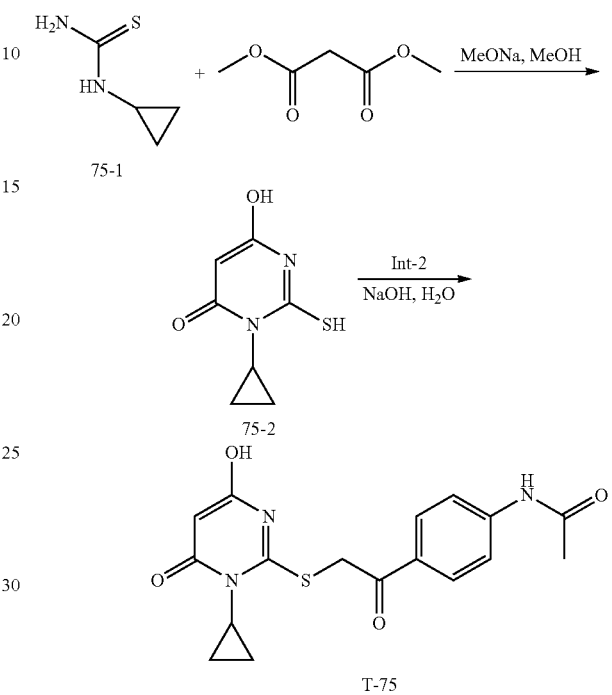

Synthesis of Intermediate Int-2

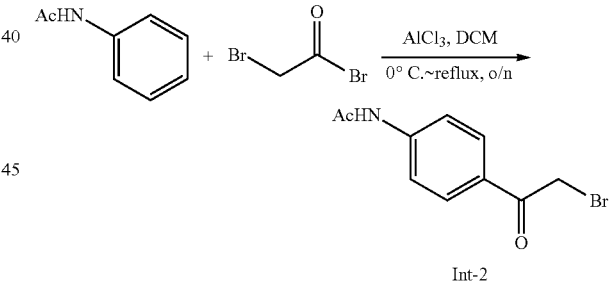

To a solution of N-phenylacetamide (4.1 g, 30 mmol) in DCM (50 mL) was added bromoacetyl bromide (7.3 g, 30 mmol). After the solution was cooled in an ice bath, $AlCl_3$ (9.0 g, 67 mmol) was added in three portions. The mixture was refluxed overnight, cooled and poured into ice cold water. The formed precipitate was filtered and washed with water to give the Int-2 (4.3 g, 55%) as a yellow solid.

Synthesis of 75-2.

To a mixture of 75-1 (580 mg, 5.0 mmol) and dimethyl malonate (726 mg, 5.5 mmol) in MeOH (50 mL) was added MeONa (540 mg, 10 mmol). The reaction mixture was stirred at 80° C. for 5 h. The solvent was removed under reduced pressure and then diluted with water (20 mL). The resultant was adjusted to pH=6 with diluted HCl solution. The formed precipitate was filtered off to give 75-2 (450 mg, 49%) as a white solid.

Synthesis of T-75 (Compound 136).

To a stirred solution of 75-2 (276 mg, 1.5 mmol) and NaOH (120 mg, 3.0 mmol) in $H_2O$ (6 mL) was added Int-2 (382 mg, 1.5 mmol) in THF (2 mL) dropwise. The solution was stirred at r.t. for 2 h and then adjusted to pH=6 with diluted HCl solution. The formed precipitate was filtered off to give Compound 136 (123 mg, 23%) as a white solid.

Compounds 131 and 132 were synthesized in a similar manner using the appropriately substituted amine variant of 75-1.

Compound 131.

110 mg, 19%, a white solid.

Compound 132.

90 mg, 15%, a white solid.

Example 2. Synthesis of Compound 133

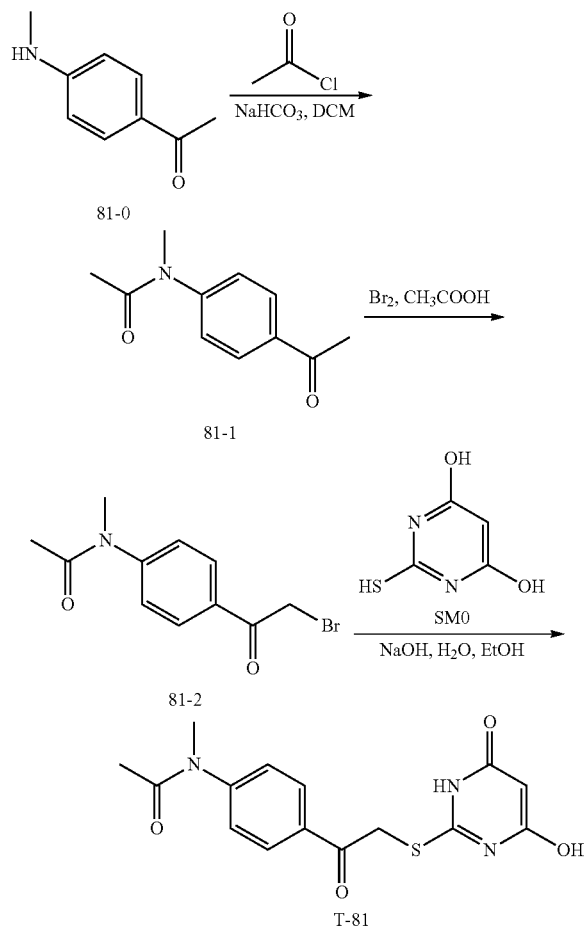

Synthesis of 81-1.

To a mixture of 81-0 (1.00 g, 6.7 mmol), NaHCO$_3$ (1.68 g, 20.0 mmol) in DCM (15 mL) was added acetyl chloride (790 mg, 10.0 mmol) dropwise in an ice bath. The mixture was stirred at r.t overnight and water (30 mL) was then added. The resultant mixture was extracted with DCM. The combined organic layers were washed with brine, dried over anhydrous $Na_2SO_4$, and concentrated to give 81-1 (1.12 g, 87%) as a light yellow oil, which was used directly to next step without further purification.

Synthesis of 81-2.

To a solution of 81-1 (1.12 g, 5.8 mmol) in acetic acid (15 ml) was added $Br_2$ (928 mg, 5.8 mmol) dropwise. The mixture was stirred at 60° C. for 3 h, cooled and then poured into water. The resultant was extracted with EA. The organic phase was washed with sat. $NaHCO_3$ solution followed by brine, dried over anhydrous $Na_2SO_4$ and concentrated. The residue was purified by column chromatography on silica gel (DCM:MeOH=100:1) to give pure 81-2 (428 mg, 27%) as a yellow solid.

Synthesis of T-81 (Compound 133).

To a stirred solution of SM0 (230 mg, 1.6 mmol) and NaOH (128 mg, 3.2 mmol) in $H_2O$ (5 mL) and ethanol (3 mL) was added 81-2 (428 mg, 1.6 mmol) in one portion. The solution was stirred at r.t. for 2 hr and then adjusted to pH=6 with diluted HCl solution. The formed precipitate was filtered and washed with methanol to give Compound 133 (100 mg, 19%) as a white solid.

Example 3. Synthesis of Compound 137

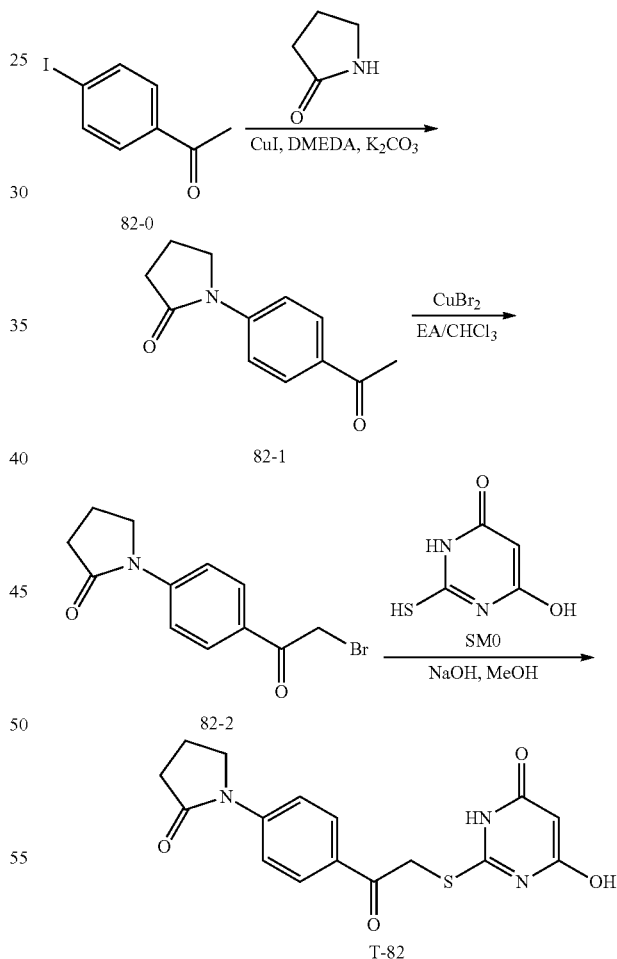

Synthesis of 82-1.

To a mixture of 82-0 (2.46 g, 10 mmol) and pyrrolidin-2-one (854 mg, 10 mmol) in dioxane (100 mL) was added CuI (380 mg, 2 mmol), DMEDA (176 mg, 2 mmol), and $K_2CO_3$ (2.76 g, 20 mmol). The reaction mixture was stirred at 100° C. for 4 h. The solvent was evaporated and water was added. The resulting mixture was extracted with EA. The organic extracts were combined, dried over MgSO₄, filtered and concentrated. The residue was purified by column chromatography on silica gel (PE:EA=2:1) to give 82-1 (1.50 g, 74%) as a white solid.

Synthesis of 82-2.

To a stirred solution of 82-1 (1.50 g, 7.4 mmol) in EA/CHCl₃ (50 mL, 1:1) was added CuBr₂ (1.80 g, 8.1 mmol). The reaction mixture was stirred at 70° C. overnight. After the reaction was completed, the solvent was evaporated and water was added. The resulting mixture was extracted with EA. The organic extracts were combined, dried over MgSO₄, filtered and concentrated. The residue was purified by column chromatography on silica gel (PE:EA=3:1) to give 82-2 (750 mg, 36%) as a yellow solid.

Synthesis of T-82 (Compound 137).

To a stirred solution of SM0 (180 mg, 1.25 mmol) and NaOH (100 mg, 2.50 mmol) in H₂O (6 mL) was added 82-2 (350 mg, 1.25 mmol) in THF (2 mL) dropwise in 2 min. The solution was stirred at r.t. for 2 h and then adjusted to pH=6 with diluted HCl solution. The formed precipitate was filtered to give Compound 137 (120 mg, 28%) as a yellow solid.

Example 4. Synthesis of Compound 134 and stirred for 6 h. The reaction mixture was poured into ice/water. The formed precipitate was collected by filtration, washed with water and air-dried to afford the pure 83-1 (1.76 g, 90%) as a yellow solid.

Synthesis of 83-2.

To a stirred solution of 83-1 (1.76 g, 5.60 mmol) in THF (10 mL) was added the solution of (EtO)₂POH (812 mg, 5.88 mmol) and TEA (594 mg, 5.88 mmol) in THF (5 mL) at 0° C. dropwise. The mixture was gradually warmed to r.t. and stirred for 6 h. The resultant was concentrated and poured into ice/water. The formed precipitate was collected by filtration, washed with water and air-dried to afford the pure 83-2 (850 mg, 63%) as a yellow solid.

Synthesis of T-83 (Compound 134).

To a stirred solution of SM0 (245 mg, 1.7 mmol) and NaOH (136 mg, 3.4 mmol) in H₂O (5 mL) and ethanol (3 mL) was added 83-2 (400 mg, 1.7 mmol) in one portion. The solution was stirred at r.t. for 2 h and then adjusted to pH=6 with diluted HCl solution. The formed precipitate was filtered and washed with methanol to give Compound 134 (100 mg, 19%) as a white solid.

Example 5. Synthesis of Compound 135

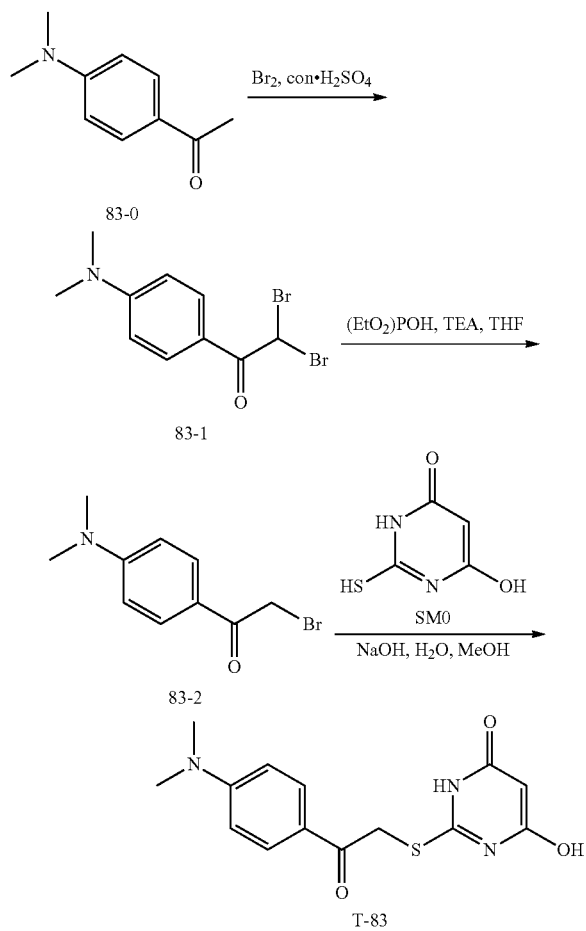

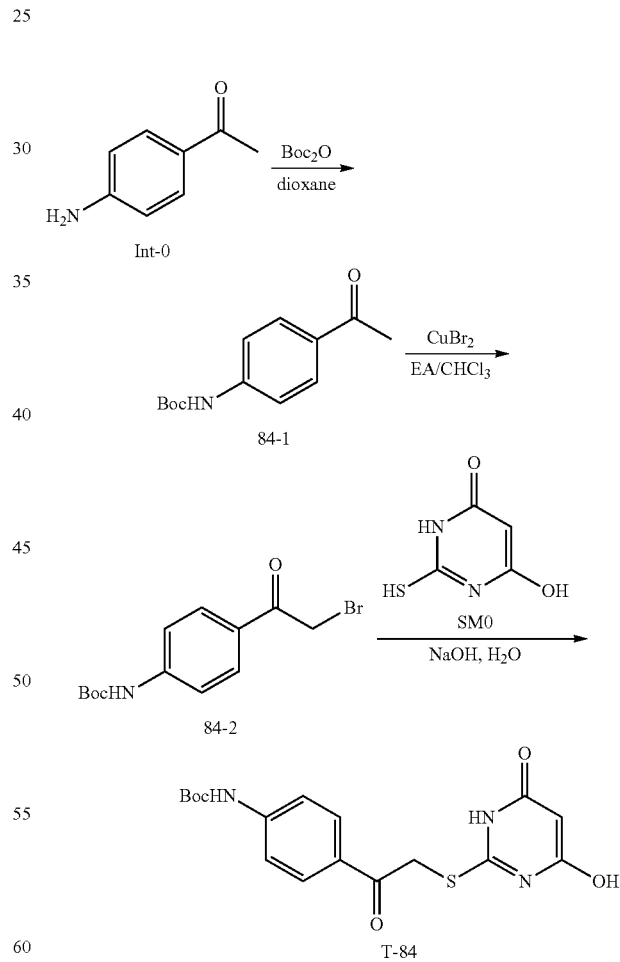

Synthesis of 83-1.

To a solution of 83-0 (1.00 g, 6.1 mmol) in con.H₂SO₄ (6 mL) was slowly added Br₂ (1.00 g, 6.1 mmol) at 0° C. with stirring. The resulting mixture was gradually warmed to r.t.

Synthesis of 84-1.

A mixture of Int-0 (1.35 g, 10 mmol) and Boc₂O (2.60 g, 12 mmol) in dioxane (20 mL) was refluxed overnight. The mixture was concentrated under reduced pressure and then re-dissolved in EA (20 mL). The solution was washed with 1 N HCl followed by sat. NaCl, dried over anhydrous Na₂SO₄, filtered, concentrated to give 84-1 (2.0 g, 85%) as a yellow solid.

Synthesis of 84-2.

The mixture of 84-1 (1.45 g, 6 mmol) and CuBr₂ (2.00 g, 9 mmol) in CHCl₃/EA (40 mL, 1:1) was refluxed for 3 h. The solvent was removed in vacuo and the residue was purified by column chromatography on silica gel (PE:EA=10:1) to give 84-2 (330 mg, 18%) as a yellow solid.

Synthesis of T-84 (Compound 135).

To a stirred solution of SM0 (144 mg, 1.0 mmol) and NaOH (80 mg, 2 mmol) in H₂O (5 mL) and ethanol (3 mL) was added 84-2 (313 mg, 1 mmol) in one portion. The solution was stirred at r.t. for 2 h and then adjusted to pH=6 with diluted HCl solution. The formed precipitate was filtered and washed with methanol to give Compound 135 (90 mg, 24%) as a yellow solid.

Example 6. Synthesis of Compound 138

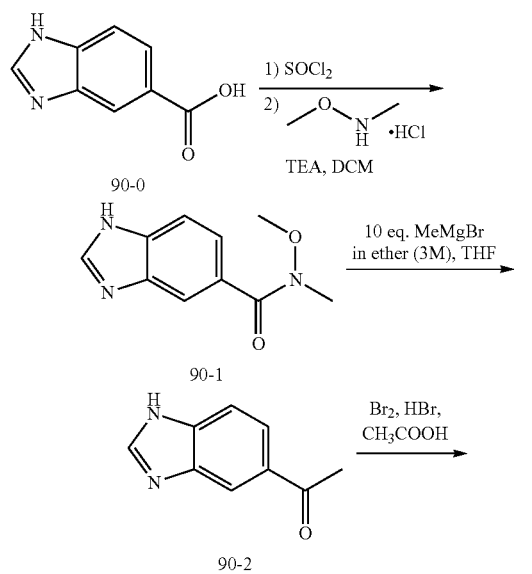

added dropwise to a solution of O,N-dimethylhydroxylamine hydrochloride (1.57 g, 16.0 mmol) and TEA (4.99 g, 50.0 mmol) in DCM (30 mL) under an ice bath. The resulting mixture was continued to stir at r.t. for 5 h and then quenched with water (20 mL). The resultant was extracted with DCM. The combined extracts were dried over anhydrous Na₂SO₄ and concentrated. The residue was purified by column chromatography on silica gel (DCM:MeOH=30:1) to give pure 90-1 (1.50 g, 59%) as an orange solid.

Synthesis of 90-2.

To a solution of 90-1 (1.5 g, 7.3 mmol) in THF (20 mL) was added a solution of MeMgBr in ether (24.3 mL, 73.0 mmol, 3 M). The mixture was heated to reflux and stirred for 2 h. After cooling to r.t., sat. NH₄Cl solution was added to quench the reaction. The resultant was extracted with EA. The combined extracts were dried over anhydrous Na₂SO₄ and concentrated in vacuo to give 90-2 (900 mg, 77%) as a light yellow solid, which was used directly to next step without further purification.

Synthesis of 90-3.

To a solution of 90-2 (433 mg, 2.7 mmol) and aq. HBr solution (48% w/w, 3.5 mL) in CH₃COOH (5.0 mL) was added the solution of Br₂ (433 mg, 2.7 mmol) in CH₃COOH (1.5 mL) at r.t. The mixture was stirred at 40° C. for 1 h and then cooled to r.t. The formed precipitate was collected by filtration and washed with water to afford the pure 90-3 (238 mg, 37%) as an orange solid.

Synthesis of T-90 (Compound 138).

To a stirred solution of SM0 (144 mg, 1.0 mmol) and NaOH (80 mg, 2.0 mmol) in H₂O (5 mL) and ethanol (3 mL) was added 90-3 (238 mg, 1.0 mmol) in one portion. The solution was stirred at r.t. for 2 h and then adjusted to pH=6 with diluted HCl solution. The formed precipitate was filtered and washed with methanol to give Compound 138 (80 mg, 26%) as an orange solid.

Example 7. Synthesis of Compound 140

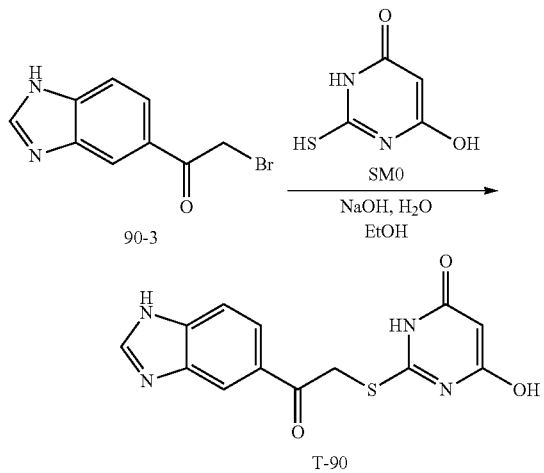

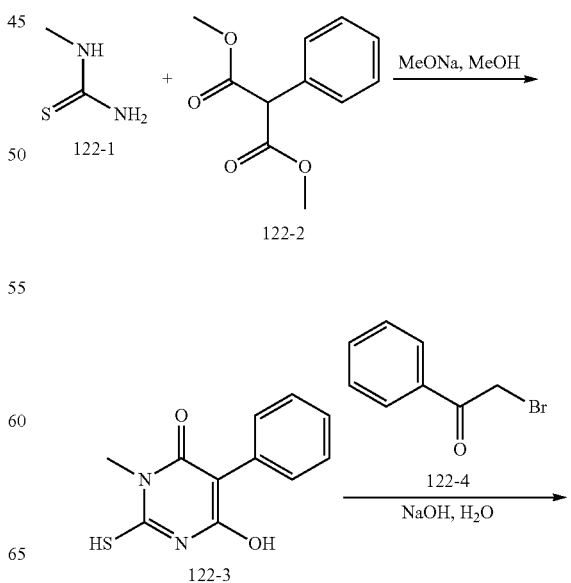

Synthesis of 90-1.

A solution of 90-0 (2.00 g, 12.3 mmol) in SOCl₂ (32 mL) was stirred at reflux for 2 h. The solution was concentrated and re-dissolved in DCM (5 mL). The above solution was

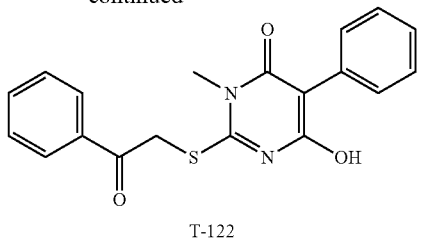

T-122

Synthesis of 122-3.

To a mixture of 122-1 (1.18 g, 5.7 mmol) and 122-2 (510 mg, 5.7 mmol) in MeOH (10 mL) was added MeONa (616 mg, 11.4 mmol). The reaction mixture was stirred at 75° C. for 4 h. The solvent were removed under reduced pressure to give a white oil. Water (20 mL) was added and the resulting solution was adjusted to pH=6 with diluted HCl solution. The formed precipitate was filtered to give 122-3 (800 mg, 60%) as a white solid.

Synthesis of T-122 (Compound 140).

To a stirred solution of 122-3 (400 mg, 1.7 mmol) and NaOH (137 mg, 3.4 mmol) in $H_2O$ (6 mL) was added 122-4 (338 mg, 1.7 mmol) in THF (2 mL) dropwise. The solution was stirred at r.t. for 2 h and then adjusted to pH=6 with diluted HCl solution. The formed precipitate was filtered to give Compound 140 (130 mg, 22%) as a white solid.

Example 8. Synthesis of Compound 141

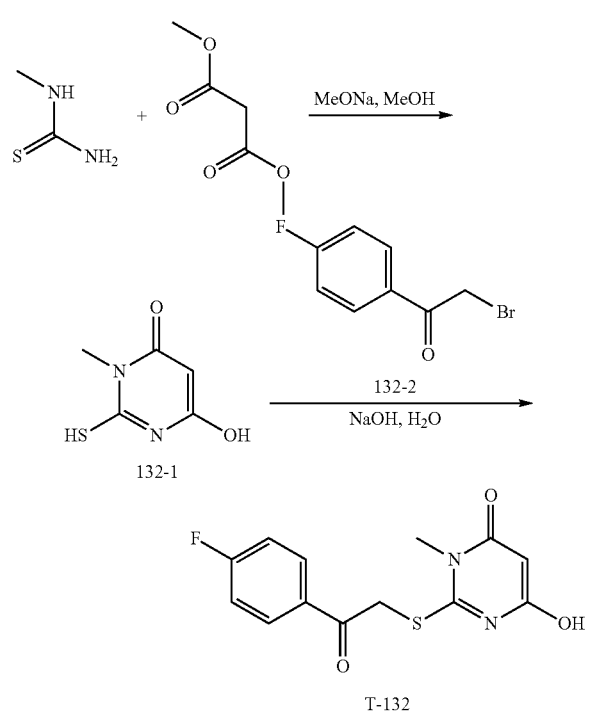

Synthesis of 132-1.

To a stirred mixture of N-methylthiourea (4.00 g, 44.4 mmol) and dimethyl malonate (6.15 g, 46.6 mmol) in MeOH (30 mL) was added NaOMe (5.04 g, 93.2 mmol). The reaction mixture was stirred at reflux for 6 h. After cooling to r.t., the solvent was removed in vacuo and water was added. The resultant was adjusted to pH=6 with diluted HCl solution. The formed precipitate was filtered and washed with water to give 132-1 (4.00 g, 56%) as a light green solid.

Synthesis of T-132 (Compound 141).

To a stirred solution of 132-1 (237 mg, 1.5 mmol) and NaOH (72 mg, 1.8 mmol) in $H_2O$ (5 mL) was added 132-2 (324 mg, 1.5 mmol) in one portion. The solution was stirred at r.t. for 2 h and then adjusted to pH=6 with diluted HCl solution. The formed precipitate was filtered and washed with methanol to give Compound 141 (75 mg, 17%) as a white solid.

Compounds 139, 142, 143, 144 were synthesized by a similar procedure using an appropriately phenyl-substituted derivative of 132-2.

Compound 139.
80 mg, 18%, a white solid.
Compound 142.
80 mg, 18%, a white solid.
Compound 143.
90 mg, 19%, a white solid.
Compound 144.
65 mg, 14%, a yellow solid.

Example 9. Synthesis of Compounds 101 and 108

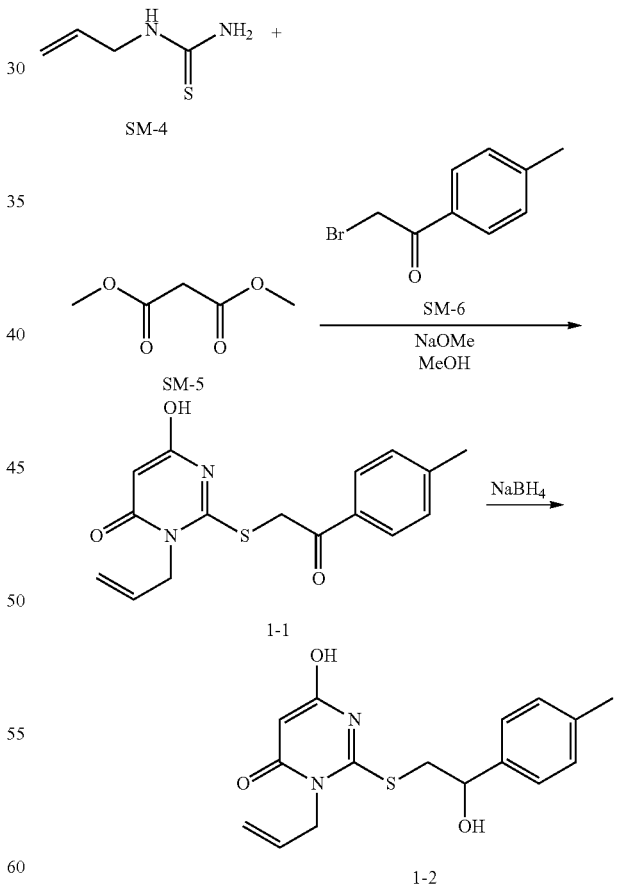

Synthesis of 1-1 (Compound 101).

To a stirred mixture of SM-4 (1.16 g, 10 mmol), SM-5 (1.32 g, 10 mmol) in MeOH (15 mL) was added NaOMe (1.14 g, 21 mmol) in MeOH (5 mL). The reaction mixture was stirred at 70° C. for 5 h and SM-6 (2.56 g, 12 mmol) was then added in portions. The resultant was stirred at 50° C. for 0.5 h. The formed precipitate was filtered off and washed with MeOH to give 1-1 (500 mg, 16%) as a white solid.

Synthesis of 1-2 (Compound 108).

To a stirred solution of 1-1 (316 mg, 1.0 mmol) in THF/MeOH (6 mL, ½) was added NaBH₄ (60 mg, 1.5 mmol). After 30 min, the solvent was evaporated and water was added. The resultant was acidified with 1 N HCl solution to pH=6-7. The formed precipitate was filtered off and washed with Et₂O to give Compound 108 (70 mg, 22%) as a light yellow solid.

The protocol used to synthesize 1-1 was also used to synthesize Compounds 112, 113, 115, 116, 117, and 118 using the appropriately substituted variants of SM-4 and SM-6 as indicated below.

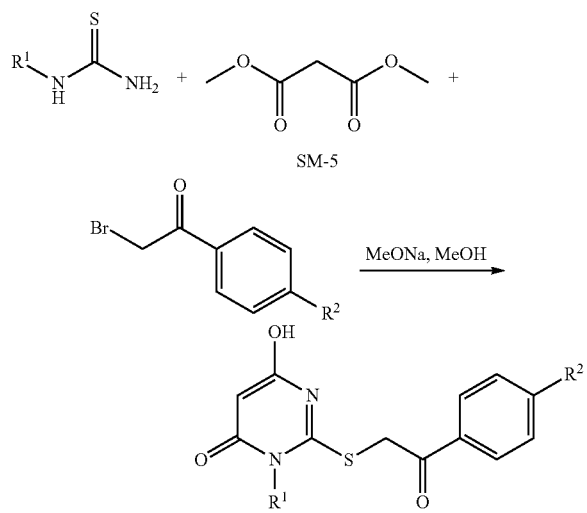

Compound 112:
R¹=R²=Me; 145 mg, 25%, a white solid
Compound 113:
R¹=i-Pr, R²=Me; 200 mg, 31%, a white solid
Compound 115:
R¹=Et, R²=Me; 210 mg, 35%, a white solid
Compound 116:
R¹=Me, R²=AcNH; 330 mg, 50%, a white solid
Compound 117:
R¹=Et, R²=AcNH; 420 mg, 60%, a yellow solid
Compound 118:
R¹=i-Pr, R²=AcNH; 380 mg, 54%, an orange solid Example 10. Synthesis of Compound 109

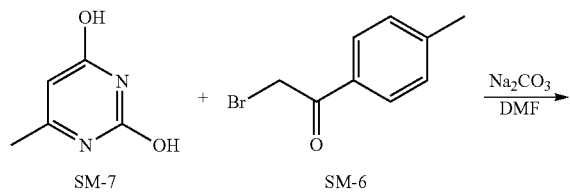

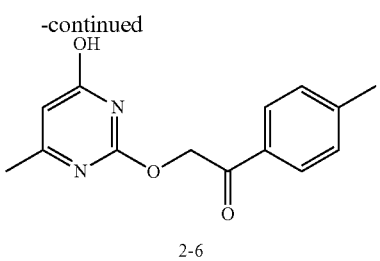

A mixture of SM-7 (300 mg, 2.4 mmol), SM-6 (425 mg, 2.0 mmol) and Na₂CO₃ (424 mg, 4.0 mmol) in DMF (10 mL) was stirred at r.t. overnight. The resulting mixture was filtered and the filtrate was concentrated. The residue was purified by prep. HPLC to give 2-6 (Compound 109; 260 mg, 51%).

Example 11. Synthesis of Compound 114

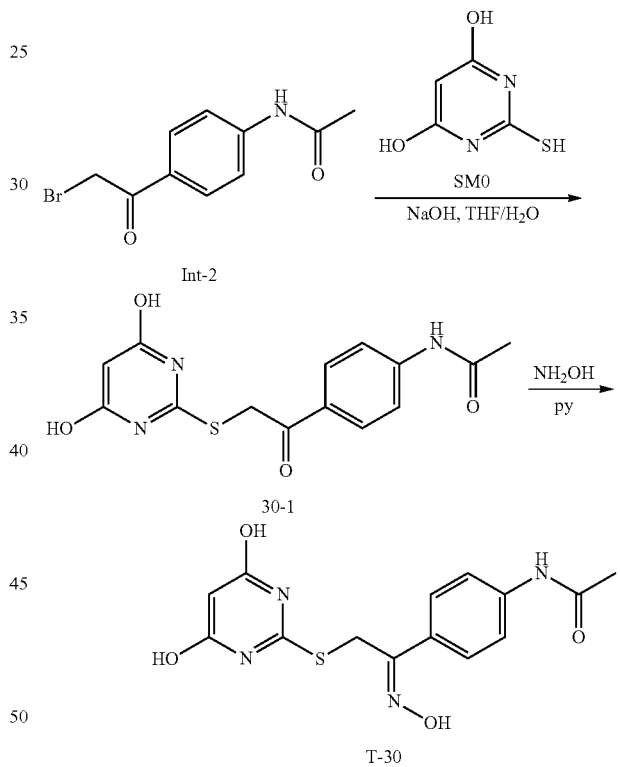

Synthesis of 30-1.

To a stirred solution of SM0 (113 mg, 0.79 mmol) and NaOH (63 mg, 1.56 mmol) in H₂O (6 mL) was added Int-2 (200 mg, 0.78 mmol) in THF (2 mL) dropwise. The solution was stirred at r.t. for 2 h and then adjusted to pH=2-3 with 1 N HCl solution. The formed precipitate was filtered to give 30-1 (200 mg, 80%) as a yellow solid.

Synthesis of T-30 (Compound 114).

To a stirred mixture of 30-1 (200 mg, 0.63 mmol) and NH₂OH (130 mg, 1.90 mmol) in MeOH (5 mL) was added pyridine (743 mg, 9.40 mmol). The reaction mixture was stirred at 80° C. for 4 h. The solvent was removed and water was added. The resultant was adjusted to pH=2-3 with 1 N HCl solution. The formed precipitate was filtered off to give Compound 114 (98 mg, 47%) as a white solid.

Example 12. Synthesis of Compound 123

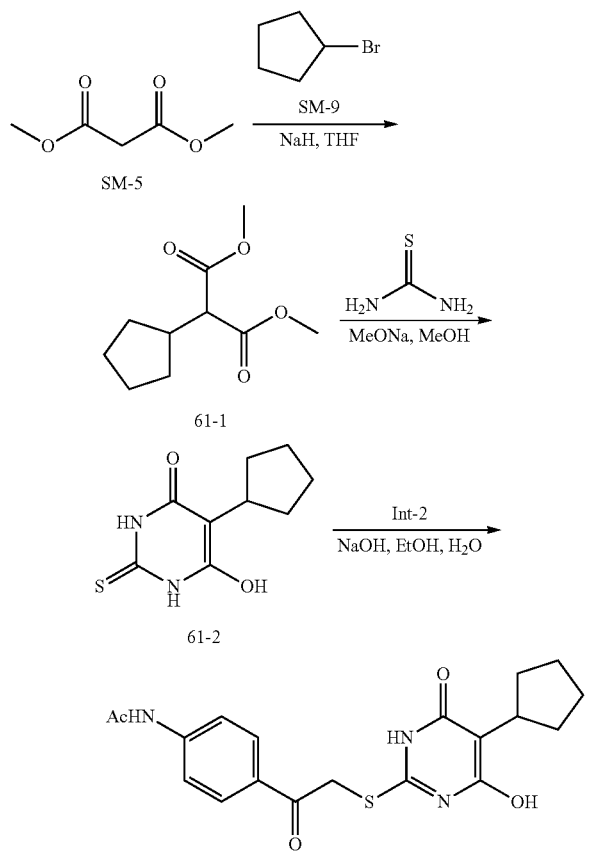

Synthesis of 61-1.

To a solution of SM-5 (1.65 g, 12.5 mmol) in THF (20 mL) was added NaH (850 mg, 21.3 mmol) in portions under an ice bath. The mixture was warmed to r.t. and stirred for 15 min. SM-9 (2.60 g, 17.5 mmol) was then added and the resulting solution was heated to reflux for 16 h. After cooling to r.t., water (30 mL) was added and the mixture was extracted with EA. The organic phase was dried over $Na_2SO_4$, filtered and concentrated to give crude 61-1 (1.35 g, 54%), which was used directly in the next step without further purification.

Synthesis of 61-2.

A solution of thiourea (514 mg, 6.75 mmol), MeONa (730 mg, 13.50 mmol) and 61-1 (1.35 g, 6.75 mmol) in methanol (10 mL) was stirred at reflux for 5 h. After cooling to r.t., the solvent was removed in vacuo and water (5 mL) was added. The resultant was adjusted to pH=7 with 1N HCl solution. The formed precipitate was filtered off to give 61-2 (240 mg, 17%) as a white solid.

Synthesis of T-61 (Compound 123).

To a stirred solution of 61-2 (240 mg, 1.13 mmol) and NaOH (91 mg, 2.26 mmol) in $H_2O$ (5 mL) and ethanol (3 mL) was added Int-2 (290 mg, 1.13 mmol) in one portion. The solution was stirred at r.t. for 2 h and then adjusted to pH=7 with 1N HCl solution. The formed precipitate was filtered off and washed with methanol to give Compound 123 (70 mg, 16%) as a yellow solid.

Example 13. Synthesis of Compound 124

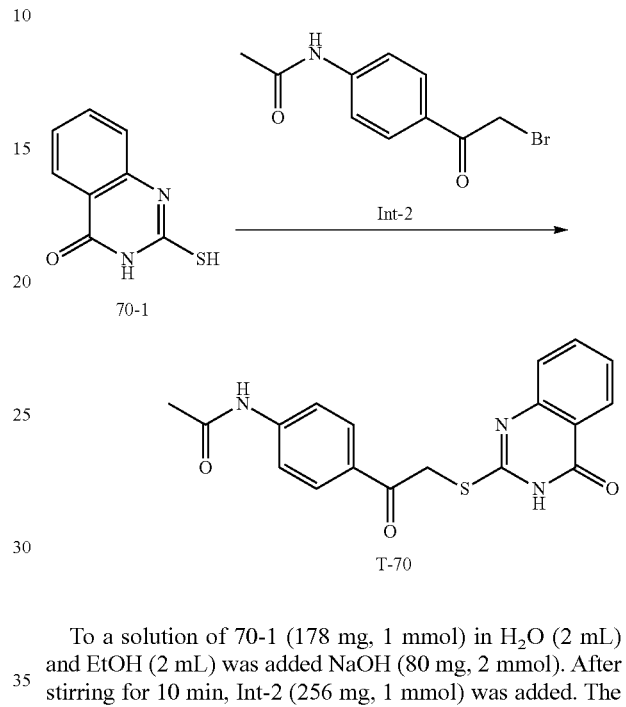

To a solution of 70-1 (178 mg, 1 mmol) in $H_2O$ (2 mL) and EtOH (2 mL) was added NaOH (80 mg, 2 mmol). After stirring for 10 min, Int-2 (256 mg, 1 mmol) was added. The reaction mixture was continued to stir at r.t. for 2 h and then adjusted to pH=5 with 1N HCl solution. The resultant was stirred for additional 10 min. The precipitate was filtered off, washed with water and further purified by trituration in $CH_3CN$ to give T-70 (Compound 124; 110 mg, 31%) as a yellow solid.

Example 14. Synthesis of Compound 121

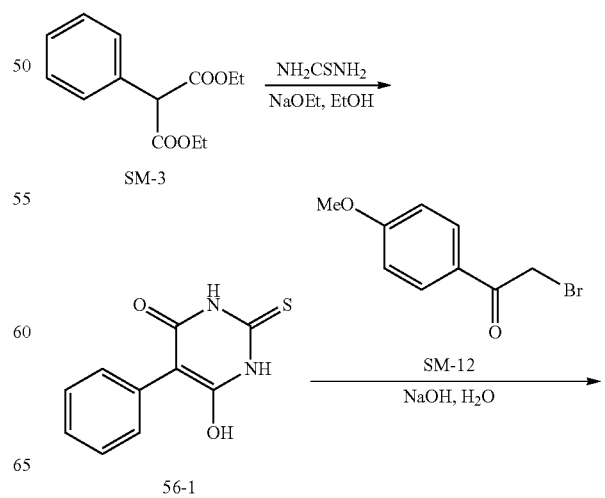

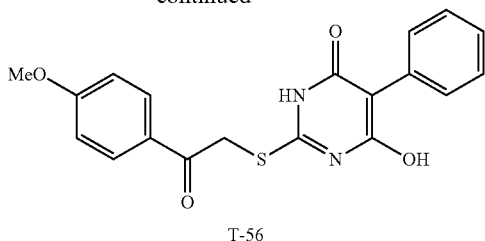

T-56

Synthesis of 56-1.

To a stirred solution of SM-3 (11.8 g, 50 mmol), thiocarbamide (3.8 g, 50 mmol) in EtOH (100 mL) was added NaOEt (3.4 g, 50 mmol). The solution was stirred at reflux overnight. After cooling to r.t., the solution was concentrated to 30 mL. Water (20 ml) was added and the resultant was acidified by 1 N HCl solution to pH=6. The precipitate was filtered off and washed with water to give 56-1 (3.4 g, 31%) as a white solid.

Synthesis of T-56 (Compound 121).

To a stirred solution of 56-1 (220 mg, 1 mmol) and NaOH (80 mg, 2 mmol) in H₂O (4 ml) was added the solution of SM-12 (228 mg, 1 mmol) in EtOH (2 ml) dropwise. The solution was stirred at r.t. for 2 h and then adjusted to pH=7 with 1 N HCl solution. The formed precipitate was filtered off and washed with water to give Compound 121 (100 mg, 27%) as a yellow solid.

Compounds 119, 122, 125 and 126 were similarly synthesized using an appropriately substituted variant of SM-3.

Synthesis of Compound 125:

For Compound 125, intermediate 60-2 was used in place of SM-3.

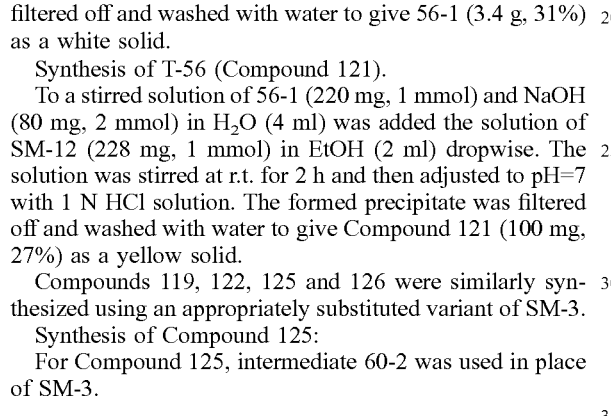

To a solution of 60-0 (1.35 g, 10.0 mmol) and NaHCO3 (1.68 g, 20.0 mmol) in DCM (50 mL) was added benzoyl chloride (10.5 mmol) dropwise at 0° C. After the addition, the reaction mixture was warmed to r.t. and stirred for 2 h. The resulting solution was quenched by water. The mixture was concentrated under the reduced pressure. Water (20 mL) was added and the resultant was stirred for 5 min. The solid was filtered off, washed with water and dried to give 60-1 (2.30 g, 98%) as a white solid.

To a solution of 60-1 (17.2 g, 72.0 mmol) in CH₃COOH (50 mL) was added Br₂ (12.2 g, 75.9 mmol) dropwise at 0° C. After the addition, the reaction mixture was heated to 60° C. and stirred for 15 h. After cooling to room temperature, the mixture was poured into ice/water (100 mL) and the resultant was continued to stir for 5 min. The formed precipitate was filtered off and further purified by column chromatography on silica gel (PE:EA=2.5:1) gave 60-2 (12.6 g, 57%) as a yellow solid.

Yield of Compound 125 was 160 mg, 54%, a yellow solid.

Synthesis of Compound 126:

For Compound 126, intermediate 58-2 was used in place of SM-3.

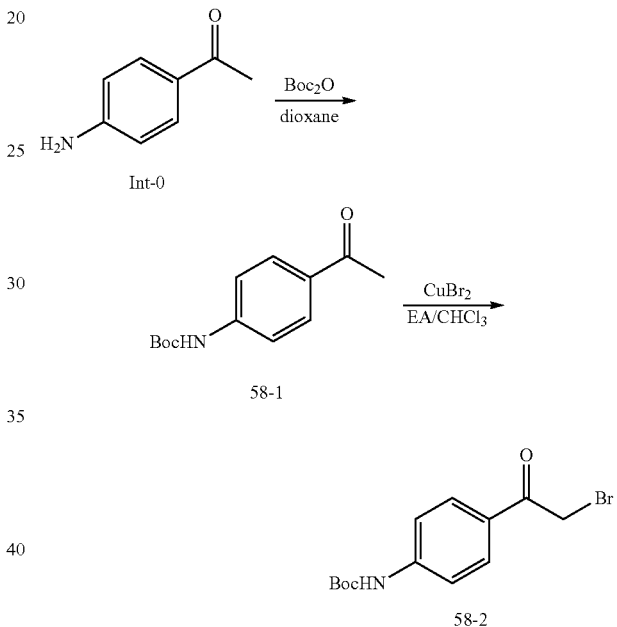

A mixture of Int-0 (1.35 g, 10 mmol) and Boc₂O (2.60 g, 12 mmol) in dioxane (20 mL) was refluxed overnight. The mixture was concentrated under the reduced pressure and EA (20 mL) was added. The resultant was washed with 1 N HCl solution and sat. NaCl solution. The organic phase was dried over Na₂SO₄ and concentrated to give 58-1 (2.00 g, 85%) as a yellow solid.

The mixture of 58-1 (1.45 g, 6 mmol) and CuBr₂ (2.00 g, 9 mmol) in CHCl₃/EA (40 mL, 1:1) was refluxed for 3 h. The solvent was removed in vacuo and the residue was purified by column chromatography on silica gel (PE:EA=10:1) to give 58-2 (330 mg, 18%) as a yellow solid.

The final yield of Compound 126 was 70 mg, 15%, a white solid. Other compounds of this example had the following yields.

Compound 119:

120 mg, 50%, a yellow solid.

Compound 122:

85 mg, 24%, a yellow solid.

Example 15. Synthesis of Compound 120

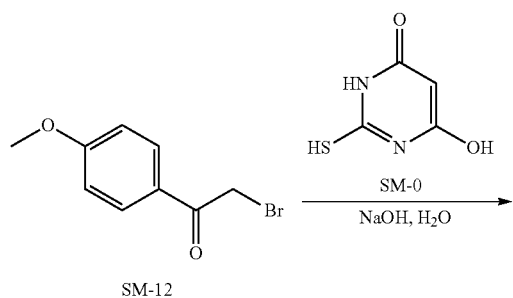

To a stirred solution of SM0 (144 mg, 1 mmol) and NaOH (80 mg, 2 mmol) in $H_2O$ (6 ml) was added the solution of SM-12 (228 mg, 1 mmol) in EtOH (2 mL) dropwise. The solution was stirred at r.t. for 2 h and then adjusted to pH=7 with 1 N HCl solution. The formed precipitate was filtered off and washed with water to give T-55 (Compound 120; 142 mg, 49%) as a pale white solid.

Compounds 107, 127, 128, 129 and 130 were synthesized by a similar protocol using an appropriately substituted variant of SM-12. The synthesis of certain of these variants is disclosed below.

Synthesis of Compound 128:
Intermediate 86-1 was used in place of SM-12.

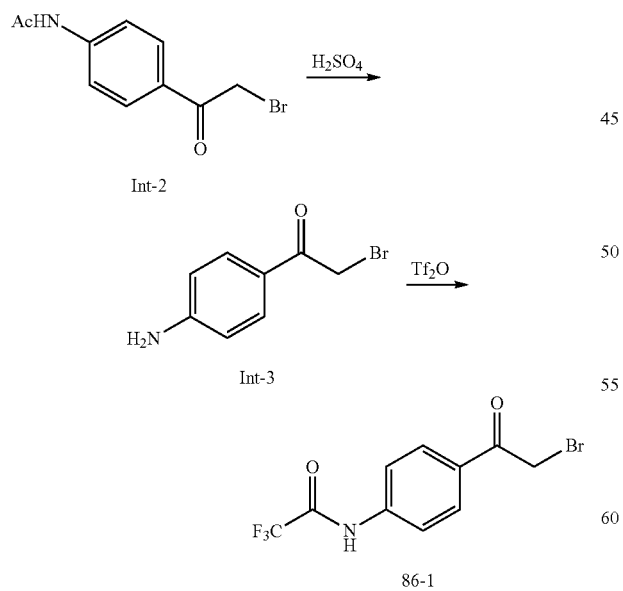

A mixture of Int-2 (765 mg, 3 mmol) in $H_2SO_4$ (6 N, 10 mL) and MeOH (10 mL) was refluxed for 2.5 h. The solvent was removed in vacuo. To the residue was added water and sat. $NaHCO_3$ solution successively to prepare a weak basic solution. The precipitate was filtered off to give the Int-3 (400 mg, 63%) as a gray solid.

A mixture of Int-3 (213 mg, 1 mmol) and TFAA (210 mg, 1 mmol) in THF (10 mL) was stirred at r.t overnight. The mixture was diluted with ethyl acetate, washed with water and sat. NaCl. The organic phase was dried over anhydrous $Na_2SO_4$ and concentrated to give 86-1 (200 mg, 65%) as a brown solid.

Compound 128 yield was 70 mg, 20%, a yellow solid.

Synthesis of Compound 129:
Intermediate 87-1 was used in place of SM-12.

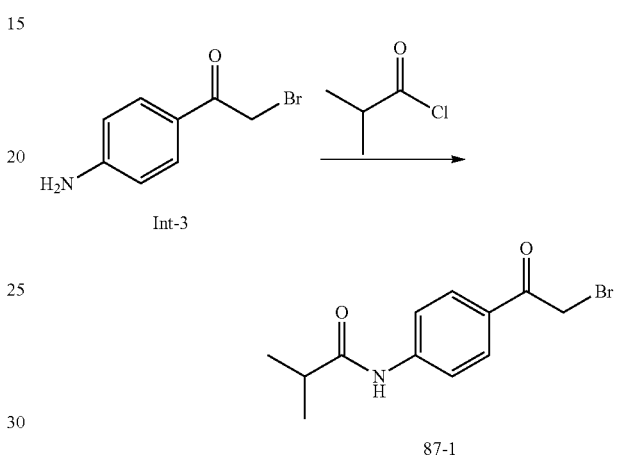

To a solution of Int-3 (430 mg, 2 mmol) and $NaHCO_3$ (336 mg, 4 mmol) in DCM (10 mL) was added isobutyryl chloride (220 mg, 2 mmol) dropwise at 0° C. After the addition, the reaction mixture was warmed to r.t. and stirred for 4 h. The resulting solution was quenched by water. The mixture was concentrated under the reduced pressure. Water (20 mL) was added and the resultant was stirred for 5 min. The solid was filtered off, washed with water and dried to give 87-1 (360 mg, 63%) as a yellow solid.

Compound 129 yield was 110 mg, 35%, a yellow solid.

Yield for the other compounds of this Example were as follows:

Compound 107:
950 mg, 43%, as a white solid.
Compound 127:
100 mg, 36%, a yellow solid.
Compound 130:
130 mg, 62%, a yellow solid.

Example 16. Synthesis of Compound 109

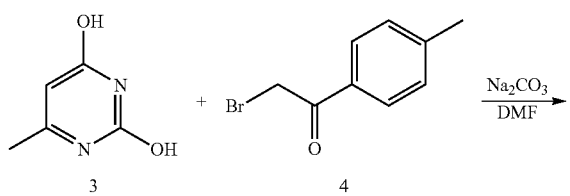

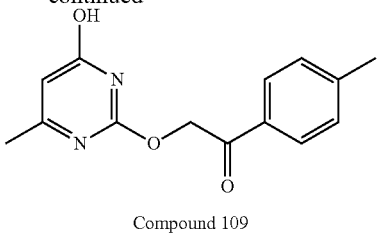

Compound 109

A mixture of 3 (150 mg, 1.2 mmol), 4 (213 mg, 1.0 mmol) and Na₂CO₃ (212 mg, 2.0 mmol) in DMF (5 mL) was stirred at r.t. overnight. The resulting mixture was filtered and the filtrate was concentrated. The residue was purified by prep. HPLC to give the Compound 109 (260 mg).

Example 17. Synthesis of Compound 145

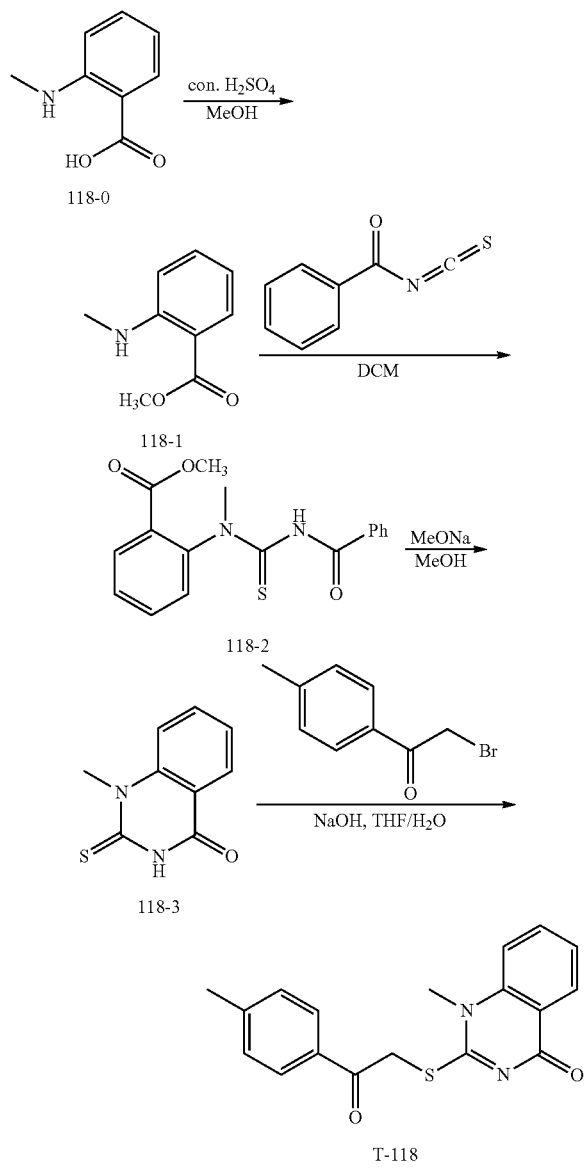

Synthesis of 118-1.

A solution of 118-0 (3.00 g, 20.0 mmol) and con.H₂SO₄ (1 mL) in MeOH (20 mL) was heated at reflux overnight. The solvent was removed in vacuo. The residue was dissolved with EtOAc (50 mL). The resulting solution was washed with sat.NaHCO₃ (30 mL×3) and brine (30 mL×3). The organic layer was dried over anhydrous Na₂SO₄ and then concentrated to give 118-1 (1.0 g, 30%) as a yellow solid.

Synthesis of 118-2.

A solution of 118-1 (700 mg, 4.3 mmol) and benzoyl isothiocyanate (733 mg, 4.5 mmol) in DCM (15 mL) was stirred at r.t. for 2 h. The precipitate was filtered off and washed with DCM (5 mL) to give (800 mg, 57%) as a white solid.

Synthesis of 118-3.

To a solution of 118-2 (800 mg, 2.4 mmol) in MeOH (10 mL) was added MeONa (270 mg, 5 mmol). The mixture was heated at reflux for 2 h. The solvent was removed in vacuo. The residue was diluted with water (5 mL) and the resultant was adjusted to pH=6 with 1 N HCl. The formed precipitate was filtered off and washed with water (5 mL) to give 118-3 (350 mg, 74%) as a white solid.

Synthesis of Compound 145 (T-118).

To a solution of 118-3 (252 mg, 1.3 mmol) and NaOH (70 mg, 1.8 mmol) in H₂O/THF (5 mL/2.5 mL) was added 2-bromo-1-p-tolylethanone (293 mg, 1.37 mmol) in batches. The mixture was stirred at 40° C. for 2 h. After cooling to r.t., the formed precipitate was filtered off. The solid was washed with water (5 mL), dried and then triturated in MeOH to give Compound 145 (70 mg, 17%) as a white solid.

Example 18. Reporter Displacement Assay

HDAC2 containing a C-terminal HIS-Tag (Proteros) and fluorescently-labeled anti-HIS-antibody are diluted in one vial in assay buffer 50 mM Tris, pH 8.0, 1 mM DTT, 150 mM NaCl, and 0.01% Tween20. Components are pre-incubated for 30 min, then a small volume of reporter probe (Proteros) is added from a highly concentrated stock and incubation is continued for another 30 min. Final concentrations after adding the reporter probe amount to 20 nM HDAC2, 4 nM antibody, and 180 nM probe.

Ten μl/well of pre-formed complex are transferred into 384 well assay plates (Corning). Compounds to be profiled are serially diluted from $1\times10^1$-$5.7\times10^{-5}$ mM in DMSO and 60 nl are added to assay plates by pintool transfer (CybiWell, Cybio). Fluorescence intensity signal is read after 4 h in a Pherastar FS (BMG Labtech) at 337/665 nm.

For $K_d$ determination, percent probe displacement values are calculated for each compound concentration and plotted against the compound concentration. IC₅₀-like values (corresponding to 50% probe displacement) are calculated using standard fitting algorithms. Since the reporter probe is used at a concentration reflecting its own $K_d$ value, compound $K_d$ values can be calculated according to the Cheng Prusoff equation.

The results of this assay for compounds useful in this invention are reported in Table 2, below. In the table, "A" indicates a $K_d$ value of less than 0.1 μM; "B" a $K_d$ value of between 0.1 μM and 1.0 μM; "C" a $K_d$ value of greater than 1.0 μM and less than or equal to 10.0 μM; and "D" a $K_d$ value of greater than 10.0 μM.

TABLE 2

HDAC2 $K_d$ Values for Exemplary Compounds Useful in the Invention

| Compound | $K_d$ |
|---|---|
| 100 | C |
| 101 | A |
| 102 | A |
| 103 | A |
| 104 | B |
| 105 | C |
| 106 | A |
| 107 | A |
| 108 | B |
| 109 | D |
| 110 | A |
| 111 | B |
| 112 | B |
| 113 | B |
| 114 | C |
| 115 | B |
| 116 | A |
| 117 | A |
| 118 | A |
| 119 | A |
| 120 | B |
| 121 | B |
| 122 | B |
| 123 | A |
| 124 | B |
| 125 | A |
| 126 | B |
| 127 | B |
| 128 | A |
| 129 | A |
| 130 | B |
| 131 | A |
| 132 | B |
| 133 | A |
| 134 | B |
| 135 | B |
| 136 | B |
| 137 | A |
| 138 | B |
| 139 | B |
| 140 | B |
| 141 | B |
| 142 | A |
| 143 | B |
| 144 | B |
| 145 | B |

Morris Water Maze Task

The compounds described herein (e.g., compounds according to Formula (I), (II), (IIIa), (III), (IV), (V), or (VI)) can be examined for its efficacy in the model behavior paradigm, the Morris water maze task as described below:

The water maze task was originally designed by Morris et al. (J Neurosci Methods. 1984; 11: 47-60). Testing is performed in a large dark-colored tank (200 cm in diameter) filled with clear water at a temperature of 25.0±1.0° C. A submerged platform (square platform: 10×10 cm; 1.5 cm below water surface) is placed in the middle of the of the NW quadrant. The starting locations, which are labeled N, NE, E, SE, S, SW, W, NW, are located arbitrarily on the pool rim. The rats are lowered into the pool with their nose pointing toward the wall at one of the starting points. The release point adjacent to platform location (NW) is not used.

At first, before the compound treatment is started, the visible platform pre-training is performed to determine whether any non-cognitive performance impairments (e.g. visual impairments and/or swimming difficulties) are present, which might affect performance on the place or probe trials. All rats receive 4 trials in one day with inter-trial interval of 15 min. On each trial, rats are placed in a fixed position in the swimming pool facing the wall and are allowed to swim to a platform with a rod (cue) 20 cm above water level randomly placed in middle of the pool. They are allowed 60 s to find the platform, which they stay on for 15 s before being removed from the pool. If a rat does not find the platform within 60 s, the rat will be gently guided to the platform and allowed to remain there for 15 s. The time for each rat to reach the cued platform, distance swam, thigmotaxis, and the swim speed are recorded. After the visible platform pre-training is completed, the data is analyzed and the rats are assigned to the different treatment groups based on their pre-training performance. This procedure is performed to ensure that each treatment group consist equally both good and poor performers in the cued version of the water maze task.

Acquisition training—week 1: After completion of cued trials, acquisition (place) trials are executed to determine the rat's ability to learn the spatial relationship between distant cues and the escape platform (submerged, no cue rod), which remain in the same location for all place trials. The starting points are randomized (NW is not used). The rats receive four trials (15 min apart, 60 s maximum for each trial) each day for 4 days. Latency, path length, thigmotaxis and swim speed are recorded.

Acquisition training—week 2: A second set of acquisition trials is executed to determine the rat's ability to learn the spatial relationship between distant cues and the escape platform (submerged, no cue rod), which remain in the same location for all place trials. The starting points are randomized (NW is not used). The rats receive four trials (15 min apart, 60 s maximum for each trial) each day for 4 days. Latency, path length, thigmotaxis and swim speed are recorded.

Probe trial: A single probe trial is conducted 24 hours after the last place trials to evaluate memory retention capabilities. The platform is removed from the water maze and rat is started to swim in the quadrant opposite to one the platform was placed before. The rats are allowed to swim for 60 s during the probe trial. During the probe trial, the time spent in target quadrant and target platform annulus (36-cm-diameter circular area surrounding platform), and crosses over the target platform position are measured (memory retention).

After completing the behavioral tests, the rats are sacrificed and tissue collected for further analysis. Blood was collected and processed to peripheral mononuclear cells and plasma. The cells can be further assayed for acetylation marks to demonstrate that compounds were inhibiting HDAC2 activity. The plasma can be frozen and later assayed by mass spectrometry for the presence of compound. Brain can be collected, dissected into cerebellum and hippocampus. Cerebellum can be frozen and later homogenized and the compound can be extracted and measured by mass spectrometry.

Hippocampal brain tissue can be processed to extract RNA for gene expression analysis. Tissue can be washed with phosphate buffered saline (PBS). RNA can be isolated using the RNeasy isolation kit (Qiagen) according to manufacturer's instructions. The RNA is eluted in 30 µl RNAse free water. The concentration of the isolated RNA can be measured by nanodrop. The RNA can be converted into cDNA with the iScript kit (Biorad) according to manufacturer's instructions. 800 ng of RNA was used per sample. After cDNA synthesis the DNA was diluted 1:5 with milliQ water. Quantitative PCR was done with the SSo advanced supermix (Biorad). Reactions can be done in a white 96-well plate, each reaction contained 1 µl template, 0.75 µl primer mix (forward & reverse, both at 10 µM), 5.75 µl water and 7.5 µL SSo SYBR green advanced supermix. Detection can be done with a CFX Connect Instrument (Biorad). Gene-specific primers for the following genes can be used in these studies: GAPDH—glyceraldehyde-3-phosphate dehydrogenase: BDNF—Brain Derived Neurotrophic Factor: GRIN2A and GRIN2B Glutamate receptor N-methyl D-aspartate-associated proteins 1 & 2: CDKS—cyclin-dependent kinase 5: HOMER1: GRIA1 and GRIA2—glutamate receptor, AMPA 1 & 2: EGR1—early growth response 1: NEFL—neurofilament, light polypeptide: SYT1—Synaptotagmin 1: SYP—synaptophysin. Values can be normalized to expression levels of GAPDH. Three replicates of each sample can be run in each assay and the mean of the replicates can be compared for statistical significant changes.

Peripheral blood mononuclear cells can be isolated using a Ficoll-Paque Plus (GE Healthcare) and can be tested for acetylation marks following treatment with HDCA2 inhibitors. Blood cells can be lysed and proteins can be extracted using 13 RIPA buffer containing proteinase (complete, Roche) and phosphatase inhibitors (1 mMb-glycerophosphate, 10 mM NaF, 0.1 mM Na3VO4) and then can be transferred onto PVDF membranes (Biorad) and stripped using stripping buffer (Thermo Scientific). The following primary antibodies can be used: acetyl-K (Cell Signaling) and actin (Sigma). Secondary antibodies were horseradish peroxidase-linked (GE Healthcare). Signal intensities can be quantified using Image J 1.42q and normalized to values of actin.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A compound having structural formula I:

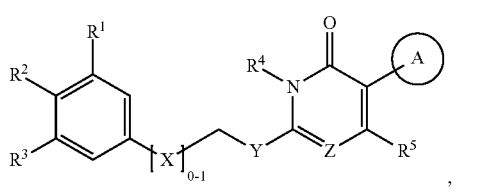

(I)

or a pharmaceutically acceptable salt thereof, wherein:
ring A is an optionally substituted carbocyclyl or optionally substituted aryl;
X, if present, is selected from oxazol-diyl, —C(=O)—, —CH(OH)—, and C(=NOH);
Y is selected from —O— and —S—;
Z is selected from N and C($R^7$), wherein $R^7$ is selected from hydrogen, halogen, $C_1$-$C_4$ alkyl and —O—$C_1$-$C_4$ alkyl, wherein the alkyl portion of $R^7$ is optionally substituted;
each of $R^1$, $R^2$ and $R^3$ is independently selected from hydrogen, halo, optionally substituted heterocyclyl, —N($R^6$)$_2$, —C(O)—N—($C_1$-$C_4$ alkyl)$_2$, —C(O)—NH—($C_1$-$C_4$ alkyl), —C(O)—NH$_2$, —S(O)$_2$—N—($C_1$-$C_4$ alkyl)$_2$, —S(O)$_2$—NH—($C_1$-$C_4$ alkyl), —S(O)$_2$—NH$_2$, —S(O)$_2$—($C_1$-$C_4$ alkyl), —$C_1$-$C_4$ alkyl, $C_1$-$C_4$ haloalkyl, —O—$C_1$-$C_4$ alkyl, and —O—$C_1$-$C_4$ haloalkyl, wherein:
each $R^6$ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)$_2$, —C(O)—NH—($C_1$-$C_4$ alkyl), —C(O)—NH$_2$, and —S(O)$_2$—$C_1$-$C_4$ alkyl, or
two $R^6$ bound are taken together with the nitrogen atom to which they are bound to form an optionally substituted heterocyclyl or an optionally substituted heteroaryl; and
any alkyl portion of $R^1$, $R^2$, $R^3$ or $R^6$ is optionally substituted, or
any two of $R^1$, $R^2$ and $R^3$ are taken together to form an optionally substituted heterocyclyl, heteroaryl, carbocyclyl or aryl ring;
$R^4$ is selected from hydrogen, —CH(R')(R"), optionally substituted heterocyclyl, optionally substituted heteroaryl, optionally substituted aryl, and optionally substituted carbocyclyl, wherein:
each of R' and R" is independently selected from hydrogen, $C_1$-$C_6$ alkyl, $C_2$-$C_6$ alkenyl or alkynyl, —($C_0$-$C_6$ alkylene)-(optionally substituted carbocyclyl), —($C_0$-$C_6$ alkylene)-(optionally substituted aryl), —($C_0$-$C_6$ alkylene)-(optionally substituted heterocyclyl), and —($C_0$-$C_6$ alkylene)-(optionally substituted heteroaryl), —($C_2$-$C_6$ alkenylene or alkynylene)-(optionally substituted carbocyclyl), —($C_2$-$C_6$ alkenylene or alkynylene)-(optionally substituted aryl), —($C_2$-$C_6$ alkenylene or alkynylene)-(optionally substituted heterocyclyl), and —($C_2$-$C_6$ alkenylene or alkynylene)-(optionally substituted heteroaryl);
each alkyl, alkenyl, alkynyl, alkylene, alkenylene and alkynylene portion of R' and R" is optionally substituted; and
one or more methylene units of each alkyl, alkenyl, alkynyl, alkylene, alkenylene and alkynylene portion of R' and R" are optionally and independently replaced with —O—, —S—, —S(O)—, —S(O)$_2$, or —N($R^6$)—;
$R^5$ is selected from —OH, optionally substituted $C_1$-$C_4$ alkyl, optionally substituted $C_2$-$C_4$ alkenyl, and —O—C(O)-(optionally substituted $C_1$-$C_4$ alkyl),
wherein:
when X is absent, Y is S; Z is N and $R^2$ is halo or hydrogen, ring A is other than unsubstituted phenyl unsubstituted cyclohexyl, or unsubstituted cyclopentyl;
when X is —C(O)—, Y is S; Z is N and $R^2$ is halo, methoxy, methyl or hydrogen, ring A is other than unsubstituted phenyl; and
the compound is other than

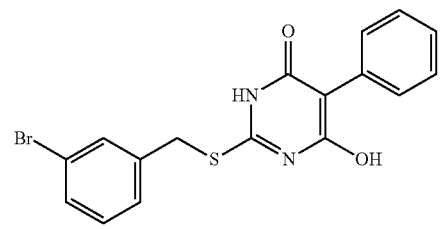

, or

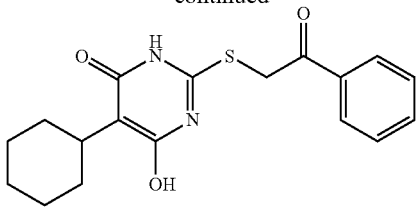

2. The compound of claim 1, wherein:
R¹ is hydrogen;
R² is selected from hydrogen, fluoro, chloro, methyl, methoxy, amino, methylcarbonylamino, methylcarbonyl-N-methylamino, dimethylamino, t-butoxycarbonylamino, 2-oxopyrrolidin-1-yl, trifluoromethylcarbonylamino, isopropylcarbonylamino, and phenylcarbonylamino; and
R³ is selected from hydrogen, fluoro, chloro and methyl, or
R² and R³ are taken together to form 1H-benzo[d]imidazol-5-yl.
3. The compound of claim 1, wherein X is C(O).
4. The compound of claim 1, wherein Y is S.
5. The compound of claim 1, wherein R⁴ is selected from hydrogen, $C_1$-$C_4$ alkyl, $C_2$-$C_4$ alkenyl, $C_3$-$C_6$ cycloalkyl, and phenyl.
6. The compound of claim 5, wherein R⁴ is selected from hydrogen, methyl, ethyl, isopropyl, 1-propenyl, cyclopropyl, cyclopentyl and phenyl.
7. The compound of claim 1, wherein R⁵ is selected from hydrogen, hydroxy, methyl and ethyl.
8. The compound of claim 1, wherein Z is N.
9. The compound of claim 1, wherein ring A is phenyl or cyclopentyl.
10. A pharmaceutical composition comprising:
(a) a compound having structural formula II:

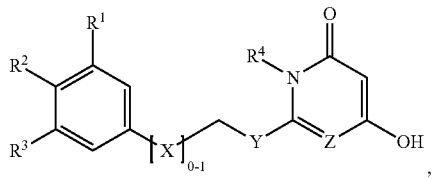

or a pharmaceutically acceptable salt thereof,
wherein:
X, if present, is selected from oxazol-diyl, —C(=O)—, —CH(OH)—, and C(=NOH);
Y is selected from —O— and —S—;
Z is selected from N and C(R⁷), wherein R⁷ is selected from hydrogen, halogen, $C_1$-$C_4$ alkyl and —O—$C_1$-$C_4$ alkyl, wherein the alkyl portion of R⁷ is optionally substituted;
each of R¹, R² and R³ is independently selected from hydrogen, halo, optionally substituted heterocyclyl, —N(R⁶)₂, —C(O)—N—($C_1$-$C_4$ alkyl)₂, —C(O)—NH—($C_1$-$C_4$ alkyl), —C(O)—NH₂, —S(O)₂—N—($C_1$-$C_4$ alkyl)₂, —S(O)₂—NH—($C_1$-$C_4$ alkyl), —S(O)₂—($C_1$-$C_4$ alkyl), —S(O)₂—NH₂, —$C_1$-$C_4$ alkyl, $C_1$-$C_4$ haloalkyl, —O—$C_1$-$C_4$ alkyl, and —O—$C_1$-$C_4$ haloalkyl, wherein:

each R⁶ is independently selected from hydrogen, —$C_1$-$C_4$ alkyl, —C(O)—$C_1$-$C_4$ alkyl, —C(O)-carbocyclyl, —C(O)-heterocyclyl, —C(O)-aryl, —C(O)-heteroaryl, —C(O)—O—$C_1$-$C_4$ alkyl, —C(O)—N—($C_1$-$C_4$ alkyl)₂, —C(O)—NH—($C_1$-$C_4$ alkyl), —C(O)—NH₂, and —S(O)₂—$C_1$-$C_4$ alkyl, or
two R⁶ bound are taken together with the nitrogen atom to which they are bound to form an optionally substituted heterocyclyl or an optionally substituted heteroaryl;
any alkyl portion of R¹, R², R³ or R⁶ is optionally substituted; and
at least one of R¹, R² or R³ is other than hydrogen, or
any two of R¹, R² and R³ are taken together to form an optionally substituted heterocyclyl, heteroaryl, carbocyclyl or aryl ring; and
R⁴ is selected from methyl, ethyl, isopropyl and $C_2$-$C_3$ alkenyl,
wherein the compound is other than:

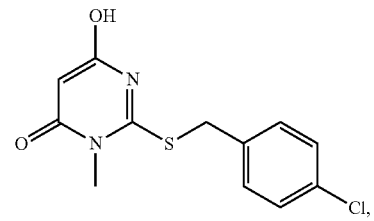

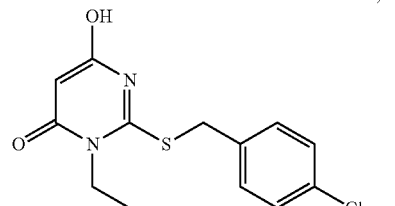

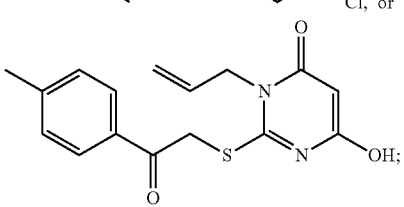

and
(b) a pharmaceutically acceptable carrier.
11. A compound of structural formula IV:

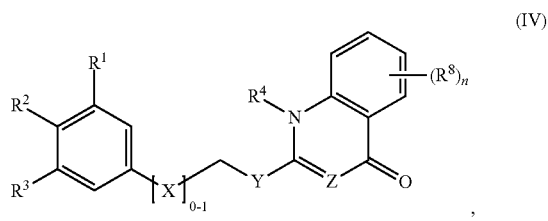

or a pharmaceutically acceptable salt thereof, wherein:
X, if present, is selected from oxazol-diyl, —C(=O)—, —CH(OH)—, and C(=NOH);
Y is selected from —O— and —S—;

Z is selected from N and C(R$^7$), wherein R$^7$ is selected from hydrogen, halogen, C$_1$-C$_4$ alkyl and —O—C$_1$-C$_4$ alkyl, wherein the alkyl portion of R$^7$ is optionally substituted;

each of R$^1$, R$^2$ and R$^3$ is independently selected from hydrogen, halo, optionally substituted heterocyclyl, —N(R$^6$)$_2$, —C(O)—N—(C$_1$-C$_4$ alkyl)$_2$, —C(O)—NH—(C$_1$-C$_4$ alkyl), —C(O)—NH$_2$, —S(O)$_2$—N—(C$_1$-C$_4$ alkyl)$_2$, —S(O)$_2$—NH—(C$_1$-C$_4$ alkyl), —S(O)$_2$—(C$_1$-C$_4$ alkyl), —S(O)$_2$—NH$_2$, —C$_1$-C$_4$ alkyl, C$_1$-C$_4$ haloalkyl, —O—C$_1$-C$_4$ alkyl, and —O—C$_1$-C$_4$ haloalkyl, wherein:

each R$^6$ is independently selected from hydrogen, —C$_1$-C$_4$ alkyl, —C(O)—C$_1$-C$_4$ alkyl, —C(O)-carbocyclyl, —C(O)-heterocyclyl, —C(O)-aryl, —C(O)-heteroaryl, —C(O)—O—C$_1$-C$_4$ alkyl, —C(O)—N—(C$_1$-C$_4$ alkyl)$_2$, —C(O)—NH—(C$_1$-C$_4$ alkyl), —C(O)—NH$_2$, and —S(O)$_2$—C$_1$-C$_4$ alkyl, or two R$^6$ bound are taken together with the nitrogen atom to which they are bound to form an optionally substituted heterocyclyl or an optionally substituted heteroaryl; and any alkyl portion of R$^1$, R$^2$, R$^3$ or R$^6$ is optionally substituted, or any two of R$^1$, R$^2$ and R$^3$ are taken together to form an optionally substituted heterocyclyl, heteroaryl, carbocyclyl or aryl ring;

R$^4$ is selected from —C$_1$-C$_4$ alkyl and —C$_2$-C$_4$ alkenyl;

R$^8$, if present, is selected from halogen, optionally substituted —C1-C4-alkyl, optionally substituted —O—C$_1$-C$_4$ alkyl, or any two R$^8$ are taken together with the atoms to which they are bound to form an optionally substituted heterocyclyl or optionally substituted heteroaryl; and n is 0, 1, 2, 3, 4, or 5, wherein the compound is other than:

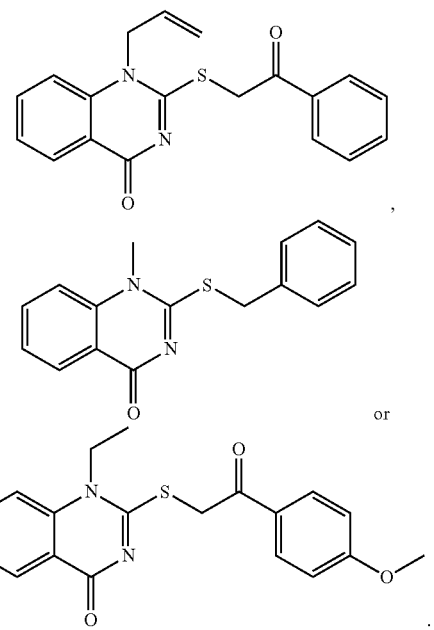

* * * * *